United States Patent
Toida et al.

(10) Patent No.: US 11,243,467 B2
(45) Date of Patent: Feb. 8, 2022

(54) COMPOUND, RESIN, RESIST COMPOSITION OR RADIATION-SENSITIVE COMPOSITION, RESIST PATTERN FORMATION METHOD, METHOD FOR PRODUCING AMORPHOUS FILM, UNDERLAYER FILM FORMING MATERIAL FOR LITHOGRAPHY, COMPOSITION FOR UNDERLAYER FILM FORMATION FOR LITHOGRAPHY, METHOD FOR FORMING CIRCUIT PATTERN, AND PURIFICATION METHOD

(71) Applicant: Mitsubishi Gas Chemical Company, Inc., Tokyo (JP)

(72) Inventors: Takumi Toida, Hiratsuka (JP); Youko Shimizu, Hiratsuka (JP); Takashi Makinoshima, Hiratsuka (JP); Takashi Sato, Hiratsuka (JP); Masatoshi Echigo, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 15/759,076

(22) PCT Filed: Sep. 8, 2016

(86) PCT No.: PCT/JP2016/076392
§ 371 (c)(1),
(2) Date: Mar. 9, 2018

(87) PCT Pub. No.: WO2017/043561
PCT Pub. Date: Mar. 16, 2017

(65) Prior Publication Data
US 2019/0056657 A1 Feb. 21, 2019

(30) Foreign Application Priority Data
Sep. 10, 2015 (JP) .............................. JP2015-178545

(51) Int. Cl.
G03F 7/004 (2006.01)
C07C 39/367 (2006.01)
(Continued)

(52) U.S. Cl.
CPC .......... *G03F 7/0045* (2013.01); *C07C 39/367* (2013.01); *C07C 43/23* (2013.01);
(Continued)

(58) Field of Classification Search
CPC ........ G03F 7/0392; G03F 7/30; G03F 7/0045; C07D 307/77; C07D 311/00;
(Continued)

(56) References Cited

U.S. PATENT DOCUMENTS 2,100,798 A 11/1937 Dilthey
2,546,872 A 3/1951 Schmid
(Continued)

FOREIGN PATENT DOCUMENTS

CN 1414031 4/2003
CN 1853141 10/2006
(Continued)

OTHER PUBLICATIONS

T. Nakayama et al., "A New Three-Component Photoresist Based on Calix[4]resorcinarene Derivative, a Cross-linker, and a Photo-acid Generator", Bull. Chem. Soc. Jpn., 71, 2979-2984 (1998), The Chemical Society of Japan.
(Continued)

*Primary Examiner* — John S Chu
(74) *Attorney, Agent, or Firm* — Fitch, Even, Tabin & Flannery LLP

(57) ABSTRACT

The present invention employs a compound represented by the following formula (1) and/or a resin comprising the compound as a constituent:

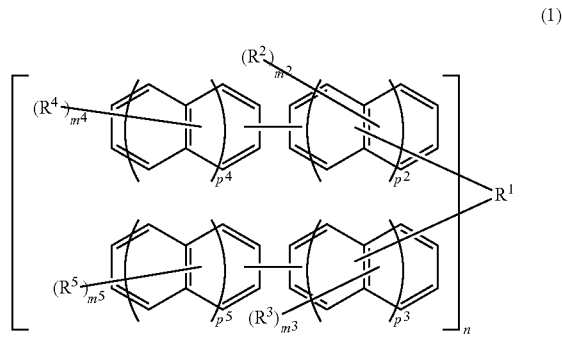

(1)

wherein $R^1$ is a 2n-valent group of 1 to 60 carbon atoms or a single bond; $R^2$ to $R^5$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, a hydroxy group, or a group in which a hydrogen atom of a hydroxy group is replaced with an acid dissociation group, provided that at least one selected from $R^2$ to $R^5$ is a group in which a hydrogen atom of a hydroxy group is replaced with an acid dissociation group; $m^2$ and $m^3$ are each independently an integer of 0 to 8; $m^4$ and $m^5$ are each independently an integer of 0 to 9, provided that $m^2$, $m^3$, $m^4$, and $m^5$ are not 0 at the same time; n is an integer of 1 to 4; and $p^2$ to $p^5$ are each independently an integer of 0 to 2.

13 Claims, No Drawings

(51) Int. Cl.

| | | |
|---|---|---|
| *C07C 69/96* | (2006.01) | |
| *C07D 307/56* | (2006.01) | |
| *G03F 7/039* | (2006.01) | |
| *G03F 7/30* | (2006.01) | |
| *G03F 7/023* | (2006.01) | |
| *G03F 7/09* | (2006.01) | |
| *G03F 7/16* | (2006.01) | |
| *G03F 7/022* | (2006.01) | |
| *C07C 43/23* | (2006.01) | |
| *C07C 39/15* | (2006.01) | |

(52) U.S. Cl.
CPC ............ *C07C 69/96* (2013.01); *C07D 307/56* (2013.01); *G03F 7/0226* (2013.01); *G03F 7/0236* (2013.01); *G03F 7/039* (2013.01); *G03F 7/092* (2013.01); *G03F 7/094* (2013.01); *G03F 7/16* (2013.01); *G03F 7/30* (2013.01); *C07C 39/15* (2013.01)

(58) Field of Classification Search
CPC .. C07D 493/04; C07D 307/56; C07D 39/367; C07C 37/72; C07C 43/23; C07C 69/96
USPC ................ 430/270.1, 326; 549/382; 568/719
See application file for complete search history.

(56) References Cited

U.S. PATENT DOCUMENTS

| | | | |
|---|---|---|---|
| 2,587,437 A | 2/1952 | Bralley et al. | |
| 3,947,468 A | 3/1976 | Hall | |
| 4,252,884 A | 2/1981 | Bennett | |
| 4,289,839 A | 9/1981 | Dipippo | |
| 4,482,489 A | 11/1984 | Dipippo | |
| 4,579,758 A | 4/1986 | Dorsch | |
| 5,332,648 A | 7/1994 | Kihara | |
| 5,986,094 A | 11/1999 | Ghoshal | |
| 6,784,228 B2 | 8/2004 | Ogura | |
| 6,794,408 B2 | 9/2004 | Eder | |
| 7,871,751 B2 | 1/2011 | Echigo | |
| 9,136,121 B2 | 9/2015 | Hatakeyama | |
| 9,274,426 B2 | 3/2016 | Rahman | |
| 9,316,913 B2 | 4/2016 | Echigo | |
| 9,540,339 B2 | 1/2017 | Echigo | |
| 9,908,831 B2 | 3/2018 | Echigo | |
| 10,303,055 B2 * | 5/2019 | Sato | G03F 7/2037 |
| 10,377,734 B2 * | 8/2019 | Echigo | G03F 7/0045 |
| 2002/0106909 A1 | 8/2002 | Kato | |
| 2003/0092852 A1 | 5/2003 | Ogura | |
| 2004/0197709 A1 | 10/2004 | Arase | |
| 2005/0074695 A1 | 4/2005 | Nakamura | |
| 2005/0255712 A1 | 11/2005 | Kato et al. | |
| 2007/0059632 A1 * | 3/2007 | Oguro | C07D 311/82 430/270.1 |
| 2007/0172759 A1 | 7/2007 | Ogihara | |
| 2007/0232839 A1 | 10/2007 | Yoshitomo et al. | |
| 2007/0275325 A1 | 11/2007 | Hatakeyama | |
| 2008/0113294 A1 | 5/2008 | Echigo | |
| 2008/0138744 A1 | 6/2008 | Hatanaka | |
| 2008/0153031 A1 | 6/2008 | Echigo et al. | |
| 2009/0171061 A1 | 7/2009 | Sue | |
| 2009/0246684 A1 | 10/2009 | Kim et al. | |
| 2009/0261300 A1 | 10/2009 | Watanabe | |
| 2010/0047709 A1 | 2/2010 | Echigo | |
| 2010/0099044 A1 | 4/2010 | Hatakeyama | |
| 2010/0104977 A1 | 4/2010 | Hatakeyama | |
| 2010/0136477 A1 | 6/2010 | Ng | |
| 2010/0190107 A1 | 7/2010 | Shibata et al. | |
| 2010/0207516 A1 | 8/2010 | Moriwaki | |
| 2010/0227859 A1 | 9/2010 | Li | |
| 2010/0285407 A1 | 11/2010 | Ogihara | |
| 2010/0316950 A1 | 12/2010 | Oguro et al. | |
| 2011/0177459 A1 | 7/2011 | Ogihara | |
| 2011/0230058 A1 | 9/2011 | Sakamoto et al. | |
| 2011/0274713 A1 | 11/2011 | Burn et al. | |
| 2011/0311920 A1 | 12/2011 | Kinsho | |
| 2012/0064725 A1 | 3/2012 | Kinsho | |
| 2012/0171611 A1 | 7/2012 | Ideno et al. | |
| 2012/0184103 A1 | 7/2012 | Ogihara | |
| 2012/0220112 A1 | 8/2012 | Hatakeyama | |
| 2012/0228584 A1 | 9/2012 | Wigglesworth | |
| 2013/0004896 A1 | 1/2013 | Echigo | |
| 2013/0056653 A1 | 3/2013 | Hatakeyama | |
| 2013/0056654 A1 | 3/2013 | Hatakeyama et al. | |
| 2013/0084705 A1 | 4/2013 | Nakafuji et al. | |
| 2013/0087529 A1 | 4/2013 | Hatakeyama | |
| 2013/0150627 A1 | 6/2013 | Okada | |
| 2014/0186776 A1 | 7/2014 | Uchiyama | |
| 2014/0248556 A1 | 9/2014 | Kato | |
| 2014/0248561 A1 * | 9/2014 | Echigo | C07D 311/96 430/281.1 |
| 2014/0308615 A1 | 10/2014 | Echigo | |
| 2014/0319097 A1 | 10/2014 | Kim | |
| 2014/0363768 A1 | 12/2014 | Kinsho | |
| 2014/0363955 A1 | 12/2014 | Hatakeyama | |
| 2014/0363957 A1 | 12/2014 | Hatakeyama et al. | |
| 2014/0363958 A1 | 12/2014 | Hatakeyama | |
| 2015/0030980 A1 | 1/2015 | Echigo | |
| 2015/0037735 A1 | 2/2015 | Yang et al. | |
| 2015/0090691 A1 | 4/2015 | Echigo | |
| 2015/0309403 A1 | 10/2015 | Rahman | |
| 2015/0368224 A1 | 12/2015 | Echigo | |
| 2015/0376157 A1 | 12/2015 | Echigo | |
| 2015/0376158 A1 | 12/2015 | Echigo | |
| 2015/0376202 A1 | 12/2015 | Echigo | |
| 2016/0130243 A1 | 5/2016 | Satou | |
| 2016/0145231 A1 | 5/2016 | Echigo | |
| 2017/0183279 A1 | 6/2017 | Echigo | |
| 2017/0349564 A1 | 12/2017 | Toida | |
| 2018/0074402 A1 | 3/2018 | Toida | |
| 2018/0074406 A1 | 3/2018 | Toida | |
| 2018/0208703 A1 | 7/2018 | Okada | |
| 2018/0246409 A1 | 8/2018 | Toida | |

FOREIGN PATENT DOCUMENTS

| | | |
|---|---|---|
| CN | 101889247 | 11/2010 |
| CN | 102070595 | 5/2011 |
| CN | 103304385 A | 9/2013 |
| CN | 103733136 | 4/2014 |
| CN | 103804196 A | 5/2014 |
| CN | 104557552 A | 4/2015 |
| EP | 1275673 | 1/2003 |
| EP | 1300403 | 4/2003 |
| EP | 1666970 | 6/2006 |
| EP | 2743249 | 6/2014 |
| EP | 2743769 | 6/2014 |
| EP | 2743770 A1 | 6/2014 |
| EP | 3279190 | 2/2018 |
| JP | S48049508 A | 7/1973 |
| JP | 62094841 A | 5/1987 |
| JP | S62-191850 A | 8/1987 |
| JP | H01283280 | 11/1989 |
| JP | H04217675 | 8/1992 |
| JP | H05-19463 A | 1/1993 |
| JP | H05034913 A | 2/1993 |
| JP | H05134415 A | 5/1993 |
| JP | H05163290 A | 6/1993 |
| JP | 05216235 A | 8/1993 |
| JP | H06049402 A | 2/1994 |
| JP | H06242607 A | 9/1994 |
| JP | H07215833 | 8/1995 |
| JP | H1025220 | 1/1998 |
| JP | H10045764 A | 2/1998 |
| JP | H11072925 | 3/1999 |
| JP | 2001042525 | 2/2001 |
| JP | 2002214769 | 7/2002 |
| JP | 2002-334869 A | 11/2002 |
| JP | 2002334896 | 11/2002 |
| JP | 2002341542 | 11/2002 |
| JP | 2003201333 | 7/2003 |
| JP | 2004-177668 A | 6/2004 |
| JP | 2004-271838 A | 9/2004 |
| JP | 2005-250434 A | 9/2005 |

(56) References Cited

FOREIGN PATENT DOCUMENTS

| | | |
|---|---|---|
| JP | 2005-266741 A | 9/2005 |
| JP | 2005-326838 A | 11/2005 |
| JP | 2005326868 A | 11/2005 |
| JP | 2005346024 A | 12/2005 |
| JP | 2006-036648 A | 2/2006 |
| JP | 2006098869 | 4/2006 |
| JP | 2006113136 | 4/2006 |
| JP | 2006160663 | 6/2006 |
| JP | 2006-213634 A | 8/2006 |
| JP | 2006259482 A | 9/2006 |
| JP | 2007019294 | 1/2007 |
| JP | 2007199653 | 8/2007 |
| JP | 2007-226170 A | 9/2007 |
| JP | 2007-226204 A | 9/2007 |
| JP | 2007262398 | 10/2007 |
| JP | 2007-326847 A | 12/2007 |
| JP | 2008065081 | 3/2008 |
| JP | 2008-145539 A | 6/2008 |
| JP | 2008201954 A | 9/2008 |
| JP | 2008239868 | 10/2008 |
| JP | 2009073738 A | 4/2009 |
| JP | 2009098155 A | 5/2009 |
| JP | 2009108313 | 5/2009 |
| JP | 2009-155256 A | 7/2009 |
| JP | 2009-173623 A | 8/2009 |
| JP | 2009300978 | 12/2009 |
| JP | 2010160189 | 7/2010 |
| JP | 2010170013 | 8/2010 |
| JP | 2010219295 | 9/2010 |
| JP | 2010235643 | 10/2010 |
| JP | 2011-068624 A | 4/2011 |
| JP | 2011-105887 A | 6/2011 |
| JP | 2011150023 | 8/2011 |
| JP | 20121687 | 1/2012 |
| JP | 2012-083731 A | 4/2012 |
| JP | 2012068652 | 4/2012 |
| JP | 2012077295 | 4/2012 |
| JP | 2012145897 | 8/2012 |
| JP | 2013-068928 A | 4/2013 |
| JP | 2013064978 A | 4/2013 |
| JP | 2013-083939 A | 5/2013 |
| JP | 2013083833 A | 5/2013 |
| JP | 2013087173 A | 5/2013 |
| JP | 2013137524 A | 7/2013 |
| JP | 2013253161 A | 12/2013 |
| JP | 2014196288 A | 10/2014 |
| JP | 2014205746 | 10/2014 |
| JP | 2015018220 | 1/2015 |
| JP | 2015018221 | 1/2015 |
| JP | 2015018223 | 1/2015 |
| JP | 2015-087115 A | 5/2015 |
| JP | 2015-514691 A | 5/2015 |
| JP | 2015-127821 A | 7/2015 |
| KR | 1020100095563 | 8/2010 |
| WO | 9736960 | 10/1997 |
| WO | 0214434 | 2/2002 |
| WO | 03017002 | 2/2003 |
| WO | 2004/066377 A1 | 8/2004 |
| WO | 2005029189 A1 | 3/2005 |
| WO | 2005111724 | 11/2005 |
| WO | 2006068267 A1 | 6/2006 |
| WO | 2007097457 | 8/2007 |
| WO | 2008053974 A1 | 5/2008 |
| WO | 2008137816 A2 | 11/2008 |
| WO | 2009/072465 A1 | 6/2009 |
| WO | 2009119201 A1 | 10/2009 |
| WO | 2009145224 | 12/2009 |
| WO | 2011/034062 A1 | 3/2011 |
| WO | 2012165507 A1 | 12/2012 |
| WO | 2013010102 | 1/2013 |
| WO | 2013/024778 A1 | 2/2013 |
| WO | 2013024777 A1 | 2/2013 |
| WO | 2013024779 A1 | 2/2013 |
| WO | 2013066067 | 5/2013 |
| WO | 2013184755 | 12/2013 |
| WO | 2014050690 | 4/2014 |
| WO | 2014123032 A1 | 8/2014 |
| WO | 2014199660 | 12/2014 |

OTHER PUBLICATIONS

Shinji Okazaki et al., "New Trends of Photoresists", CMC Publishing Co., Ltd., Sep. 2009, pp. 211-259.

Ahmed Munir et al., The Direct Bradsher Reaction. Part I. Synthesis of Thiophen Analogues of Linear Polycyclic Hydrocarbons, Journal of the Chemical Society, Perkin Transactions 1,1973, pp. 1099-1103.

Areephong, Jetsuda, et al., "A concise synthesis of functionalized 7-oxa-[5]-helicenes," Tetrahedron Letters, 2004, vol. 45, pp. 3067-3070.

Bentley, K. W., and Robinson, R., "A Synthesis of alpha-Anhydrotrimethylbrazilone," Tetrahedron Letters, 1959, vol. 1, Issue 2, pp. 11-14.

Brecher, Jonathan, Graphical Representation Standards for Chemical Structure Diagrams, Pure Appl. Chem., 2008, pp. 277-410, vol. 80, No. 2, Cambridge, Massachusetts.

Burnett, James C., et al. "Novel small molecule inhibitors of botulinum neurotoxin A metalloprotease activity," Biochemical and Biophysical Research Communications, vol. 310, No. 1, Oct. 2003, pp. 84-93.

Cameron, Donald W., et al., "Synthesis of a natural polychloro dinaphthofuran quinone," Tetrahedron Letters, 1980, vol. 21(14), pp. 1385-1386.

Chatterjea, J.N., "Experiments on the Syntheses of Furano Compounds. Part XII. Further Transformations of isoCoumaranone," Journal of the Indian Chemical Society, 1957, vol. 34, Issue 4, pp. 299-305.

Clowes, G. A., et al., "Studies of the Scholl reaction: Oxidative Dehydrogenation involving 1-Ethoxynaphthylenen and Related Compounds," J Chem. Soc (C) 2519-2526 (1968).

Dann, von Otto, and Hofmann, Hans, Synthese von ( )-Brasilin, Justus Liebigs Annalen der Chemie, 1963, vol. 667, Issue 1, pp. 116-125.

English Translation of JP H01-283280 A, Nov. 14, 1989.

European Journal of Medicinal Chemistry, published bi-monthly, Ejmcs, 13(4): 381-385 (1978).

Ghodratbeigi Mohsen et al., "Design, modeling and synthesis of molecular tweezers with self-assembly Properties," Journal of Molecular Structure, 2011, vol. 990, No. 1, pp. 140-151.

Hagihara K. et al., "The effect of Ti-addition on plastic deformation and fracture behavior of directionally solidified NliAl/Cr(Mo) eutetic alloys," Intermetallics, 2006, vol. 14, No. 10, pp. 1326-1331.

Hannuksela, Miska M. et al., "Hook for scalable extensions: video parameter set," Joint Collaborative Team on Video Coding (JCT-VC) of ITU-T SG 16 WP 3 and ISO/IEC JTC 1/SC 29/WG 11, May 2012, pp. 1-6.

International Preliminary Report on Patentability issued in International Application No. PCT/JP2012/070304.

International Search Report dated Feb. 25, 2014 for PCT/JP2014/051775 and English translation of the same (4 pages).

International Search Report dated Feb. 9, 2016, for PCT/JP2015/084907 and English translation of the same (7 pages).

International Search Report dated Mar. 25, 2014 for International Application No. PCT/JP2014/052524 with English Translation (8 pages).

International Search Report dated May 13, 2014 for International Application No. PCT/JP2014/052530 with English Translation (8 pages).

International Search Report dated Oct. 23, 2012 issued in International Application No. PCT/JP2012/070304.

International Search Report dated Sep. 11, 2012 for International Application No. PCT/JP2012/070305 with English Translation (5 pages).

International Search Report on Patentability for PCT/JP2016/056332 dated May 31, 2016; English translation submitted herewith (11 pages).

(56) References Cited

OTHER PUBLICATIONS

International Search Report on Patentability for PCT/JP2016/056333 dated May 24, 2016; English translation submitted herewith (7 pages).
Jha Amitabh and Beal Jennifer, "Convenient synthesis of 12H-benzo[a]xanthenes from 2-tetralone," Tetrahedron Letters, 2004, vol. 45, No. 49, pp. 8999-9001.
Journal of the Chemical Society, p. 5336-5341 (Nov. 1963).
Luo, Junfei et al., "Salicylic acids as readily available starting materials for the synthesis of meta-substituted biaryls," ChemComm, 2015, vol. 51, pp. 3127-3130.
Machine English Translation of JP 2008-239868 A, Oct. 9, 2008.
Massif, Cedrik, et al. "New insights into the water-solubilisation of fluorophores by post-synthetic 'click' and Sonogashira reactions," Organic & Biomolecular Chemistry, vol. 10, No. 22, Apr. 2012, pp. 4430-4336.
Nature, 161:930-931 (1948).
Nishiyama Tomihiro et al., Antioxidant activities of fused heterocyclic compounds, xanthene-2,7-diols with BHT or Catechol skeleton, Polymer Degradation and Stability, 1998, vol. 62, No. 3, pp. 529-534.
Ohishi Takeshi. Tetrahedron Letters 42 (2001) 2493-2496.
Osman A-M, Reactions Between Chloro-p-benzoquinones and Beta-Naphtol, Journal of Organic Chemistry, 1957, vol. 22, pp. 342-344.
Percec, Virgil, et al., Synthesis of Aromatic Polyethers by Scholl Reaction. I. Poly(1,1'-Dinaphthyl Ether Phenyl Sulfone)s and Poly(1,1'-Dinaphthyl Ether Phenyl Ketone)s, Journal of Polymer Science: Part A: Polymer Chemistry, 1988, vol. 26, pp. 783-805.
Percec, Virgil, et al., "Synthesis of Aromatic Polyethers by Scholl Reaction. VI. Aromatic Polyethers by Cation-Radical Polymerization of 4,4'-, 3,3'-, and 2-2'-Bis(1-naphthoxy)biphenyls and of 1,3-Bis(1-naphthoxy)benzene," Macromolecules, 1992, vol. 25(1), pp. 64-74.
Protiva, Miroslav et al., Potential metabolites of tricyclic neuroleptics: 2,8-dihydroxy and 3,8-dihydroxy derivatives of 10-(4-methylpiperazino)-10,11-dihydrodibenzo[b,f]thiepin, Part CXXXIII in the series Neurotropic and Psychotropic Agents, Collection of Czechoslovak Chemical Communications, 1979, vol. 44, No. 10, pp. 2987-2996.
Protiva, Miroslav, et al., "Potential metabolites or tricyclic neuroleptics 3,7-dimethoxy and 7,8-dimethoxy derivatives of 10-{4-methylpiperazino )-10,11-dihydrodibenzo[b,f]thiepin", Collection of Czechoslovak Chemical Communications, 1981, vol. 46, pp. 1808-1817.
Singh Ritesh and Panda Gautam, "Scandium triflate-catalyzed one-pot domino approach towards general and efficient syntheses of unsymmetrical 9-substituted xanthene derivatives," Organic & Biomolecular Chemistry, 2010, vol. 8, No. 5, pp. 1097-1105.
Sirkecioglu Okan et al., A Novel Synthesis of 14-(Hydroxymethylalkyl) Derivatives of Dibenzoxanthenes and 3,3-Dimethyl-4-(2-hydroxy-1-naphthyl)benzo[f]chroman, Journal of Heterocyclic Chemistry, Mar. 1, 1998, vol. 35, No. 2, pp. 457-460.
Sirringhaus Henning et al., Dibenzothienobisbenzothiophene—a novel fused-ring oligomer with high field-effect mobility, Journal of Materials Chemistry, 1999, vol. 9, pp. 2095-2101.
Skandinavisches Archiv fuer Physiologie, 43: 215-243 (1923).
Tian-jun Liu, Ke-shen Zhang, Yong-jun Chen, Dong Wang and Chao-jun Li, "Chiral Conjugated Oligomer Based on 1, 1'-Binol With 3, 3 ' -Acetylene-Phenylene-Acetylene Spacer", Chinese Journal of Polymer Science, Mar. 8, 2001, vol. 19, No. 5, p. 521-526.
Written Opinion of the International Searching Authority issued in International Application No. PCT/JP2012/070304 (including translation), dated Oct. 23, 2012.
U.S. Appl. No. 15/539,560, entitled "Compound, Resin, Material For Forming Underlayer Film For Lithography, Underlayer Film For Lithography, Pattern Forming Method, And Purification Method," filed Jun. 23, 2017, which entered the U.S. national phase from International Application No. PCT/JP2015/084907, filed on Dec. 14, 2015, which published as US 2017/0349564 A1 on Dec. 7, 2017.
U.S. Appl. No. 15/560,059, Entitled "Compound, Resist Composition, And Method For Forming Resist Pattern Using It," filed Sep. 20, 2017, which entered the U.S. national phase from International Application No. PCT/JP2016/056332, filed on Mar. 2, 2016, which published as US 2018/0074406 A1 on Mar. 15, 2018.
U.S. Appl. No. 15/560,458, entitled "Resist Composition, Method For Forming Resist Pattern, And Polyphenol Compound Used Therein," filed Sep. 21, 2017, which entered the U.S. national phase from International Application No. PCT/JP2016/056333, filed on Mar. 2, 2016, which published as US 2018/0074402 A1 on Mar. 15, 2018.
U.S. Appl. No. 15/755,972, entitled "Material for Forming Underlayer Film For Lithography, Composition For Forming Underlayer Film For Lithography, Underlayer Film For Lithography And Production Method Thereof, Pattern Forming Method, Resin, And Purification Method," filed Feb. 27, 2018, which entered the U.S. national phase from International Application No. PCT/JP2016/074867, filed on Aug. 25, 2016, which published as US 2019/0041750 A1 on Feb. 7, 2019.
U.S. Appl. No. 15/756,463, entitled "Material For Forming Underlayer Film For Lithography, Composition For Forming Underlayer Film For Lithography, Underlayer Film For Lithography And Production Method Thereof, And Resist Pattern Forming Method," filed Feb. 28, 2018, which entered the U.S. national phase from International Application No. PCT/JP2016/074865, filed on Aug. 25, 2016, which published as US 2018/0246409 A1 on Aug. 30, 2018.

\* cited by examiner

COMPOUND, RESIN, RESIST COMPOSITION OR RADIATION-SENSITIVE COMPOSITION, RESIST PATTERN FORMATION METHOD, METHOD FOR PRODUCING AMORPHOUS FILM, UNDERLAYER FILM FORMING MATERIAL FOR LITHOGRAPHY, COMPOSITION FOR UNDERLAYER FILM FORMATION FOR LITHOGRAPHY, METHOD FOR FORMING CIRCUIT PATTERN, AND PURIFICATION METHOD

CROSS-REFERENCE TO RELATED APPLICATIONS

This application is a U.S. national phase application filed under 35 U.S.C. § 371 of International Application PCT/JP2016/076392, filed on Sep. 8, 2016, designating the United States, which claims priority from Japanese Application Number 2015-178545, filed Sep. 10, 2015.

FIELD OF THE INVENTION

The present invention relates to a compound and a resin having a specific structure. The present invention also relates to a resist composition or a radiation-sensitive composition comprising the compound and/or the resin, and a resist pattern formation method and a method for producing an amorphous film using the composition. The present invention further relates to an underlayer film forming material for lithography comprising the compound and/or the resin, a composition for underlayer film formation for lithography comprising the material, and a resist pattern formation method or a circuit pattern formation method using the composition. Furthermore, the present invention relates to a method for purifying the compound and/or the resin.

BACKGROUND OF THE INVENTION

Conventional typical resist materials are polymer-based resist materials capable of forming amorphous thin films. Examples include polymer-based resist materials such as polymethyl methacrylate, polyhydroxy styrene with an acid dissociation reactive group, and polyalkyl methacrylate. A line pattern of about 45 to 100 nm is formed by irradiating a resist thin film made by coating a substrate with a solution of such a polymer-based resist material with ultraviolet, far ultraviolet, electron beam, extreme ultraviolet (EUV), and X-ray or the like.

However, because polymer-based resist materials have a molecular weight as large as about 10,000 to 100,000 and also wide molecular weight distribution, in lithography using a polymer-based resist material, roughness occurs on a fine pattern surface; the pattern dimension becomes difficult to be controlled; and the yield decreases. Therefore, there is a limitation in miniaturization with lithography using a conventional polymer-based resist material. For cutting-edge semiconductor production, various low molecular weight resist materials have been proposed so far as resist base materials for providing resist patterns having higher resolution. The low molecular weight resist materials are expected to provide resist patterns having a small molecular size, high resolution, and small roughness, because of their low molecular weights.

For example, an alkaline development type negative type radiation-sensitive composition (see, for example, Patent Literature 1 (Japanese Patent Application Laid-Open No. 2005-326838) and Patent Literature 2 (Japanese Patent Application Laid-Open No. 2008-145539)) using a low molecular weight polynuclear polyphenolic compound as a main component has been suggested; and as a candidate of a low molecular weight resist material having high heat resistance, an alkaline development type negative type radiation-sensitive composition (see, for example, Patent Literature 3 (Japanese Patent Application Laid-Open No. 2009-173623) and Non Patent Literature 1 (T. Nakayama, M. Nomura, K. Haga, M. Ueda: Bull. Chem. Soc. Jpn., 71, 2979 (1998))) using a low molecular weight cyclic polyphenolic compound as a main component has been suggested as well.

Also, as a base compound of a resist material, a polyphenol compound is known to be capable of imparting high heat resistance despite a low molecular weight and useful for improving the resolution and roughness of a resist pattern (see, for example, Non Patent Literature 2 (Shinji Okazaki et al., "New Trends of Photoresists", CMC Publishing Co., Ltd., September 2009, pp. 211-259). Also, various polyphenols are used as raw materials of thermoplastic resins such as polycarbonate and polyarylate, raw materials of thermosetting resins such as epoxy resins, curing agents, modifiers, and the like (see, for example, Patent Literature 4 (Japanese Patent Application Laid-Open No. 2006-213634) to Patent Literature 5 (Japanese Patent Application Laid-Open No. 2007-326847)).

Moreover, as resin raw materials and resin curing agents, fluorene compounds with a cardo structure that have various improved properties (such as optical properties, heat resistance, water resistance, moisture resistance, chemical resistance, electrical properties, mechanical properties, and dimensional stability) due to substitution with polyhydroxyphenol or the like are known (see, for example, Patent Literature 6 (Japanese Patent Application Laid-Open No. 2006-36648), Patent Literature 7 (Japanese Patent Application Laid-Open No. 2009-155256), Patent Literature 8 (Japanese Patent Application Laid-Open No. 2011-68624), and Patent Literature 9 (Japanese Patent Application Laid-Open No. 2011-105887)).

In lithography upon producing semiconductors, LCD, or solar cells, a photosensitizing agent having a quinonediazide group, such as a naphthoquinonediazide compound, and an alkali soluble resin are used. Positive type photoresists having such composition exhibit high resolving power by development with an alkaline solution and are used in the production of semiconductors such as IC and LSI or the production of circuit base materials such as LCD.

For example, an alkaline development type chemical amplification positive type radiation-sensitive composition (see for example, Patent Literature 10 (Japanese Patent Application Laid-Open No. 2005-266741)) using a low molecular weight polynuclear polyphenolic compound as a main component, and an alkaline development type chemical amplification positive type radiation-sensitive composition (see for example, Patent Literature 11 (Japanese Patent Application Laid-Open No. 2012-83731)) using a low molecular weight cyclic polyphenolic compound as a main component have been suggested.

Meanwhile, in the production of semiconductor devices, fine processing is practiced by lithography using photoresist materials. In recent years, further miniaturization based on pattern rules has been demanded along with increase in the integration and speed of LSI. Lithography using light exposure, which is currently used as a general purpose technique, is approaching the limit of essential resolution derived from the wavelength of a light source.

The light source for lithography used upon forming resist patterns has been shifted to ArF excimer laser (193 nm) having a shorter wavelength from KrF excimer laser (248 nm). However, as the miniaturization of resist patterns proceeds, the problem of resolution or the problem of collapse of resist patterns after development arises. Therefore, resists have been desired to have a thinner film. However, if resists merely have a thinner film, it is difficult to obtain the film thicknesses of resist patterns sufficient for substrate processing. Therefore, there has been a need for a process of preparing a resist underlayer film between a resist and a semiconductor substrate to be processed, and imparting functions as a mask for substrate processing to this resist underlayer film in addition to a resist pattern.

Various resist underlayer films for such a process are currently known. For example, in order to achieve a resist underlayer film for lithography having the selectivity of a dry etching rate close to that of resists, unlike conventional resist underlayer films having a fast etching rate, an underlayer film forming material for a multilayer resist process containing a resin component having at least a substituent that generates a sulfonic acid residue by eliminating a terminal group under application of predetermined energy, and a solvent has been suggested (see Patent Literature 12 (Japanese Patent Application Laid-Open No. 2004-177668)). Also, in order to achieve a resist underlayer film for lithography having the selectivity of a dry etching rate smaller than that of resists, a resist underlayer film material comprising a polymer having a specific repeat unit has been suggested (see Patent Literature 13 (Japanese Patent Application Laid-Open No. 2004-271838)). Furthermore, in order to achieve a resist underlayer film for lithography having the selectivity of a dry etching rate smaller than that of semiconductor substrates, a resist underlayer film material comprising a polymer prepared by copolymerizing a repeat unit of an acenaphthylene and a repeat unit having a substituted or unsubstituted hydroxy group has been suggested (see Patent Literature 14 (Japanese Patent Application Laid-Open No. 2005-250434)).

Meanwhile, as materials having high etching resistance for this kind of resist underlayer film, amorphous carbon underlayer films formed by CVD using methane gas, ethane gas, acetylene gas, or the like as a raw material are well known. However, resist underlayer film materials that can form resist underlayer films by a wet process such as spin coating or screen printing have been demanded from the viewpoint of a process.

The present inventors have proposed an underlayer film forming composition for lithography containing a naphthalene formaldehyde polymer comprising a specific constituent unit, and an organic solvent (see Patent Literature 15 (International Publication No. WO 2009/072465) and Patent Literature 16 (International Publication No. WO 2011/034062)) as a material that is excellent in optical properties and etching resistance and is also soluble in a solvent and applicable to a wet process.

As for methods for forming an intermediate layer used in the formation of a resist underlayer film in a three-layer process, for example, a method for forming a silicon nitride film (see Patent Literature 17 (Japanese Patent Application Laid-Open No. 2002-334869)) and a CVD formation method for a silicon nitride film (see Patent Literature 18 (International Publication No. WO 2004/066377)) are known. Also, as intermediate layer materials for a three-layer process, materials comprising a silsesquioxane-based silicon compound are known (see Patent Literature 19 (Japanese Patent Application Laid-Open No. 2007-226170) and Patent Literature 20 (Japanese Patent Application Laid-Open No. 2007-226204)).

CITATION LIST

Patent Literature

Patent Literature 1: Japanese Patent Application Laid-Open No. 2005-326838
Patent Literature 2: Japanese Patent Application Laid-Open No. 2008-145539
Patent Literature 3: Japanese Patent Application Laid-Open No. 2009-173623
Patent Literature 4: Japanese Patent Application Laid-Open No. 2006-213634
Patent Literature 5: Japanese Patent Application Laid-Open No. 2007-326847
Patent Literature 6: Japanese Patent Application Laid-Open No. 2006-36648
Patent Literature 7: Japanese Patent Application Laid-Open No. 2009-155256
Patent Literature 8: Japanese Patent Application Laid-Open No. 2011-68624
Patent Literature 9: Japanese Patent Application Laid-Open No. 2011-105887
Patent Literature 10: Japanese Patent Application Laid-Open No. 2005-266741
Patent Literature 11: Japanese Patent Application Laid-Open No. 2012-83731
Patent Literature 12: Japanese Patent Application Laid-Open No. 2004-177668
Patent Literature 13: Japanese Patent Application Laid-Open No. 2004-271838
Patent Literature 14: Japanese Patent Application Laid-Open No. 2005-250434
Patent Literature 15: International Publication No. WO 2009/072465
Patent Literature 16: International Publication No. WO 2011/034062
Patent Literature 17: Japanese Patent Application Laid-Open No. 2002-334869
Patent Literature 18: International Publication No. WO 2004/066377
Patent Literature 19: Japanese Patent Application Laid-Open No. 2007-226170
Patent Literature 20: Japanese Patent Application Laid-Open No. 2007-226204

Non Patent Literature

Non Patent Literature 1: T. Nakayama, M. Nomura, K. Haga, M. Ueda: Bull. Chem. Soc. Jpn., 71, 2979 (1998)
Non Patent Literature 2: Shinji Okazaki et al., "New Trends of Photoresists", CMC Publishing Co., Ltd., September 2009, pp. 211-259

SUMMARY OF INVENTION

However, the heat resistances of the compositions of Patent Literatures 1 and 2 are not sufficient, and the shapes of the obtained resist patterns are likely to be poor. The solubility of the compositions of Patent Literature 3 and Non Patent Literature 1 in safe solvents used in a semiconductor production process is not sufficient, also their sensitivity is not sufficient, and the shapes of the obtained resist patterns are poor in some cases. Thus, a further improvement of low molecular weight resist materials is desired.

Also, Patent Literatures 4 and 5 and Non Patent Literature 2 are silent on solubility, and the heat resistances of the described compounds are still not sufficient. Thus, a further improvement of various properties such as heat resistance, water resistance, chemical resistance, electrical properties, and mechanical properties is required.

Furthermore, properties such as heat resistance of the alcohol compounds of Patent Literatures 6 to 9 are not sufficient. Thus, an alcohol compound having more improved heat resistance is desired.

Moreover, resist patterns formed from the compositions described in Patent Literatures 10 and 11 have large roughness. Thus, a further improvement of radiation-sensitive compositions is required.

As mentioned above, a large number of underlayer film forming materials for lithography have heretofore been suggested. However, none of these materials not only have high solvent solubility that permits application of a wet process such as spin coating or screen printing but achieve both of heat resistance and etching resistance at high dimensions. Thus, the development of novel materials is required.

An object of the present invention is to provide a compound having high solubility in a safe solvent and high heat resistance and a resin comprising the compound as a constituent. Another object of the present invention is to provide a resist composition that can impart a shape to a resist pattern, a radiation-sensitive composition that provides a good resist pattern with small roughness, and a resist pattern formation method and a method for producing an amorphous film using the composition.

A further object of the present invention is to provide an underlayer film forming material for lithography that is applicable to a wet process and is useful for forming a photoresist underlayer film excellent in heat resistance and etching resistance, a composition for underlayer film formation for lithography, and pattern formation methods (a resist pattern formation method and a circuit pattern formation method) using the material.

The present invention can further provide a purification method suitable for the above compound or resin.

The inventors have, as a result of devoted examinations to solve the above problems, found out that use of a compound or a resin having a specific structure can solve the above problems, and reached the present invention.

More specifically, the present invention is as follows.
<1> A compound represented by the following formula (1):

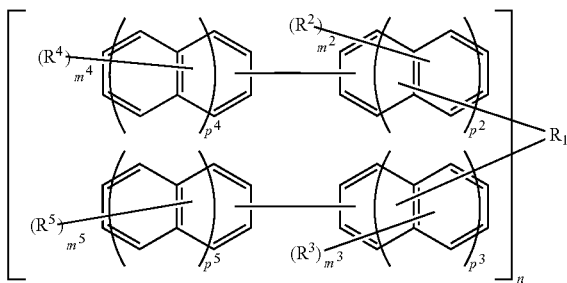

(1)

wherein $R^1$ is a 2n-valent group of 1 to 60 carbon atoms or a single bond; $R^2$ to $R^5$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, a hydroxy group, or a group in which a hydrogen atom of a hydroxy group is replaced with an acid dissociation group, provided that at least one selected from $R^2$ to $R^5$ is a group in which a hydrogen atom of a hydroxy group is replaced with an acid dissociation group; $m^2$ and $m^3$ are each independently an integer of 0 to 8; $m^4$ and $m^5$ are each independently an integer of 0 to 9, provided that $m^2$, $m^3$, $m^4$, and $m^5$ are not 0 at the same time; n is an integer of 1 to 4; and $p^2$ to $p^5$ are each independently an integer of 0 to 2.

<2> The compound according to <1>, wherein at least one selected from the group consisting of $R^4$ and $R^5$ is a group in which a hydrogen atom of a hydroxy group is replaced with an acid dissociation group.

<3> The compound according to <1> or <2>, wherein at least one selected from the group consisting of $R^2$ and $R^3$ is a group in which a hydrogen atom of a hydroxy group is replaced with an acid dissociation group.

<4> The compound according to any one of <1> to <3>, wherein at least one selected from the group consisting of $R^1$ to $R^5$ is a group containing an iodine atom.

<5> The compound according to any one of <1> to <4>, wherein the compound represented by the formula (1) is a compound represented by the following formula (1a):

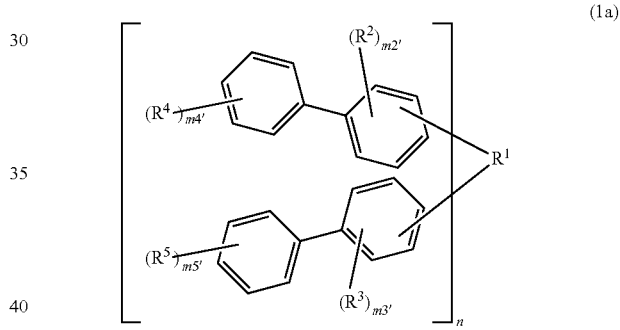

(1a)

wherein $R^1$ to $R^5$ and n are as defined in the description of the formula (1), provided that at least one selected from the group consisting of $R^2$ to $R^5$ is a group in which a hydrogen atom of a hydroxy group is replaced with an acid dissociation group; $m^{2'}$ and $m^{3'}$ are each independently an integer of 0 to 4; and $m^{4'}$ and $m^{5'}$ are each independently an integer of 0 to 5, provided that $m^{2'}$, $m^{3'}$, $m^{4'}$, and $m^{5'}$ are not 0 at the same time.

<6> The compound according to <5>, wherein the compound represented by the formula (1a) is a compound represented by the following formula (1b):

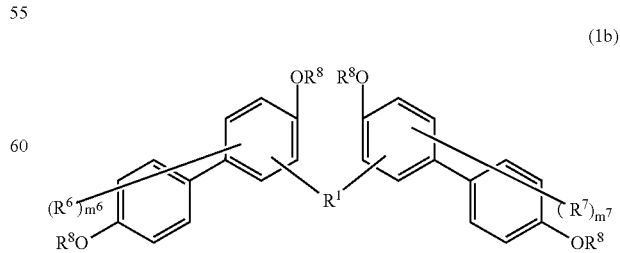

(1b)

wherein $R^1$ is as defined in the description of the formula (1); $R^6$ and $R^7$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, or a thiol group; each $R^8$ is independently a hydrogen atom or an acid dissociation group, provided that at least one $R^8$ is an acid dissociation group; and $m^6$ and $m^7$ are each independently an integer of 0 to 7.

<7> The compound according to <6>, wherein the compound represented by the formula (1b) is a compound represented by the following formula (1c):

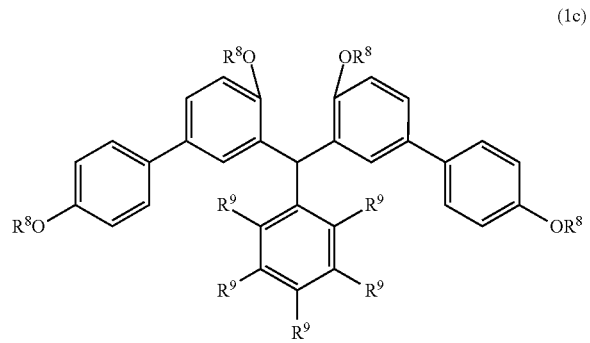

wherein $R^8$ is as defined in the description of the formula (1b); and each $R^9$ is independently a hydrogen atom, a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkoxy group of 1 to 30 carbon atoms, a thiol group, or a hydroxy group, provided that at least one $R^8$ is an acid dissociation group.

<8> The compound according to <7>, wherein the compound represented by the formula (1c) is a compound represented by the following formula (1d):

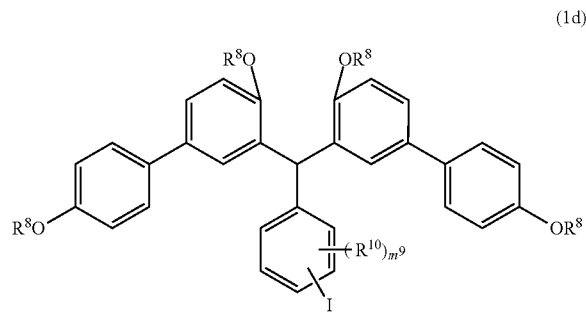

wherein $R^8$ is as defined in the description of the formula (1b); each $R^{10}$ is independently a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkoxy group of 1 to 30 carbon atoms, a thiol group, or a hydroxy group; and $m^9$ is an integer of 0 to 4, provided that at least one $R^8$ is an acid dissociation group.

<9> A resin comprising the compound according to <1> as a constituent.

<10> A resist composition comprising the compound according to any one of <1> to <8> and/or the resin according to <9>.

<11> The resist composition according to <10>, further comprising a solvent.

<12> The resist composition according to <11>, further comprising an acid generating agent.

<13> The resist composition according to <11> or <12>, further comprising an acid diffusion controlling agent.

<14> A method for forming a resist pattern, comprising the steps of: coating a substrate with the resist composition according to any one of <10> to <13>, thereby forming a resist film; exposing the formed resist film; and developing the exposed resist film.

<15> A radiation-sensitive composition comprising the compound according to any one of <1> to <8> and/or the resin according to <9> (A), an optically active diazonaphthoquinone compound (B), and a solvent, wherein the content of the solvent in the composition is 20 to 99% by mass, and the content of components except for the solvent is 1 to 80% by mass.

<16> The radiation-sensitive composition according to <15>, wherein the components except for the solvent include the compound and/or the resin (A)/the optically active diazonaphthoquinone compound (B)/an optional component (D) at 1 to 99/99 to 1/0 to 98% by mass based on the components except for the solvent.

<17> The radiation-sensitive composition according to <15> or <16>, wherein the radiation-sensitive composition is used in the formation of an amorphous film by spin coating.

<18> A method for producing an amorphous film, comprising the step of coating a substrate with the radiation-sensitive composition according to any one of <15> to <17>.

<19> A method for forming a resist pattern, comprising the steps of: coating a substrate with the radiation-sensitive composition according to any one of <15> to <17>, thereby forming a resist film; exposing the resist film; and developing the exposed resist film.

<20> An underlayer film forming material for lithography comprising the compound according to any one of <1> to <8> and/or the resin according to <9>.

<21> A composition for underlayer film formation for lithography comprising the underlayer film forming material for lithography according to <20>, and a solvent.

<22> The composition for underlayer film formation for lithography according to <21>, further comprising an acid generating agent.

<23> The composition for underlayer film formation for lithography according to <21> or <22>, further comprising a crosslinking agent.

<24> A method for producing an underlayer film for lithography, comprising the step of forming an underlayer film on a substrate using the composition for underlayer film formation for lithography according to any one of <21> to <23>.

<25> A method for forming a resist pattern, comprising the steps of: forming an underlayer film on a substrate using the composition for underlayer film formation for lithography according to any one of <21> to <23>; forming at least one photoresist layer on the underlayer film; and then irradiating a predetermined region of the photoresist layer with radiation for development.

<26> A method for forming a circuit pattern, comprising: forming an underlayer film on a substrate using the composition for underlayer film formation for lithography according to any one of <21> to <23>; forming an intermediate layer film on the underlayer film using a resist intermediate layer film material containing a silicon atom; forming at least one photoresist layer on the intermediate layer film; then irradiating a predetermined region of the photoresist layer with radiation for development, thereby forming a resist pattern; and then etching the intermediate layer film with the resist pattern as a mask, etching the underlayer film with the obtained intermediate layer film pattern as an etching mask, and etching the substrate with the obtained underlayer film pattern as an etching mask, thereby forming a pattern on the substrate.

<27> A purification method comprising the steps of:
obtaining a solution (S) by dissolving the compound according to any one of <1> to <8> and/or the resin according to <9> in a solvent; and
extracting impurities in the compound and/or the resin by bringing the obtained solution (S) into contact with an acidic aqueous solution (a first extraction step), wherein
the solvent used in the step of obtaining the solution (S) comprises a solvent that does not inadvertently mix with water.

<28> The purification method according to <27>, wherein
the acidic aqueous solution is an aqueous mineral acid solution or an aqueous organic acid solution;
the aqueous mineral acid solution is one or more aqueous mineral acid solutions selected from the group consisting of hydrochloric acid, sulfuric acid, nitric acid, and phosphoric acid; and
the aqueous organic acid solution is one or more aqueous organic acid solutions selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid.

<29> The purification method according to <27> or <28>, wherein the solvent that does not inadvertently mix with water is one or more solvents selected from the group consisting of toluene, 2-heptanone, cyclohexanone, cyclopentanone, methyl isobutyl ketone, propylene glycol monomethyl ether acetate, and ethyl acetate.

<30> The purification method according to any one of <27> to <29>, comprising the step of extracting impurities in the compound by further bringing a solution phase comprising the compound into contact with water after the first extraction step (a second extraction step).

The present invention can provide a compound having high solubility in a safe solvent and high heat resistance and a resin comprising the compound as a constituent. The present invention can also provide a resist composition that can impart a shape to a resist pattern, a radiation-sensitive composition that provides a good resist pattern with small roughness, and a resist pattern formation method and a method for producing an amorphous film using the composition.

The present invention can further provide an underlayer film forming material for lithography that is applicable to a wet process and is useful for forming a photoresist underlayer film excellent in heat resistance and etching resistance, a composition for underlayer film formation for lithography, and pattern formation methods (a resist pattern formation method and a circuit pattern formation method) using the material.

The present invention can further provide a purification method suitable for the above compound or resin.

DESCRIPTION OF EMBODIMENTS

Hereinafter, embodiments of the present invention will be described. The embodiments described below are given merely for illustrating the present invention. The present invention is not limited only by these embodiments.

[Compound]

The compound of the present embodiment is represented by the following formula (1):

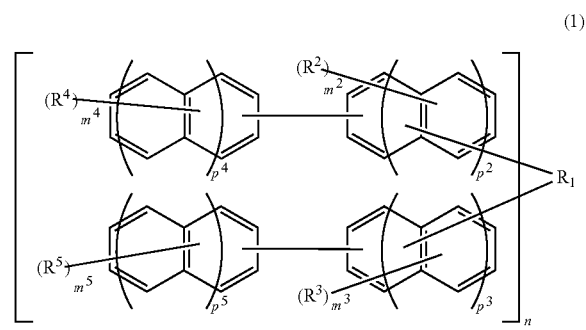

In the above formula (1), $R^1$ is a 2n-valent group of 1 to 60 carbon atoms or a single bond, and each aromatic ring is bonded via this $R^1$. The 2n-valent group refers to, for example, an alkylene group of 1 to 60 carbon atoms when n is 1, an alkanetetrayl group of 1 to 60 carbon atoms when n is 2, an alkanehexayl group of 2 to 60 carbon atoms when n is 3, and an alkaneoctayl group of 3 to 60 carbon atoms when n is 4. Examples of the 2n-valent group include linear hydrocarbon groups, branched hydrocarbon groups, and alicyclic hydrocarbon groups. Herein, an alicyclic hydrocarbon group also includes bridged alicyclic hydrocarbon groups.

Also, the 2n-valent group may have a double bond, a heteroatom, a heterocyclic group, or an aromatic group of 6 to 30 carbon atoms. Furthermore, the heterocyclic group may have a cyano group, a nitro group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkoxy group of 1 to 30 carbon atoms, a thiol group, a hydroxy group, or a group in which a hydrogen atom of a hydroxy group is replaced with an acid dissociation group. Also, the aromatic group may have a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkoxy group of 1 to 30 carbon atoms, a thiol group, a hydroxy group, or a group in which a hydrogen atom of a hydroxy group is replaced with an acid dissociation group.

$R^2$ to $R^5$ are each independently a group selected from the group consisting of a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, a hydroxy group, and a group in which a hydrogen atom of a hydroxy group is replaced with an acid dissociation group.

The alkenyl group and the alkoxy group may have a linear, branched, or cyclic structure. In the compound represented by the formula (1), at least one selected from the group consisting of $R^4$ and $R^5$ is preferably a group in which a hydrogen atom of a hydroxy group is replaced with an acid dissociation group. Also, at least one selected from the group consisting of $R^2$ and $R^3$ may be a group in which a hydrogen atom of a hydroxy group is replaced with an acid dissociation group.

However, at least one selected from the $R^2$ to the $R^5$ is a group in which a hydrogen atom of a hydroxy group is replaced with an acid dissociation group.

In the present specification, the "at least one selected from $R^2$ to $R^5$" means "at least one group selected from $R^2$ to $R^5$", and does not mean "at least one kind of group selected from $R^2$ to $R^5$".

$m^2$ and $m^3$ are each independently an integer of 0 to 8. $m^4$ and $m^5$ are each independently an integer of 0 to 9. However, $m^2$, $m^3$, $m^4$, and $m^5$ are not 0 at the same time. n is an integer of 1 to 4. $p^2$ to $p^5$ are each independently an integer of 0 to 2. The site represented by the naphthalene structure in the formula (1) refers to a benzene structure when p is 0, a naphthalene structure when p is 1, and a tricyclic structure such as anthracene or phenanthrene when p is 2.

In the present specification, the "acid dissociation group" refers to a characteristic group that is cleaved in the presence of an acid to cause a change such as an alkali soluble group. Examples of the alkali soluble group include, but not particularly limited to, a phenolic hydroxy group, a carboxyl group, a sulfonic acid group, and a hexafluoroisopropanol group. A phenolic hydroxy group and a carboxyl group are preferable, and a phenolic hydroxy group is particularly preferable. The acid dissociation group is not particularly limited, but can be arbitrarily selected and used from among, for example, those proposed in hydroxystyrene-based resins, (meth)acrylic acid-based resins, and the like for use in chemically amplified resist compositions for KrF or ArF. Specific examples thereof include, but not particularly limited to, a substituted methyl group, a 1-substituted ethyl group, a 1-substituted n-propyl group, a 1-branched alkyl group, a silyl group, an acyl group, a 1-substituted alkoxymethyl group, a cyclic ether group, an alkoxycarbonyl group, and an alkoxycarbonylalkyl group. It is preferable that the acid dissociation group should have no crosslinkable functional group.

Examples of the substituted methyl group include, but not particularly limited to, a substituted methyl group of 2 to 20 carbon atoms. A substituted methyl group of 4 to 18 carbon atoms is preferable, and a substituted methyl group of 6 to 16 carbon atoms is more preferable. Specific examples thereof can include, but not particularly limited to, a methoxymethyl group, a methylthiomethyl group, an ethoxymethyl group, a n-propoxymethyl group, an iso-propoxymethyl group, a n-butoxymethyl group, a t-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formula (13-1). Examples of $R^{2'}$ in the following formula (13-1) include, but not particularly limited to, a methyl group, an ethyl group, an isopropyl group, a n-propyl group, a t-butyl group, and a n-butyl group.

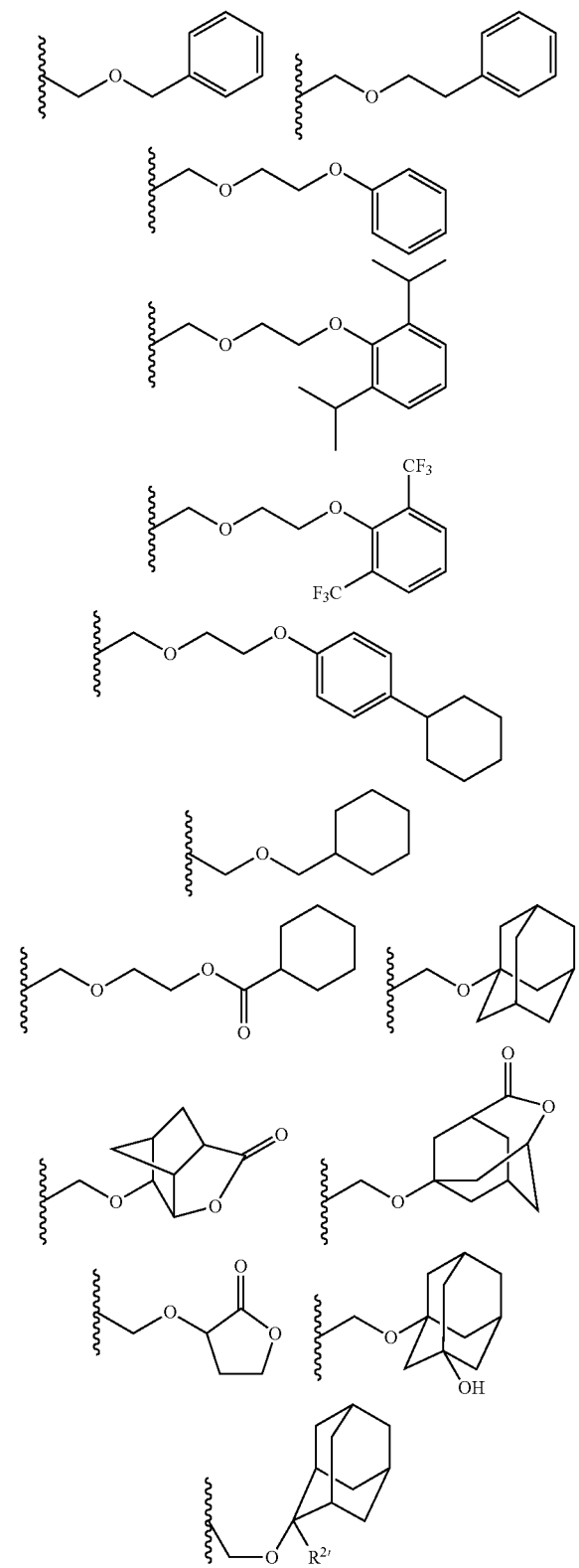

(13-1)

wherein $R^{2'}$ is an alkyl group of 1 to 4 carbon atoms.

Examples of the 1-substituted ethyl group include, but not particularly limited to, a 1-substituted ethyl group of 3 to 20 carbon atoms. A 1-substituted ethyl group of 5 to 18 carbon atoms is preferable, and a substituted ethyl group of 7 to 16 carbon atoms is more preferable. Specific examples thereof can include, but not particularly limited to, a 1-methoxyethyl group, 1-methylthioethyl group, a 1,1-dimethoxyethyl group, a 1-ethoxyethyl group, a 1-ethylthioethyl group, a 1,1-diethoxyethyl group, a n-propoxyethyl group, an isopropoxyethyl group, a n-butoxyethyl group, a t-butoxyethyl group, a 2-methylpropoxyethyl group, a 1-phenoxyethyl group, a 1-phenylthioethyl group, a 1,1-diphenoxyethyl group, a 1-cyclopentyloxyethyl group, a 1-cyclohexyloxyethyl group, a 1-phenylethyl group, a 1,1-diphenylethyl group, and a substituent represented by the following formula (13-2):

(13-2)

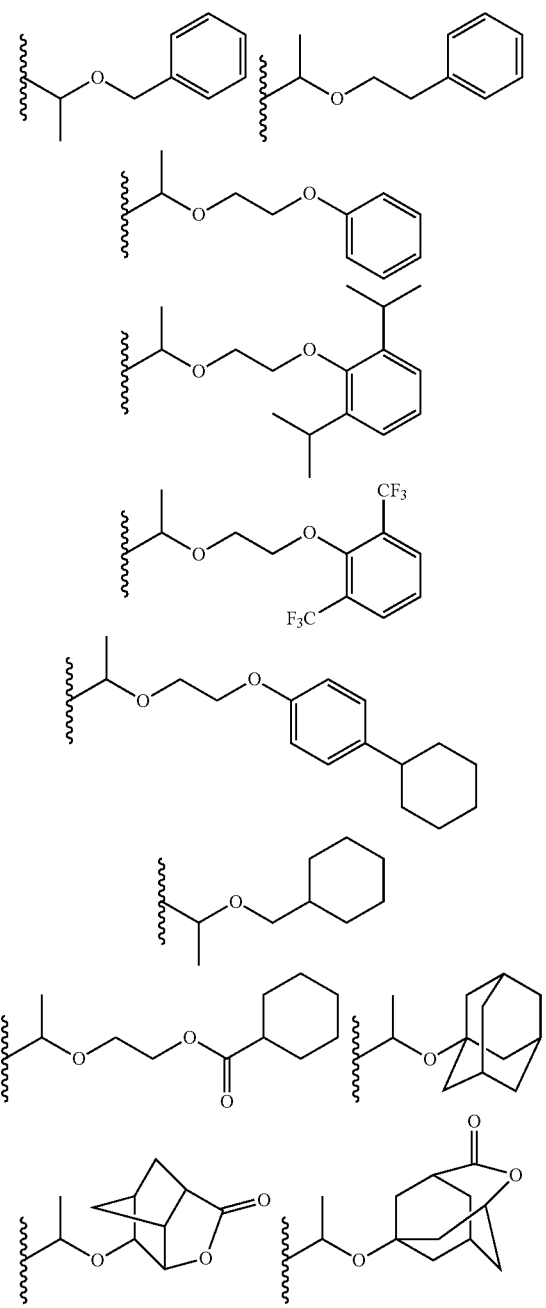

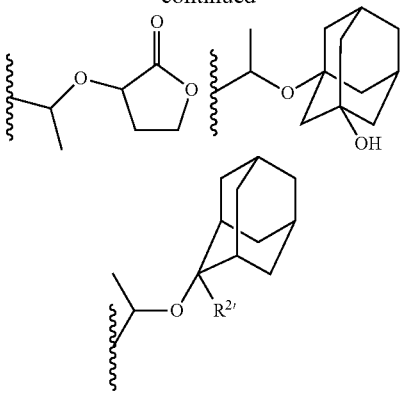

wherein $R^{2'}$ is as defined in the above formula (13-1).

Examples of the 1-substituted n-propyl group include, but not particularly limited to, a 1-substituted n-propyl group of 4 to 20 carbon atoms. A 1-substituted n-propyl group of 6 to 18 carbon atoms is preferable, and a 1-substituted n-propyl group of 8 to 16 carbon atoms is more preferable. Specific examples thereof can include, but not particularly limited to, a 1-methoxy-n-propyl group and a 1-ethoxy-n-propyl group.

Examples of the 1-branched alkyl group include, but not particularly limited to, a 1-branched alkyl group of 3 to 20 carbon atoms. A 1-branched alkyl group of 5 to 18 carbon atoms is preferable, and a branched alkyl group of 7 to 16 carbon atoms is more preferable. Specific examples thereof can include, but not particularly limited to, an isopropyl group, a sec-butyl group, a tert-butyl group, a 1,1-dimethylpropyl group, a 1-methylbutyl group, a 1,1-dimethylbutyl group, a 2-methyladamantyl group, and a 2-ethyladamantyl group.

Examples of the silyl group include, but not particularly limited to, a silyl group of 1 to 20 carbon atoms. A silyl group of 3 to 18 carbon atoms is preferable, and a silyl group of 5 to 16 carbon atoms is more preferable. Specific examples thereof can include, but not particularly limited to, a trimethylsilyl group, an ethyldimethylsilyl group, a methyldiethylsilyl group, a triethylsilyl group, a tert-butyldimethylsilyl group, a tert-butyldiethylsilyl group, a tert-butyldiphenylsilyl group, a tri-tert-butylsilyl group, and a triphenylsilyl group.

Examples of the acyl group include, but not particularly limited to, an acyl group of 2 to 20 carbon atoms. An acyl group of 4 to 18 carbon atoms is preferable, and an acyl group of 6 to 16 carbon atoms is more preferable. Specific examples thereof can include, but not particularly limited to, an acetyl group, a phenoxyacetyl group, a propionyl group, a butyryl group, a heptanoyl group, a hexanoyl group, a valeryl group, a pivaloyl group, an isovaleryl group, a lauroyl group, an adamantylcarbonyl group, a benzoyl group, and a naphthoyl group.

Examples of the 1-substituted alkoxymethyl group include, but not particularly limited to, a 1-substituted alkoxymethyl group of 2 to 20 carbon atoms. A 1-substituted alkoxymethyl group of 4 to 18 carbon atoms is preferable, and a 1-substituted alkoxymethyl group of 6 to 16 carbon atoms is more preferable. Specific examples thereof can include, but not particularly limited to, a 1-cyclopentylmethoxymethyl group, a 1-cyclopentylethoxymethyl group, a 1-cyclohexylmethoxymethyl group, a 1-cyclohexylethoxymethyl group, a 1-cyclooctylmethoxymethyl group, and a 1-adamantylmethoxymethyl group.

Examples of the cyclic ether group include, but not particularly limited to, a cyclic ether group of 2 to 20 carbon atoms. A cyclic ether group of 4 to 18 carbon atoms is preferable, and a cyclic ether group of 6 to 16 carbon atoms is more preferable. Specific examples thereof can include, but not particularly limited to, a tetrahydropyranyl group, a tetrahydrofuranyl group, a tetrahydrothiopyranyl group, a tetrahydrothiofuranyl group, a 4-methoxytetrahydropyranyl group, and a 4-methoxytetrahydrothiopyranyl group.

Examples of the alkoxycarbonyl group include, but not particularly limited to, an alkoxycarbonyl group of 2 to 20 carbon atoms. An alkoxycarbonyl group of 4 to 18 carbon atoms is preferable, and an alkoxycarbonyl group of 6 to 16 carbon atoms is more preferable. Specific examples thereof can include, but not particularly limited to, a methoxycarbonyl group, an ethoxycarbonyl group, a n-propoxycarbonyl group, an isopropoxycarbonyl group, a n-butoxycarbonyl group, a tert-butoxycarbonyl group, and an acid dissociation group represented by the following formula (13-3) wherein n is 0.

Examples of the alkoxycarbonylalkyl group include, but not particularly limited to, an alkoxycarbonylalkyl group of 2 to 20 carbon atoms. An alkoxycarbonylalkyl group of 4 to 18 carbon atoms is preferable, and an alkoxycarbonylalkyl group of 6 to 16 carbon atoms is more preferable. Specific examples thereof can include, but not particularly limited to, a methoxycarbonylmethyl group, an ethoxycarbonylmethyl group, a n-propoxycarbonylmethyl group, an isopropoxycarbonylmethyl group, a n-butoxycarbonylmethyl group, and an acid dissociation group represented by the following formula (13-3) wherein n is 1 to 4:

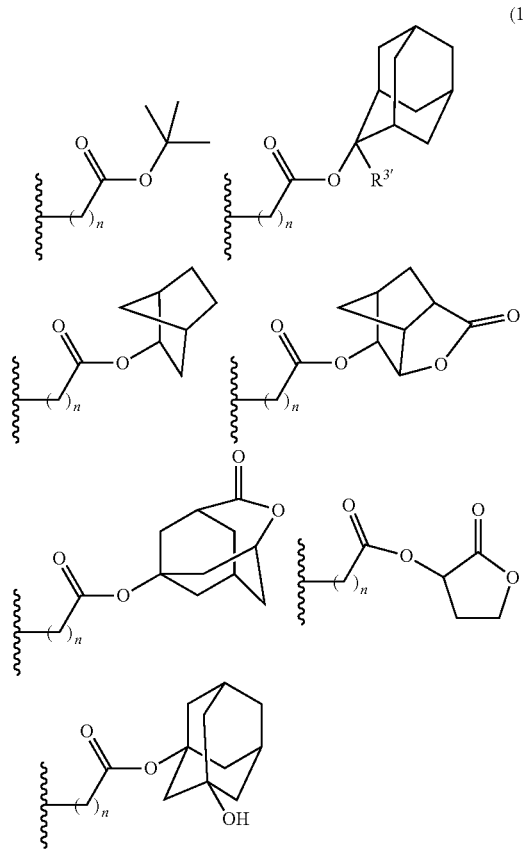

(13-3)

wherein $R^{3'}$ is a hydrogen atom or a linear or branched alkyl group of 1 to 4 carbon atoms; and n is an integer of 0 to 4.

Among these acid dissociation groups, a substituted methyl group, a 1-substituted ethyl group, a 1-substituted alkoxymethyl group, a cyclic ether group, an alkoxycarbonyl group, and an alkoxycarbonylalkyl group are preferable, a substituted methyl group, a 1-substituted ethyl group, an alkoxycarbonyl group, and an alkoxycarbonylalkyl group are more preferable because of high sensitivity, and an acid dissociation group having a structure selected from a cycloalkane of 3 to 12 carbon atoms, a lactone, and an aromatic ring of 6 to 12 carbon atoms is further preferable. The cycloalkane of 3 to 12 carbon atoms may be monocyclic or polycyclic and is preferably polycyclic. Specific examples thereof include, but not particularly limited to, monocycloalkanes, bicycloalkanes, tricycloalkanes, and tetracycloalkanes. More specific examples thereof include, but not particularly limited to: monocycloalkanes such as cyclopropane, cyclobutane, cyclopentane, and cyclohexane; and polycycloalkanes such as adamantane, norbornane, isobornane, tricyclodecane, and tetracyclodecane. Among them, adamantane, tricyclodecane, and tetracyclodecane are preferable, and adamantane and tricyclodecane are particularly preferable. The cycloalkane of 3 to 12 carbon atoms may have a substituent. Examples of the lactone include, but not particularly limited to, cycloalkane groups of 3 to 12 carbon atoms having a butyrolactone or lactone group. Examples of the aromatic ring of 6 to 12 carbon atoms include, but not particularly limited to, a benzene ring, a naphthalene ring, an anthracene ring, a phenanthrene ring, and a pyrene ring. A benzene ring and a naphthalene ring are preferable, and a naphthalene ring is particularly preferable.

Particularly, an acid dissociation group selected from the group consisting of groups represented by the following formula (13-4) is preferable because of high resolution:

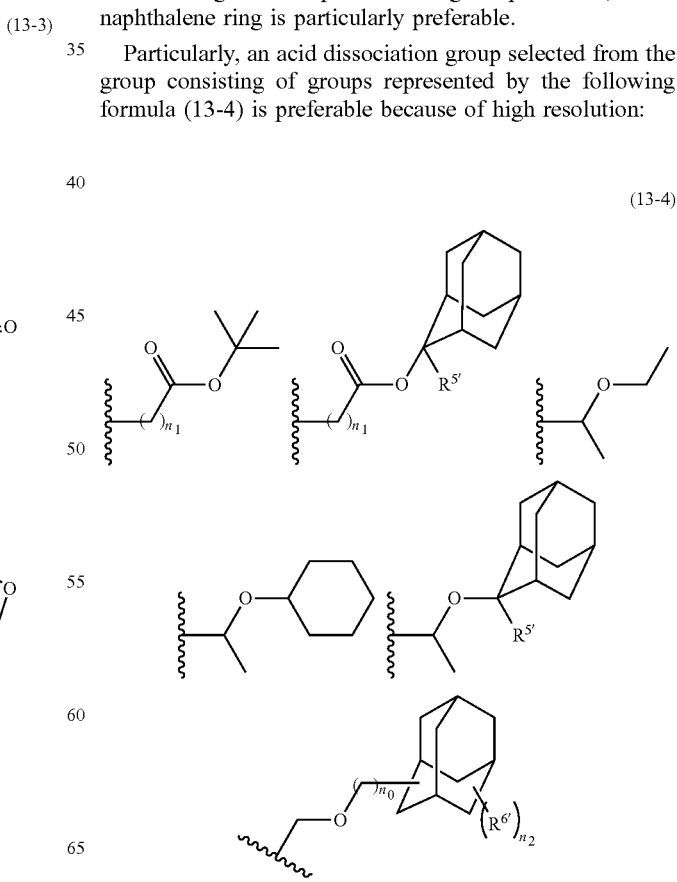

(13-4)

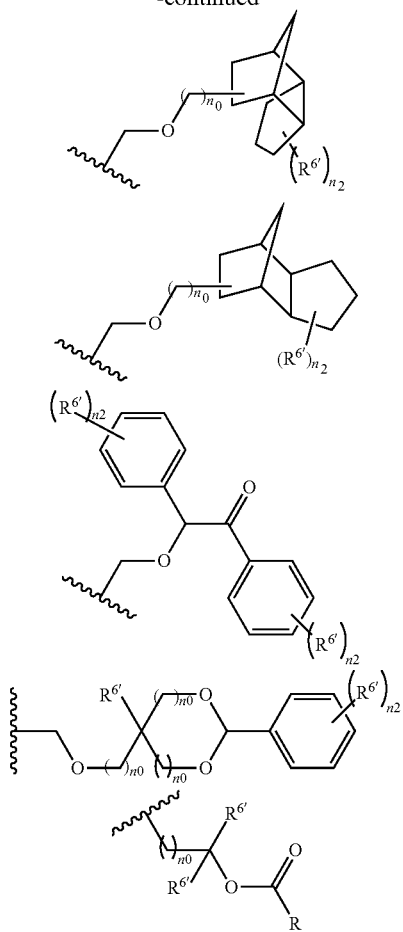

wherein R⁵' is a hydrogen atom or a linear or branched alkyl group of 1 to 4 carbon atoms; R⁶' is a hydrogen atom, a linear or branched alkyl group of 1 to 4 carbon atoms, a cyano group, a nitro group, a heterocyclic group, a halogen atom, or a carboxyl group; $n_1$ is an integer of 0 to 4; $n_2$ is an integer of 1 to 5; and $n_0$ is an integer of 0 to 4.

In the compound represented by the above formula (1), at least one selected from the group consisting of $R^1$ to $R^5$ in the formula (1) is preferably a group containing an iodine atom, from the viewpoint of sensitivity upon exposure.

The "at least one selected from the group consisting of $R^1$ to $R^5$" means "at least one group selected from the group consisting of $R^1$ to $R^5$", and does not mean "at least one kind of group selected from the group consisting of $R^1$ to $R^5$".

Examples of the group containing an iodine atom as to $R^1$ include, but not particularly limited to, a linear hydrocarbon group of 1 to 60 carbon atoms substituted with an iodine atom, a branched hydrocarbon group of 3 to 60 carbon atoms substituted with an iodine atom, an alicyclic hydrocarbon group of 3 to 60 carbon atoms substituted with an iodine atom, a heterocyclic group of 3 to 60 carbon atoms substituted with an iodine atom, a group having a heterocyclic group of 3 to 60 carbon atoms substituted with an iodine atom, an aromatic group of 6 to 60 carbon atoms substituted with an iodine atom, and a group having an aromatic group of 6 to 60 carbon atoms substituted with an iodine atom.

From the viewpoint of heat resistance, a branched hydrocarbon group of 3 to 60 carbon atoms substituted with an iodine atom, an alicyclic hydrocarbon group of 3 to 60 carbon atoms substituted with an iodine atom, a heterocyclic group of 3 to 60 carbon atoms substituted with an iodine atom, a group having a heterocyclic group of 3 to 60 carbon atoms substituted with an iodine atom, an aromatic group of 6 to 60 carbon atoms substituted with an iodine atom, and a group having an aromatic group of 6 to 60 carbon atoms substituted with an iodine atom are preferable, an alicyclic hydrocarbon group of 3 to 60 carbon atoms substituted with an iodine atom, a heterocyclic group of 3 to 60 carbon atoms substituted with an iodine atom, a group having a heterocyclic group of 3 to 60 carbon atoms substituted with an iodine atom, an aromatic group of 6 to 60 carbon atoms substituted with an iodine atom, and a group having an aromatic group of 6 to 60 carbon atoms substituted with an iodine atom are more preferable, and an a group having a heterocyclic group of 3 to 60 carbon atoms substituted with an iodine atom and a group having an aromatic group of 6 to 60 carbon atoms substituted with an iodine atom are further preferable.

Examples of the group containing an iodine atom as to $R^2$ to $R^5$ include, but not particularly limited to, an iodine atom, a linear aliphatic hydrocarbon group of 1 to 6 carbon atoms substituted with an iodine atom, a branched aliphatic hydrocarbon group of 3 to 6 carbon atoms substituted with an iodine atom, a cyclic aliphatic hydrocarbon group of 3 to 6 carbon atoms substituted with an iodine atom, and an aryl group of 6 carbon atoms substituted with an iodine atom. From the viewpoint of solubility in a safe solvent, etc., the group containing an iodine atom is preferably an iodine atom, a linear aliphatic hydrocarbon group of 1 to 6 carbon atoms substituted with an iodine atom, or a branched aliphatic hydrocarbon group of 3 to 6 carbon atoms substituted with an iodine atom, and more preferably an iodine atom or a linear aliphatic hydrocarbon group of 1 to 6 carbon atoms substituted with an iodine atom. An iodine atom is further preferable.

In the compound represented by the above formula (1), at least one selected from $R^4$ and $R^5$ is preferably a group in which a hydrogen atom of a hydroxy group is replaced with an acid dissociation group, and at least one selected from $R^2$ and $R^3$ is more preferably a group in which a hydrogen atom of a hydroxy group is replaced with an acid dissociation group, from the viewpoint of easy crosslinking, further solubility in an organic solvent, and reduction in the defects of a coating film.

The compound represented by the above formula (1) is more preferably a compound represented by the following formula (1a) from the viewpoint of the supply of raw materials:

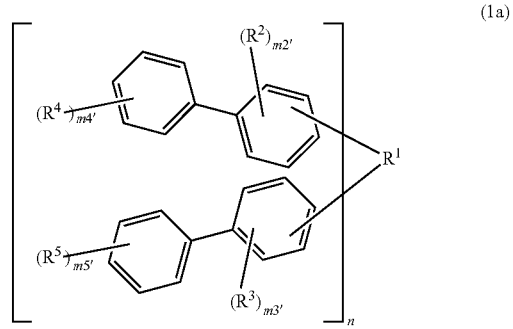

In the formula (1a), $R^1$ to $R^5$ and n are as defined in the description of the above formula (1). However, at least one selected from the group consisting of $R^2$ to $R^5$ is a group in which a hydrogen atom of a hydroxy group is replaced with an acid dissociation group. $m^{2'}$ and $m^{3'}$ are each independently an integer of 0 to 4, and $m^{4'}$ and $m^{5'}$ are each independently an integer of 0 to 5, provided that $m^{2'}$, $m^{3'}$, $m^{4'}$, and $m^{5'}$ are not 0 at the same time.

The compound represented by the above formula (1a) is further preferably a compound represented by the following formula (1b) from the viewpoint of solubility in an organic solvent:

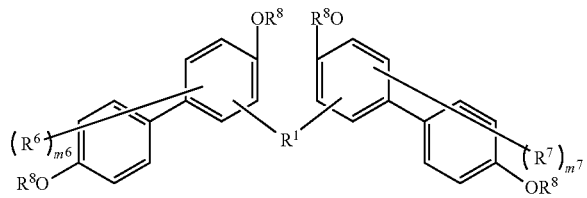
(1b)

In the above formula (1b), $R^1$ is as defined in the description of the above formula (1). $R^6$ and $R^7$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, or a thiol group. Each $R^8$ is independently a hydrogen atom or an acid dissociation group. However, at least one $R^8$ is an acid dissociation group. $m^6$ and $m^7$ are each independently an integer of 0 to 7.

The compound represented by the above formula (1b) is particularly preferably a compound represented by the following formula (1c) from the viewpoint of further solubility in an organic solvent:

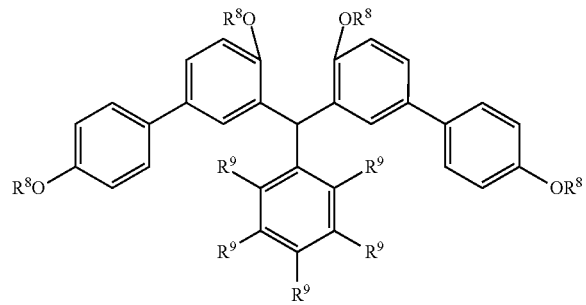
(1c)

In the above formula (1c), each $R^8$ is independently a hydrogen atom or an acid dissociation group. However, at least one $R^8$ is an acid dissociation group. Each $R^9$ is independently a hydrogen atom, a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkoxy group of 1 to 30 carbon atoms, a thiol group, or a hydroxy group from the viewpoint of quality stabilization.

The compound represented by the above formula (1c) is particularly preferably a compound represented by the following formula (1d) from the viewpoint of easy crosslinking, further solubility in an organic solvent, and reduction in the defects of a coating film:

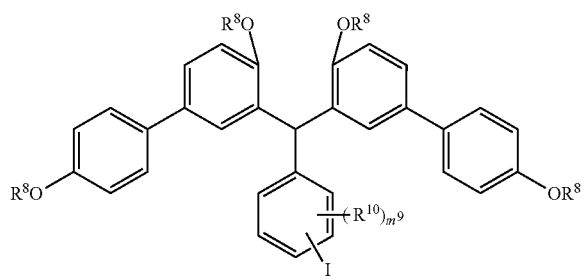
(1d)

In the above formula (1d), each $R^8$ is independently a hydrogen atom or an acid dissociation group. However, at least one $R^8$ is an acid dissociation group. Each $R^{10}$ is independently a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkoxy group of 1 to 30 carbon atoms, a thiol group, or a hydroxy group. $m^9$ is an integer of 0 to 4.

Specific examples of the compound represented by the above formula (1) include, but not limited to, those described below.

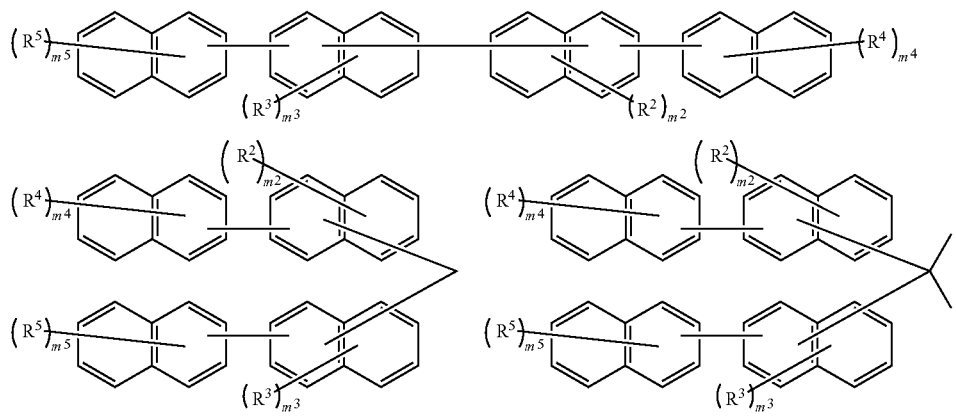

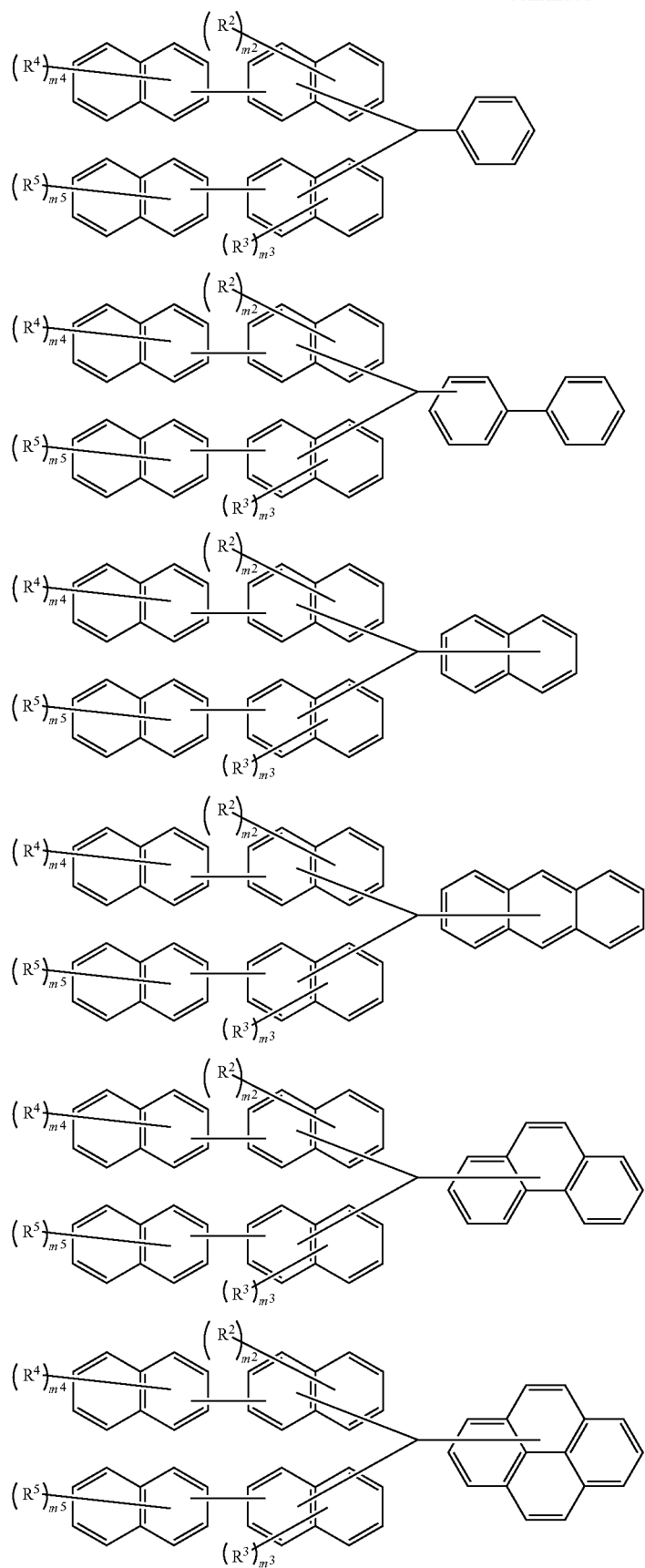

-continued
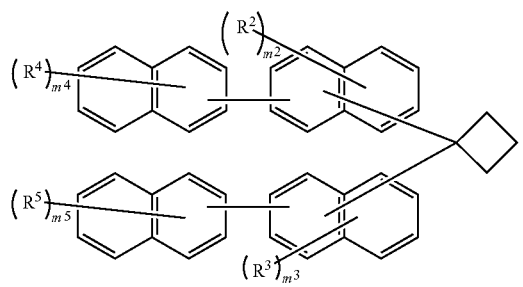
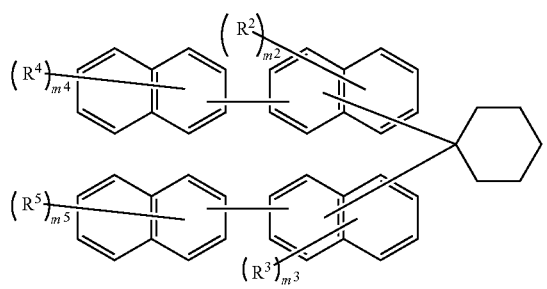
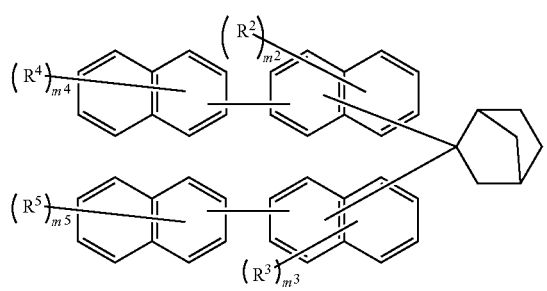
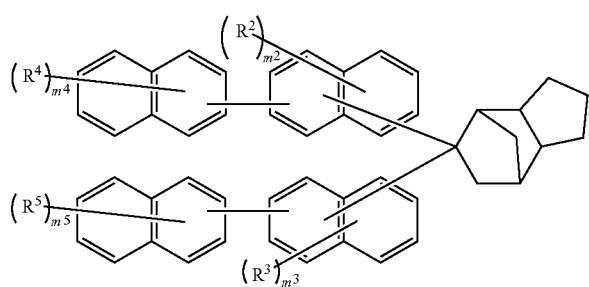
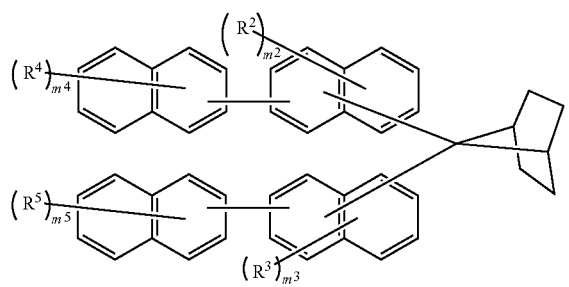
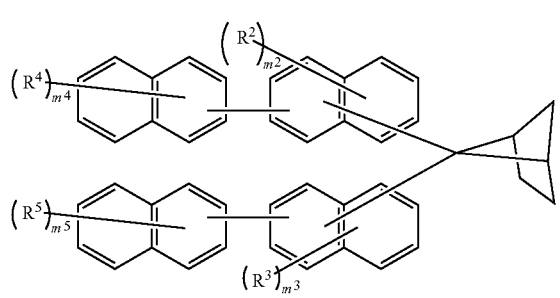
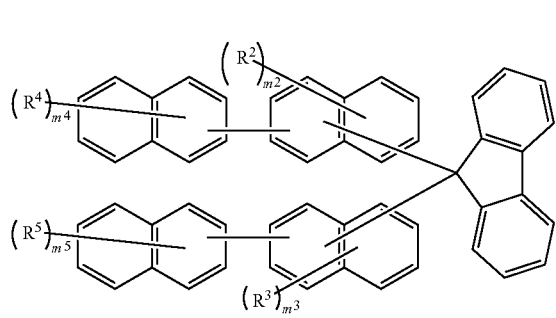
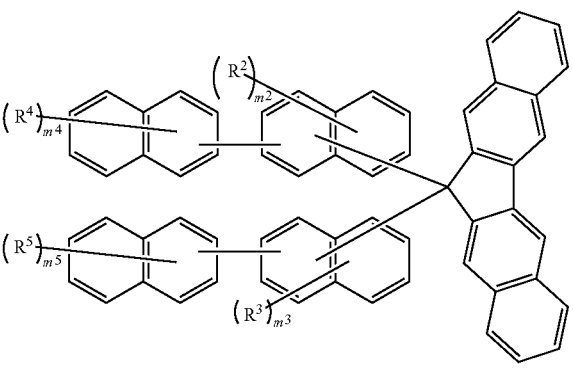
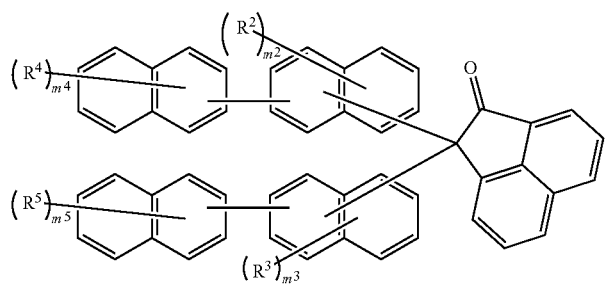

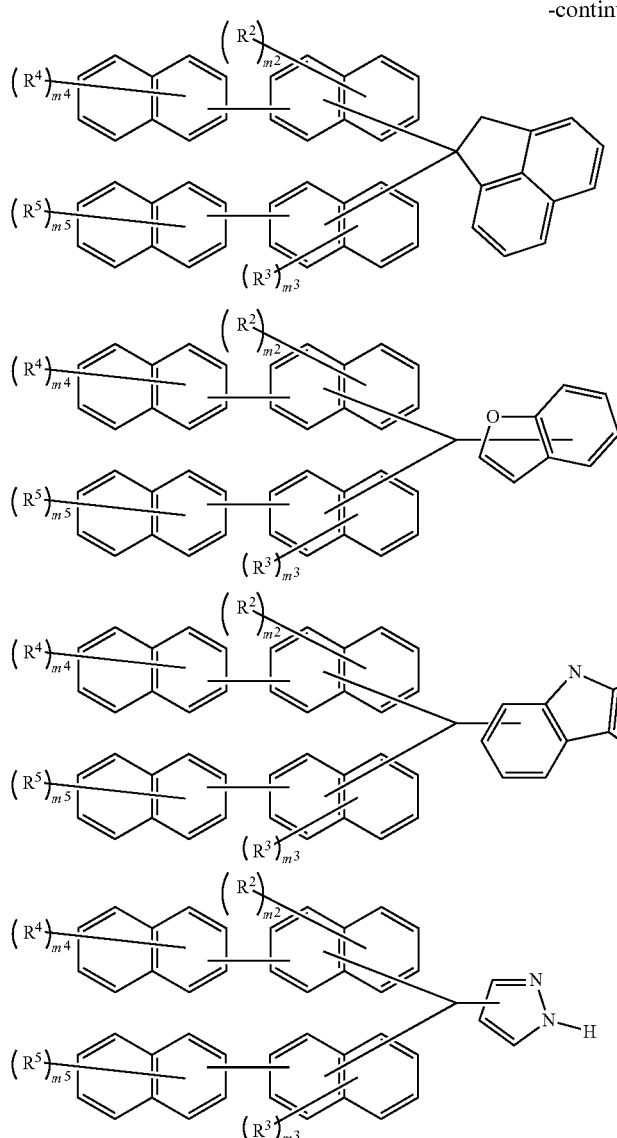
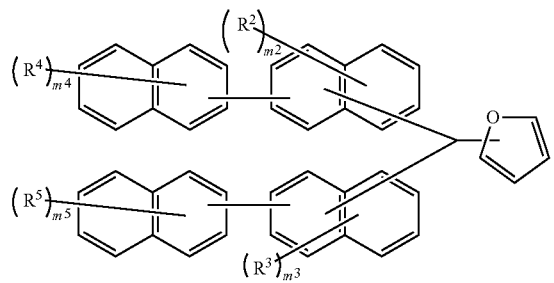
In the above compounds, $R^2$ to $R^5$ and $m^2$ to $m^5$ are as defined in the description of the above formula (1). However, $m^2$, $m^3$, $m^4$, and $m^5$ are not 0 at the same time, and at least one selected from $R^2$ to $R^5$ is a group in which a hydrogen atom of a hydroxy group is replaced with an acid dissociation group.
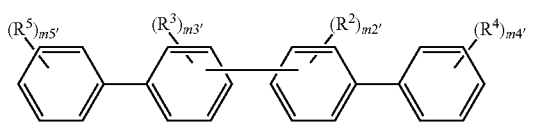
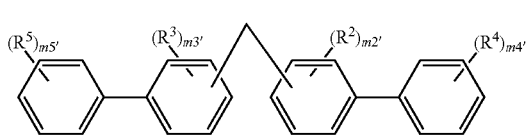
-continued
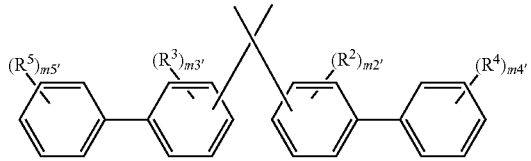
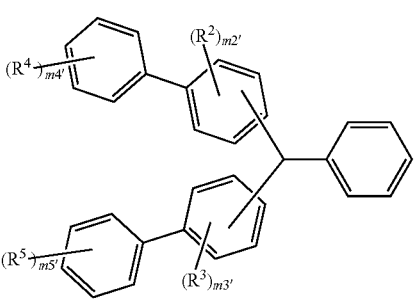

-continued
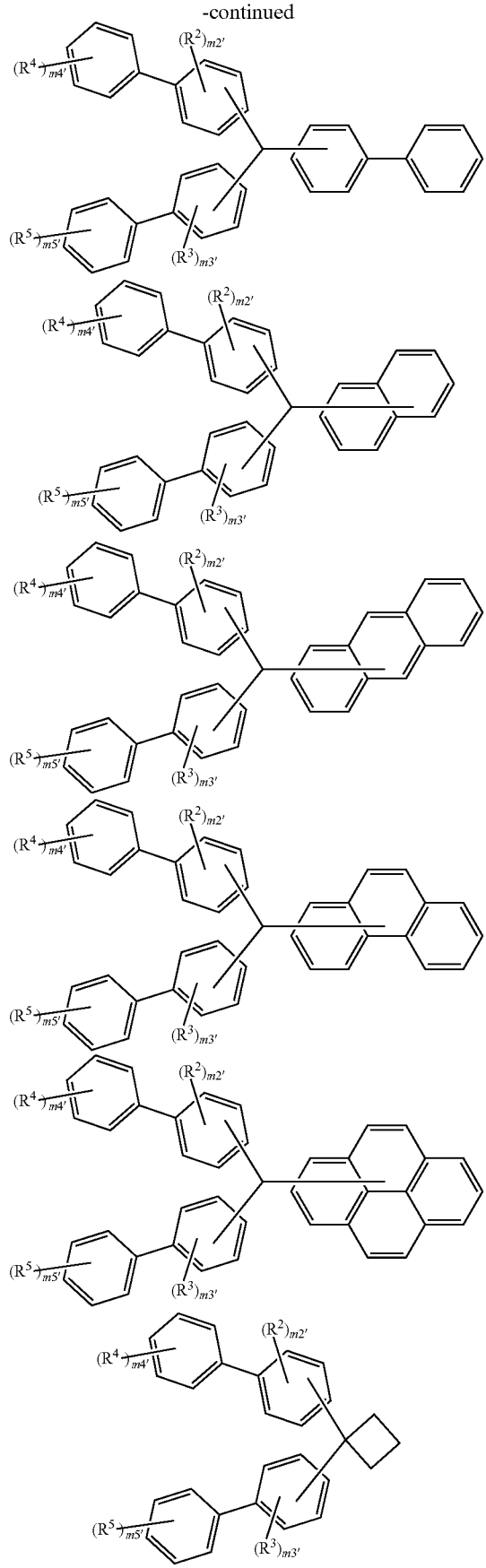
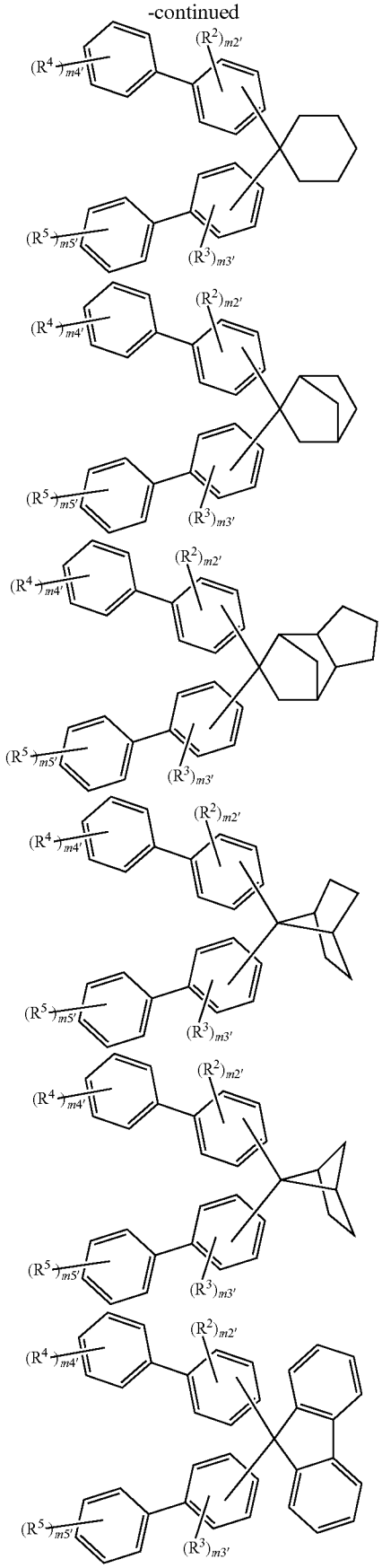

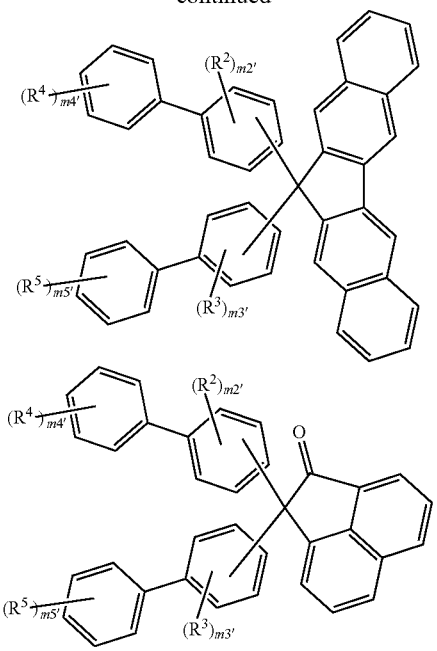

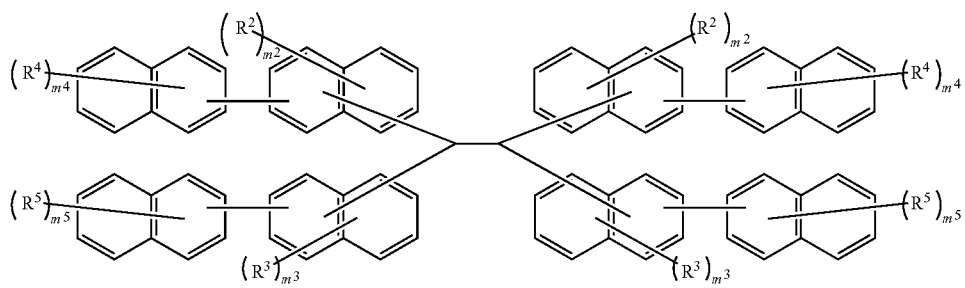

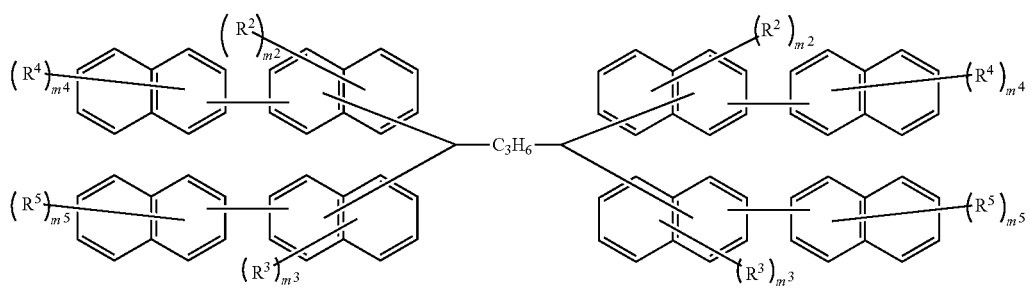

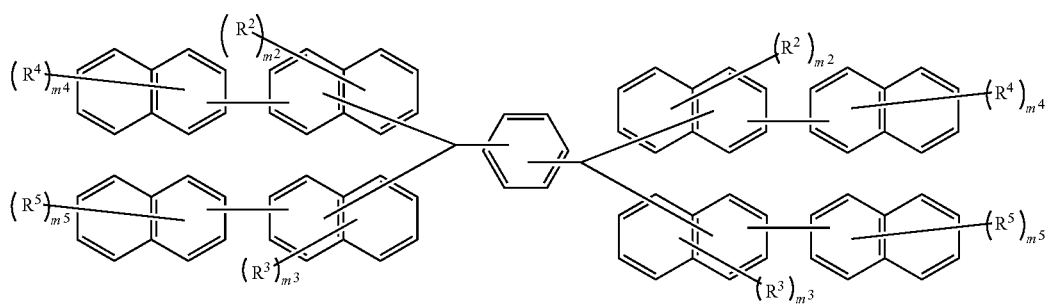

In the above compounds, $R^2$ to $R^5$ are as defined in the description of the above formula (1). $m^{2'}$ and $m^{3'}$ are each independently an integer of 0 to 4, and $m^{4'}$ and $m^{5'}$ are each independently an integer of 0 to 5. However, $m^{4'}$ and $m^{5'}$ are not 0 at the same time, and at least one selected from $R^2$ to $R^5$ is a group in which a hydrogen atom of a hydroxy group is replaced with an acid dissociation group.

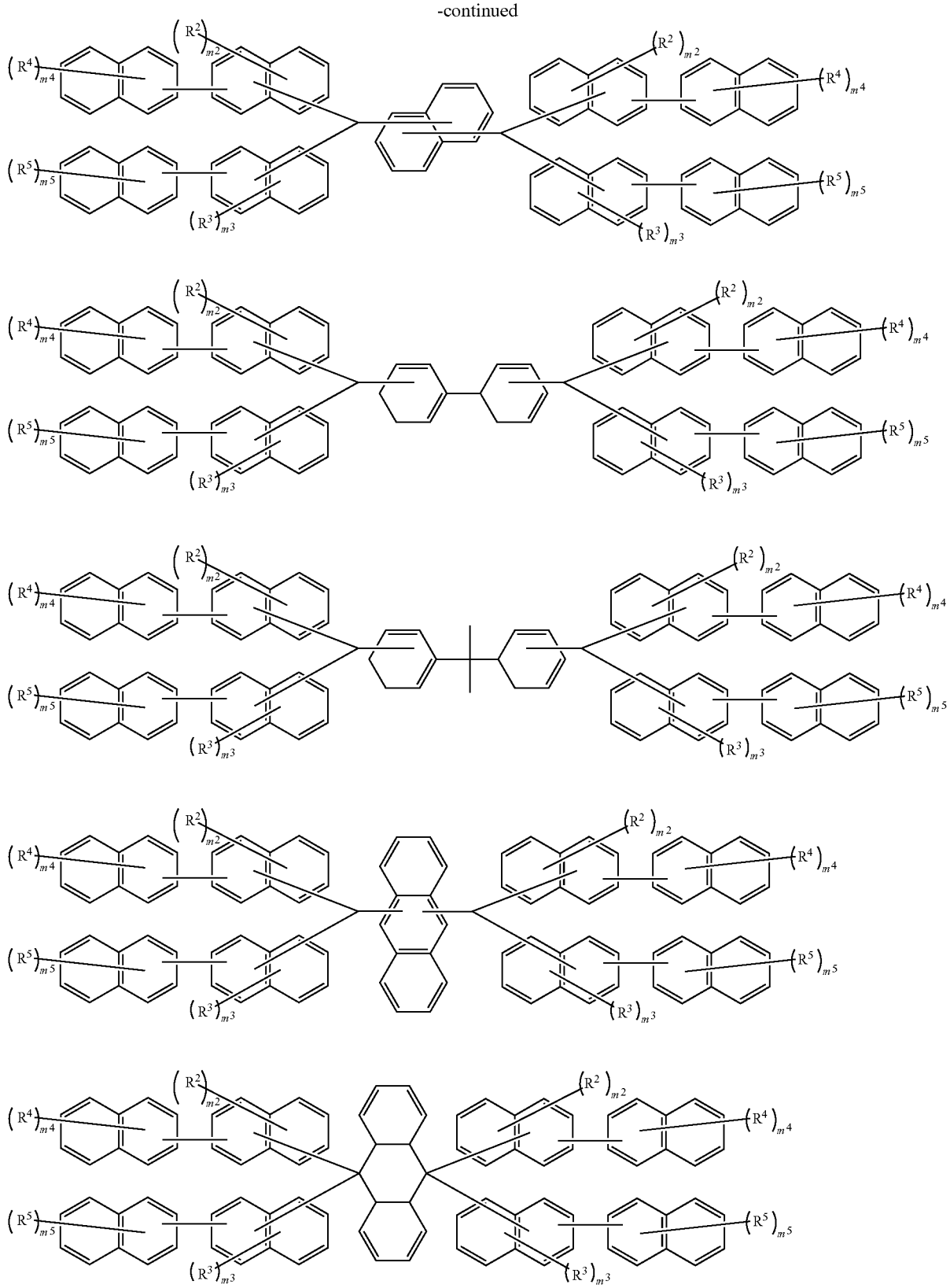
In the above compounds, $R^2$ to $R^5$ and $m^2$ to $m^5$ are as defined in the description of the above formula (1). However, $m^2$, $m^3$, $m^4$, and $m^5$ are not 0 at the same time, and at least one selected from $R^2$ to $R^5$ is a group in which a hydrogen atom of a hydroxy group is replaced with an acid dissociation group.

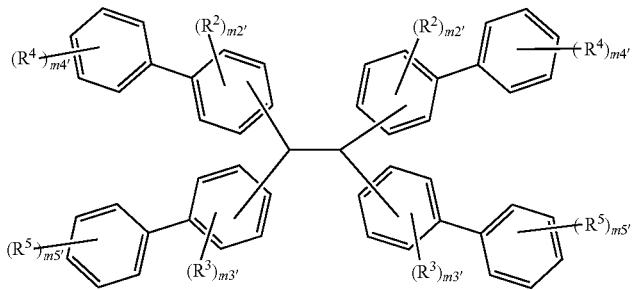
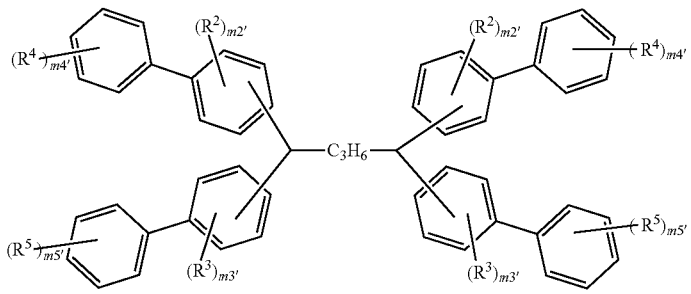
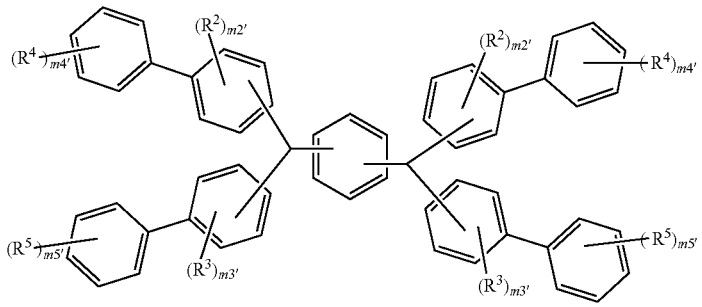
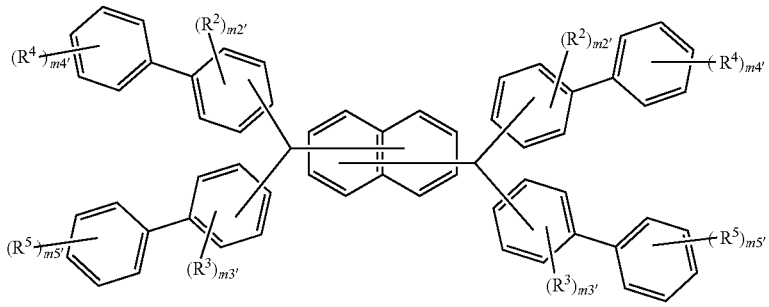
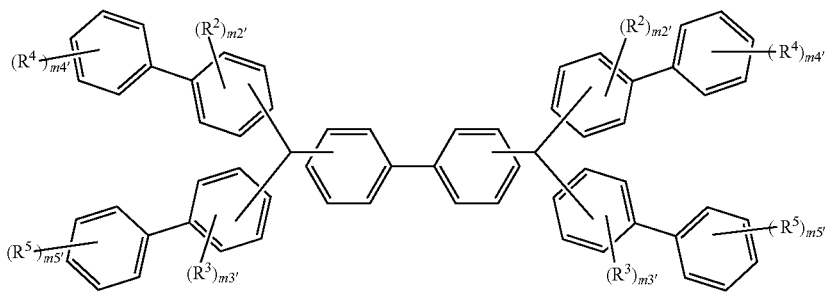

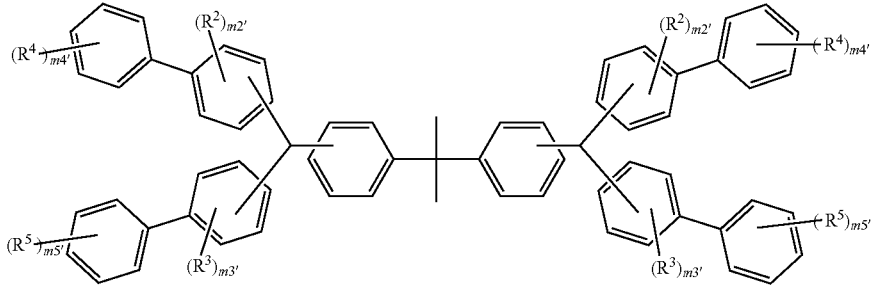

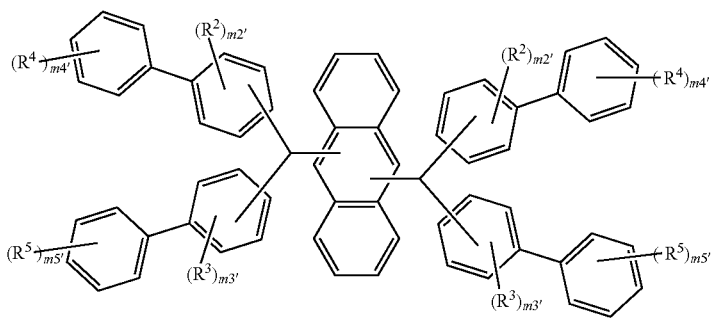

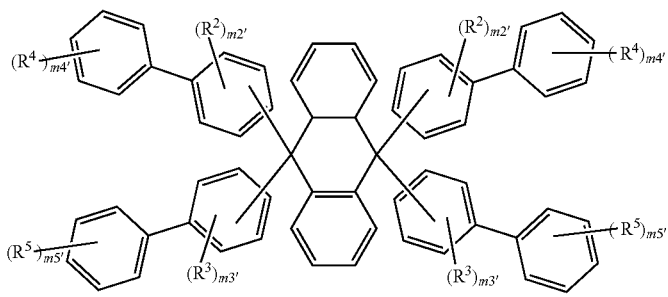

In the above compounds, $R^2$ to $R^5$ are as defined in the description of the above formula (1). $m^{2'}$ and $m^{3'}$ are each independently an integer of 0 to 4, and $m^{4'}$ and $m^{5'}$ are each independently an integer of 0 to 5. However, $m^{4'}$ and $m^{5'}$ are not 0 at the same time, and at least one selected from $R^2$ to $R^5$ is a group in which a hydrogen atom of a hydroxy group is replaced with an acid dissociation group.

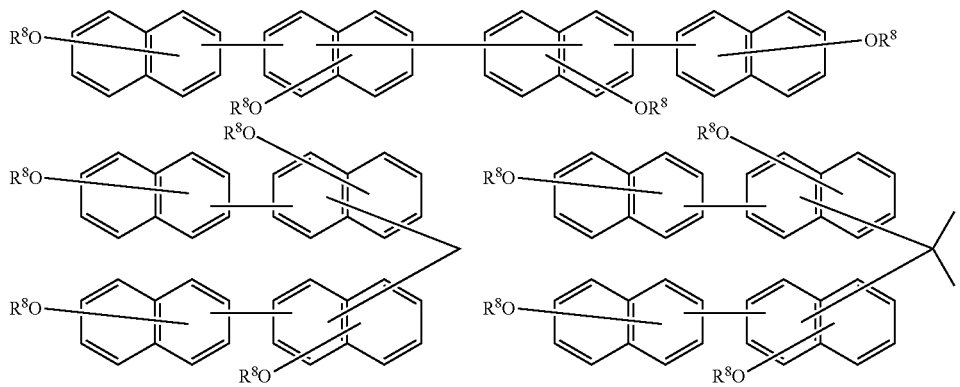

-continued
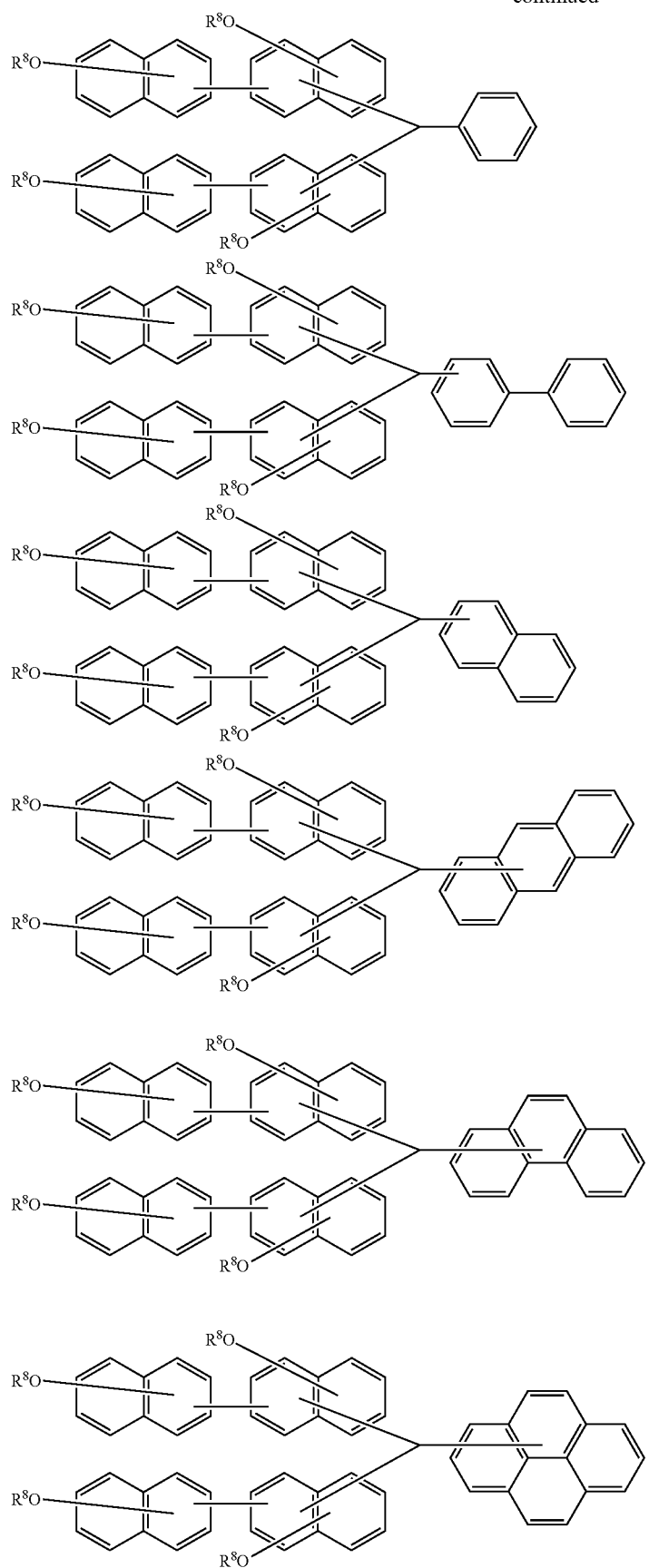

-continued
| 39 | 40 |
|---|---|
| 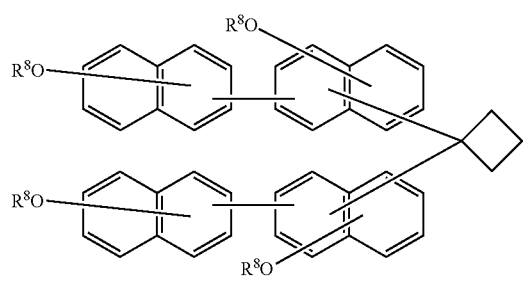 | 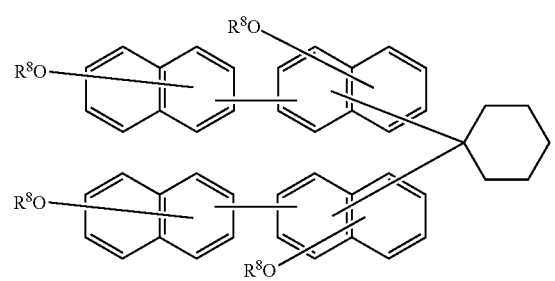 |
| 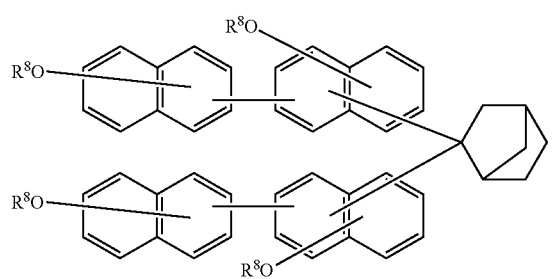 | 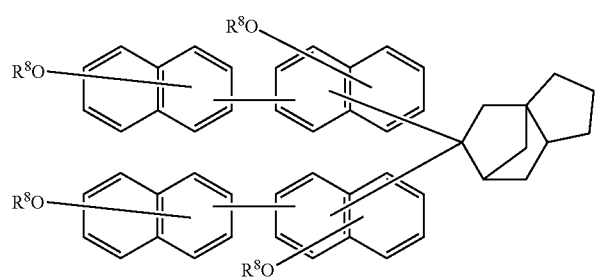 |
| 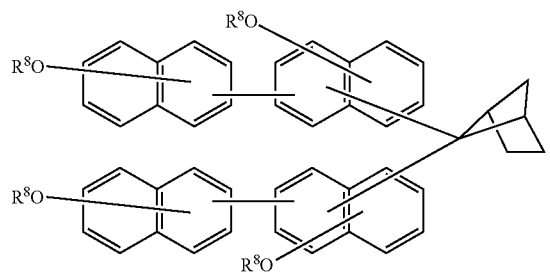 | 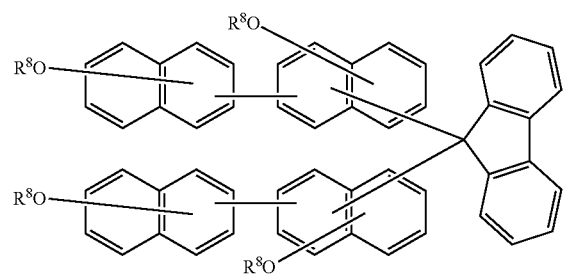 |
| 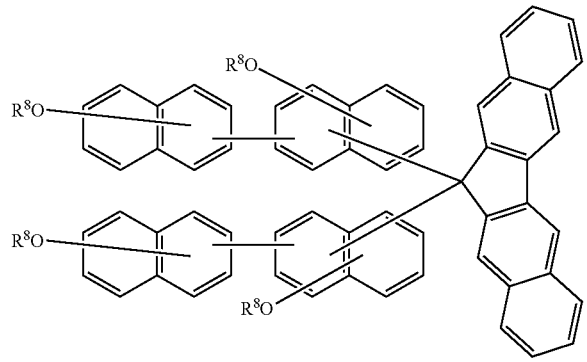 | 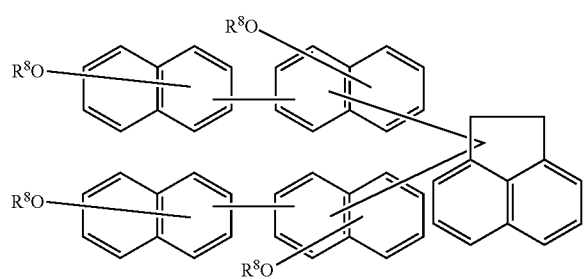 |
| 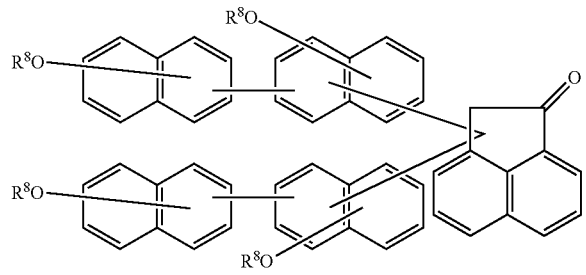 | 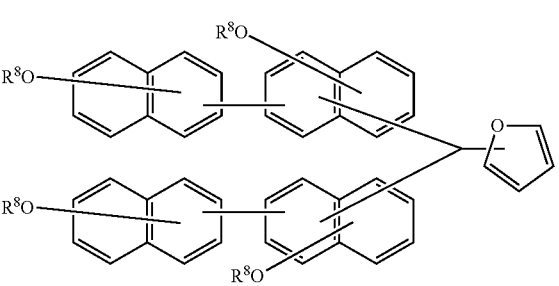 |

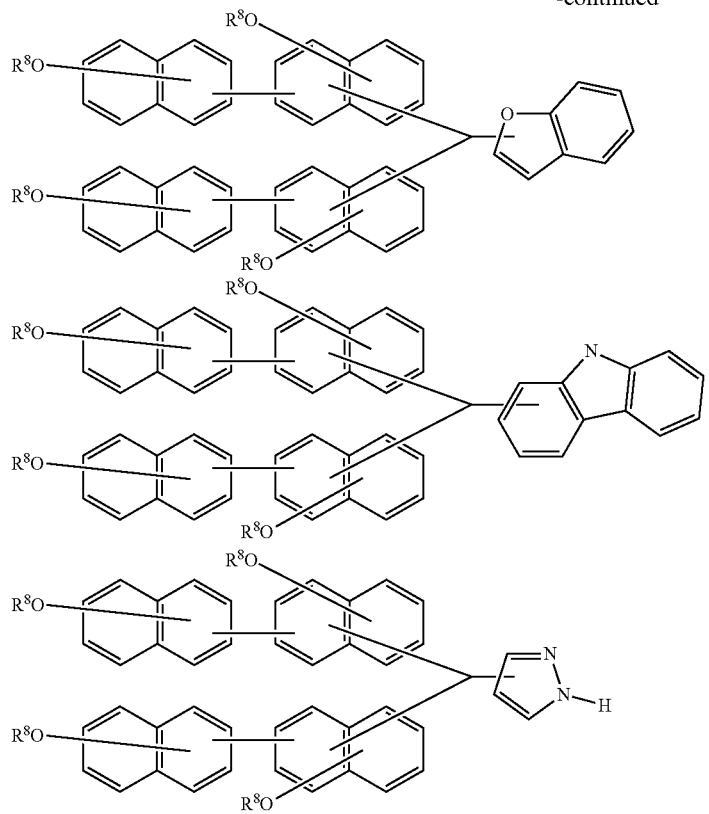
In the above compounds, each $R^8$ is independently a hydrogen atom or an acid dissociation group. However, at least one $R^8$ is an acid dissociation group.
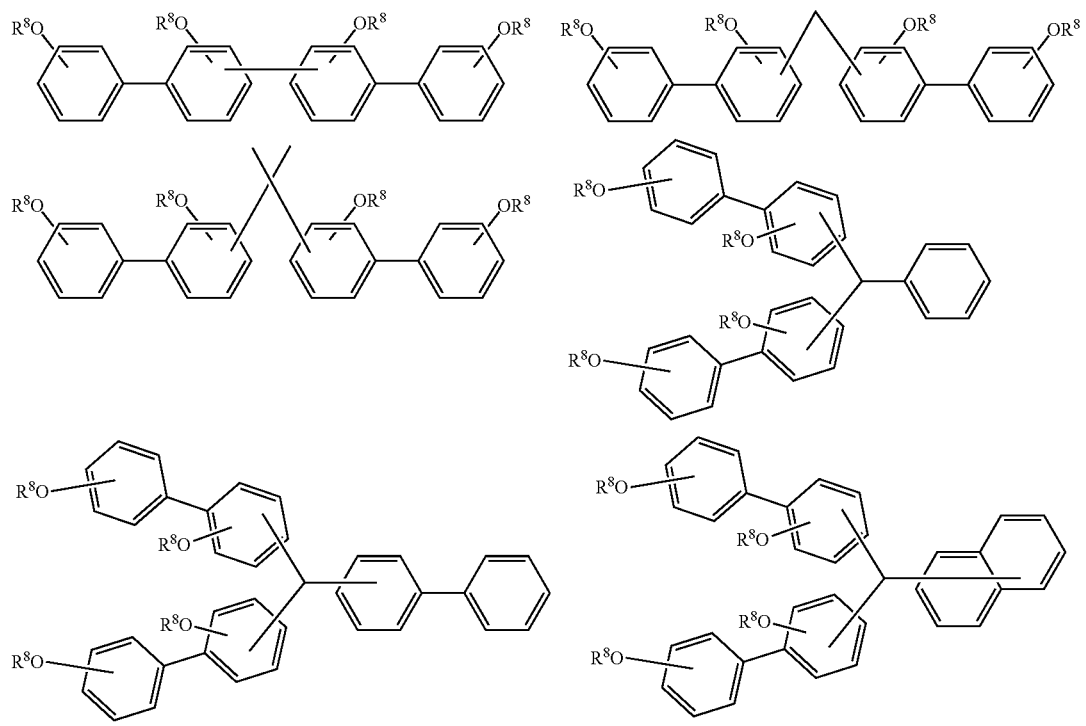

-continued
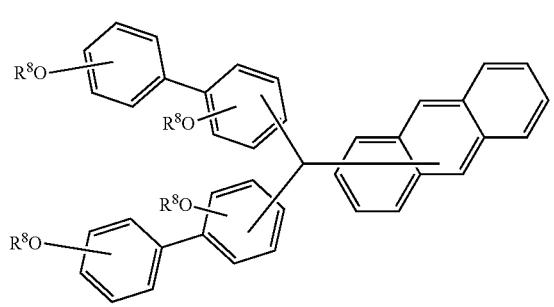
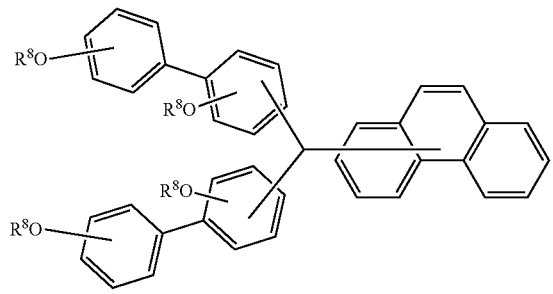
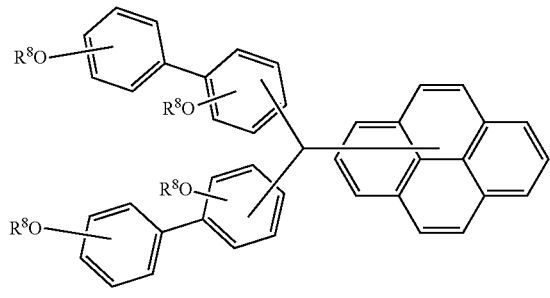
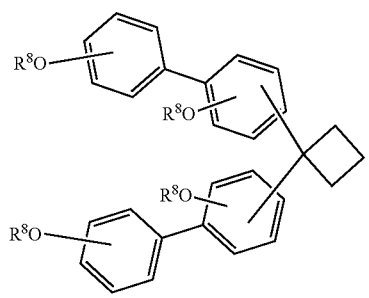
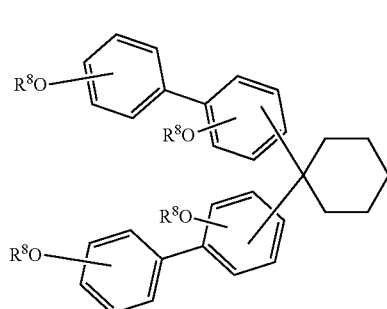
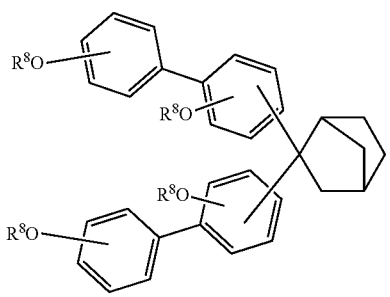
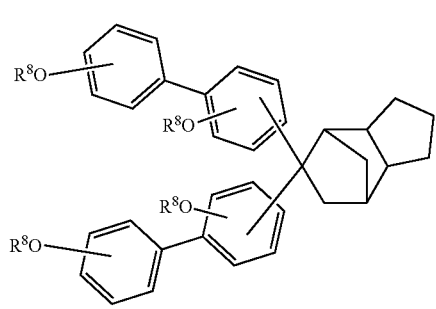
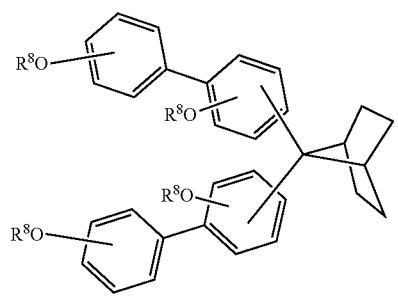
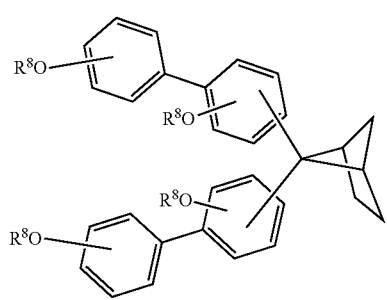
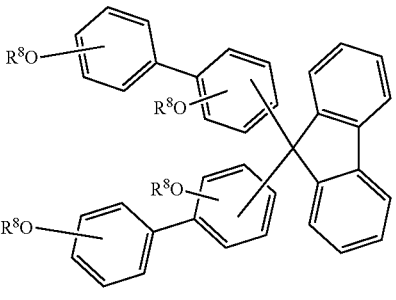

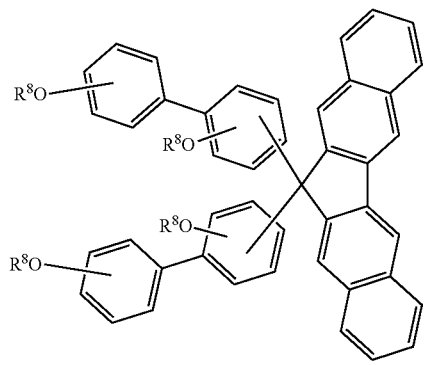
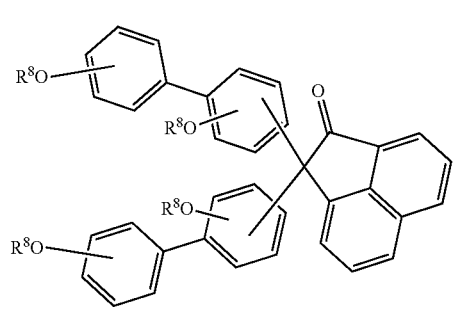
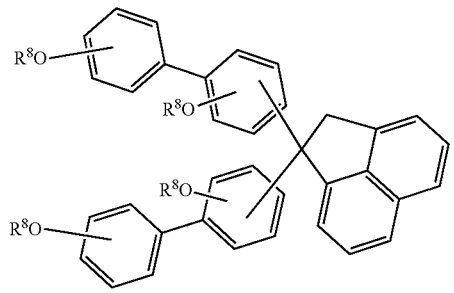
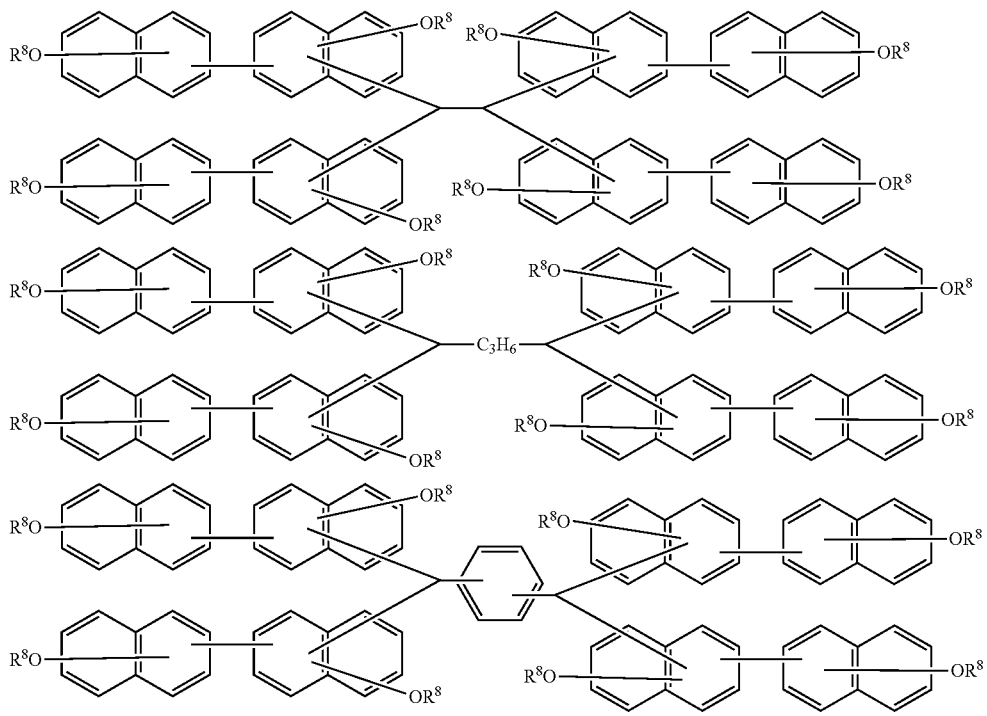
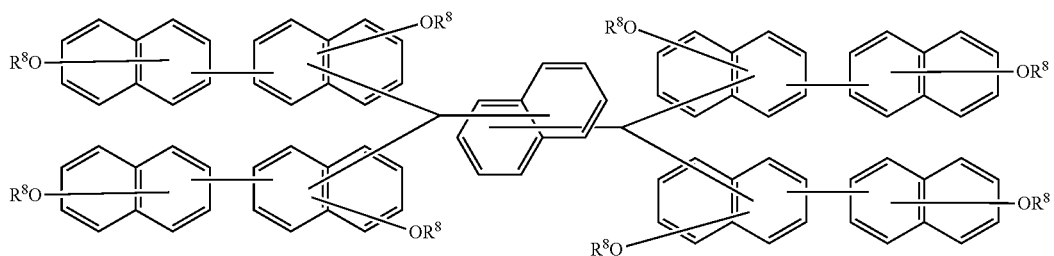

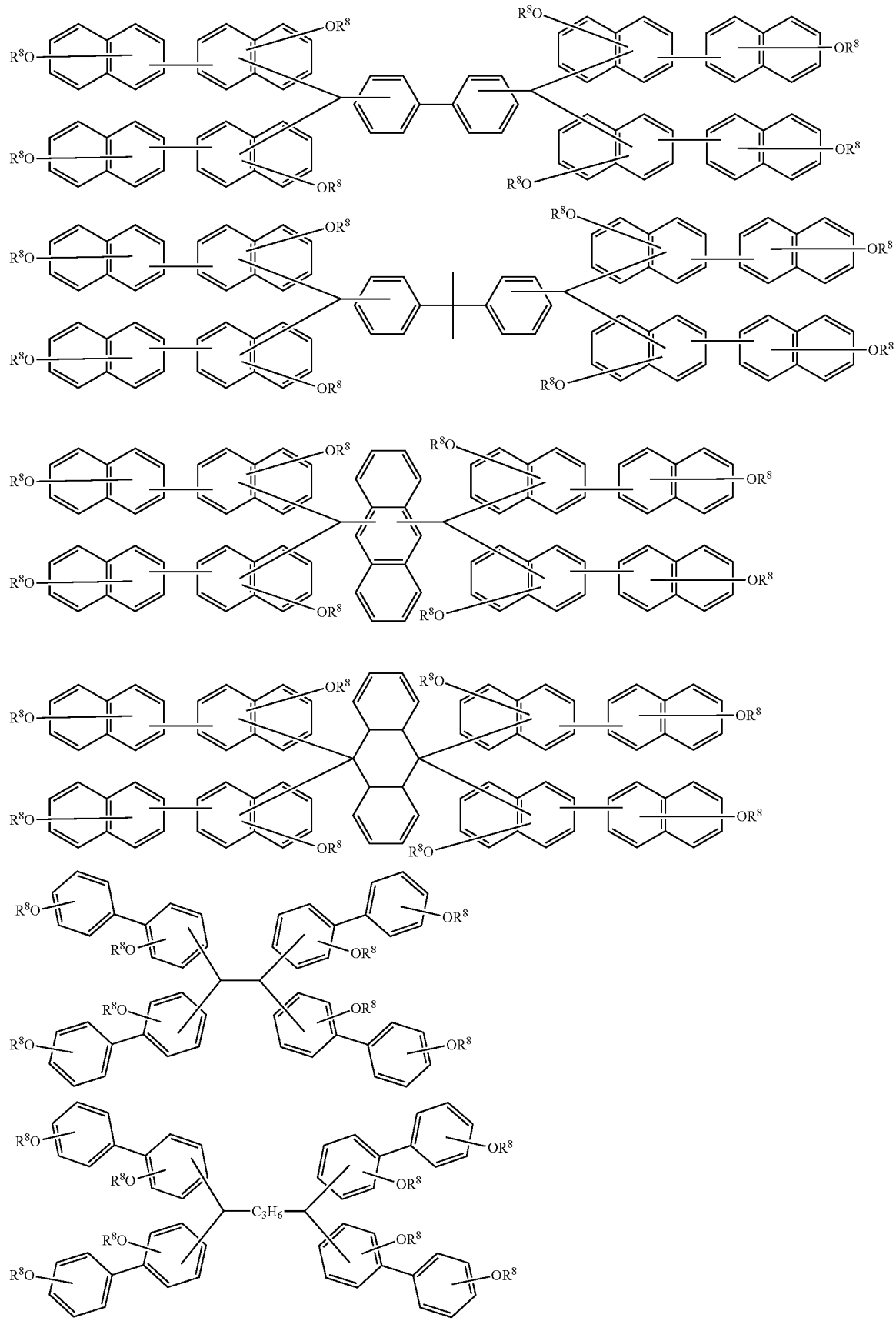

-continued
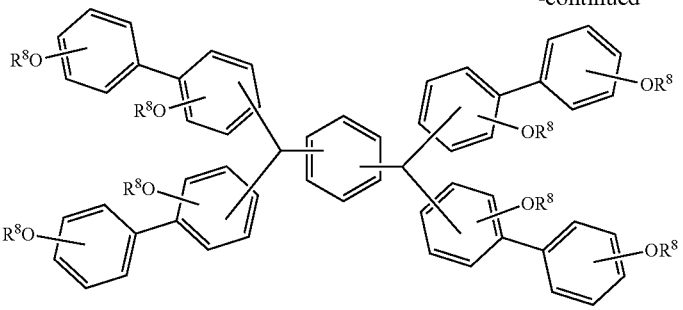
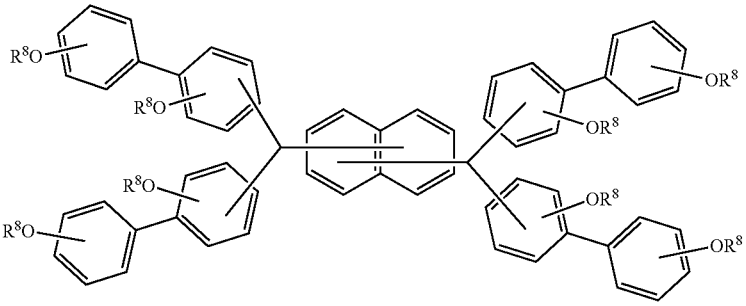
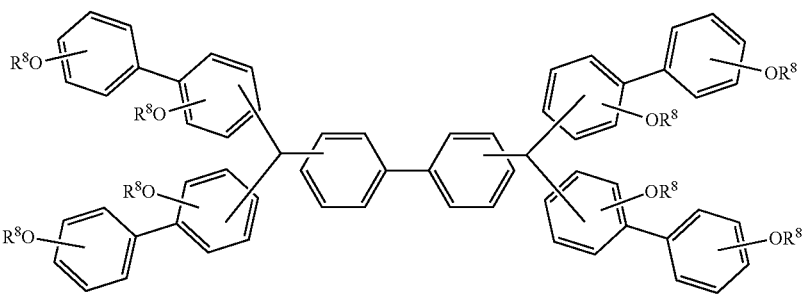
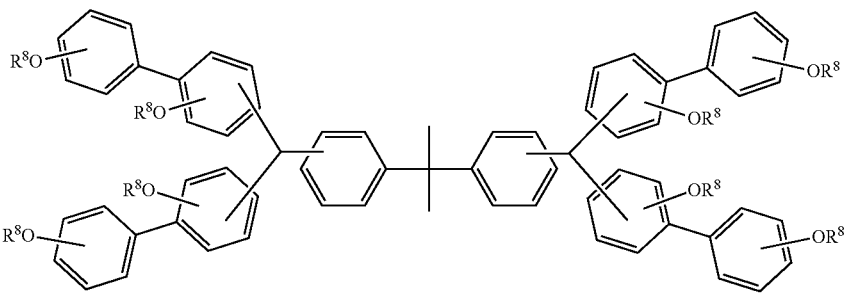
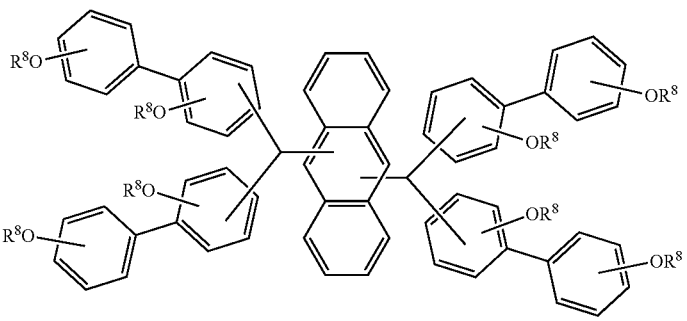

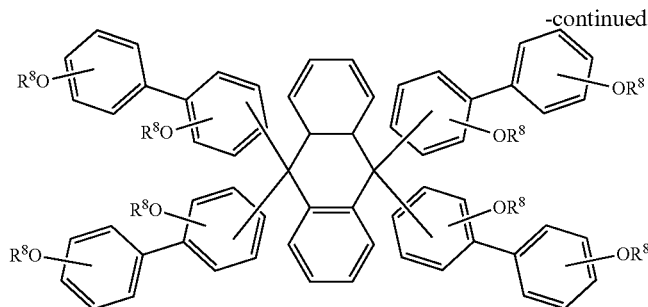

-continued

In the above compounds, each $R^8$ is independently a hydrogen atom or an acid dissociation group. However, at least one $R^8$ is an acid dissociation group.

[Method for Producing Compound Represented by Formula (1)]

The compound represented by the formula (1) of the present embodiment can be arbitrarily synthesized by the application of a publicly known approach, and the synthesis approach is not particularly limited. A precursor compound (a compound of the formula (1) wherein at least one selected from the group consisting of $R^2$ to $R^5$ has a hydroxy group) of the compound represented by the formula (1) can be obtained, for example, by subjecting one or more compounds (A1) selected from the group consisting of a biphenol, a bithiophenol, a binaphthol, a bithionaphthol, and a bianthracenol, and one or more compounds (A2) selected from the group consisting of an aldehyde and a ketone to polycondensation reaction in the presence of an acid catalyst at normal pressure. If necessary, this reaction can also be carried out under increased pressure.

Examples of the biphenol include, but not particularly limited to, biphenol, methylbiphenol, and methoxybi phenol. These biphenols can be used alone as one kind or can be used in combination of two or more kinds. Among them, biphenol is more preferably used from the viewpoint of the stable supply of raw materials.

Examples of the bithiophenol include, but not particularly limited to, bithiophenol, methylbithiophenol, and methoxybithiophenol. These bithiophenols can be used alone as one kind or can be used in combination of two or more kinds. Among them, bithiophenol is more preferably used from the viewpoint of the stable supply of raw materials.

Examples of the binaphthol include, but not particularly limited to, binaphthol, methylbinaphthol, and methoxybinaphthol. These binaphthols can be used alone as one kind or can be used in combination of two or more kinds. Among them, binaphthol is more preferably used from the viewpoint of increasing a carbon atom concentration and improving heat resistance.

Examples of the bithionaphthol include, but not particularly limited to, bithionaphthol, methylbithionaphthol, and methoxybithionaphthol. These bithionaphthols can be used alone as one kind or can be used in combination of two or more kinds. Among them, bithionaphthol is more preferably used from the viewpoint of increasing a carbon atom concentration and improving heat resistance.

Examples of the above bianthracenol include, but not particularly limited to, bianthracenol, methylbianthracenol, and methoxybianthracenol. These bianthracenols can be used alone as one kind or can be used in combination of two or more kinds. Among them, bianthracenol is more prefer- ably used from the viewpoint of increasing a carbon atom concentration and improving heat resistance.

As the aldehyde, for example, formaldehyde, trioxane, paraformaldehyde, acetaldehyde, propylaldehyde, butylaldehyde, hexylaldehyde, decylaldehyde, undecylaldehyde, phenylacetaldehyde, phenylpropylaldehyde, furfural, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxyaldehyde, phenanthrenecarboxyaldehyde, pyrenecarboxyaldehyde, glyoxal, glutaraldehyde, phthalaldehyde, naphthalenedicarboxyaldehyde, biphenyldicarboxyaldehyde, anthracenedicarboxyaldehyde, bis(diformylphenyl)methane, bis(diformylphenyl)propane, or benzenetricarboxyaldehyde is preferably used from the viewpoint of providing high heat resistance.

A compound suitable as the aldehyde is a compound of 2 to 59 carbon atoms having 1 to 4 formyl groups and a group containing an iodine atom and is selected from an aromatic aldehyde compound, an aliphatic aldehyde compound, and the like. The aromatic aldehyde compound is preferably an aldehyde compound of 7 to 24 carbon atoms. Examples thereof include iodobenzaldehyde, methyliodobenzaldehyde, dimethyliodobenzaldehyde, ethyliodobenzaldehyde, propyliodobenzaldehyde, butyliodobenzaldehyde, ethylmethyliodobenzaldehyde, isopropylmethyliodobenzaldehyde, diethyliodobenzaldehyde, methoxyiodobenzaldehyde, iodonaphthaldehyde, iodoanthraldehyde, cyclopropyliodobenzaldehyde, cyclobutyliodobenzaldehyde, cyclopentyliodobenzaldehyde, cyclohexyliodobenzaldehyde, phenyliodobenzaldehyde, naphthyliodobenzaldehyde, adamantyliodobenzaldehyde, norbornyliodobenzaldehyde, lactyliodobenzaldehyde, isopropyliodobenzaldehyde, normal iodobenzaldehyde, bromoiodobenzaldehyde, dimethylaminoiodobenzaldehyde, hydroxyiodobenzaldehyde, dihydroxyiodobenzaldehyde, trihydroxyiodobenzaldehyde, and 5-iodovanillin. Iodobenzaldehyde, methyliodobenzaldehyde, dimethyliodobenzaldehyde, ethyliodobenzaldehyde, or 5-iodovanillin is more preferable, and iodobenzaldehyde or 5-iodovanillin is further preferable. The aromatic aldehyde compound may have a linear or branched alkyl group of 1 to 4 carbon atoms, a cyano group, a hydroxy group, halogen, or the like within the range not deteriorating the effect of the present invention. The aromatic aldehyde compound may be used alone or in combination of two or more kinds.

The aliphatic aldehyde compound is preferably a compound of 3 to 24 carbon atoms. Examples thereof include iodopropanal, iodoisopropanal, iodobutanal, iodoisobutanal, iodo-t-butanal, iodopentanal, iodoisopentanal, iodoneopentanal, iodohexanal, iodoisohexanal, iodooctanal, iodododecanal, iodoundecanal, iodocyclopropanecarboxyaldehyde, iodocyclobutanecarboxyaldehyde, and iodocyclohexanecarboxyaldehyde. Iodoisobutanal, iodo-t-butanal, iodopentanal, iodoisopentanal, iodoneopentanal, iodohexanal, iodoisohexanal, iodooctanal, iodododecanal, iodoundecanal, iodocyclopropanecarboxyaldehyde, iodocyclobutanecarboxyaldehyde, or iodocyclohexanecarboxyaldehyde is more preferable, and iodooctanal, iodododecanal, iodododecanal, or iodocyclohexanecarboxyaldehyde is further preferable. The aliphatic aldehyde compound may have a linear or branched alkyl group of 1 to 4 carbon atoms, a cyano group, a hydroxy group, a halogen atom, or the like within the range not deteriorating the effect of the present invention. The aliphatic aldehyde compound may be used alone or in combination of two or more kinds.

Also, an aldehyde compound having a heterocyclic group, such as carbazole-3-carbaldehyde, N-methylcarbazole-3-carbaldehyde, N-ethylcarbazole-3-carbaldehyde, N-propylcarbazole-3-carbaldehyde, N-(t-butyl)carbazole-3-carbaldehyde, N-hydroxyethylcarbazole-3-carbaldehyde, N-cyclohexylcarbazole-3-carbaldehyde, N-phenylcarbazole-3-carbaldehyde, 4-formylimidazole, 1-methyl-4-formylimidazole, 2-methyl-4-formylimidazole, 2-butyl-4-formylimidazole, 2-iodo-4-formylimidazole, 5-formylimidazole, 1-methyl-5-formylimidazole, 2-methyl-5-formylimidazole, 2-butyl-5-formylimidazole, 2-iodo-5-formyl-2-formylimidazole, 2-furancarbaldehyde, or 5-iodo-2-furancarbaldehyde is suitably used. The aldehyde compound having a heterocyclic group may be used alone or in combination of two or more kinds.

Examples of the ketone include, but not particularly limited to, acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone. These ketones can be used alone as one kind or can be used in combination of two or more kinds. Among them, cyclopentanone, cyclohexanone, norbornanone, tricyclohexanone, tricyclodecanone, adamantanone, fluorenone, benzofluorenone, acenaphthenequinone, acenaphthenone, or anthraquinone is preferably used from the viewpoint of providing high heat resistance.

The acid catalyst used in the reaction can be arbitrarily selected and used from publicly known catalysts and is not particularly limited. Inorganic acids and organic acids are widely known as such acid catalysts, and examples include, but not particularly limited to, inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, organic acids and solid acids are preferable from the viewpoint of production, and hydrochloric acid or sulfuric acid is preferably used from the viewpoint of production such as easy availability and handleability. The acid catalysts can be used alone as one kind or can be used in combination of two or more kinds. Also, the amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials.

Upon the reaction, a reaction solvent may be used. The reaction solvent is not particularly limited as long as the reaction of the aldehyde or the ketone used with the biphenol, the bithiophenol, the binaphthol, the bithionaphthol, or the bianthracenediol proceeds, and can be arbitrarily selected and used from publicly known solvents. Examples include ethyl acetate, propyl acetate, butyl acetate, 4-butyrolactone, ethylene glycol, propylene glycol, methanol, ethanol, propanol, butanol, tetrahydrofuran, dioxane, ethylene glycol dimethyl ether, ethylene glycol diethyl ether, propylene glycol monomethyl ether, propylene glycol monoethyl ether, propylene glycol monomethyl ether acetate, and a mixed solvent thereof. The solvents can be used alone as one kind or can be used in combination of two or more kinds.

Also, the amount of these reaction solvents used can be arbitrarily set according to, for example, the kind of the raw materials used and the catalyst used and moreover the reaction conditions and is not particularly limited, but is preferably in the range of 0 to 2000 parts by mass based on 100 parts by mass of the reaction raw materials. Furthermore, the reaction temperature in the reaction can be arbitrarily selected according to the reactivity of the reaction raw materials and is not particularly limited, but is usually within the range of 10 to 200° C.

In order to obtain the precursor compound of the compound represented by the formula (1) of the present embodiment, a higher reaction temperature is more preferable. Specifically, the range of 60 to 200° C. is preferable. The reaction method can be arbitrarily selected and used from publicly known approaches and is not particularly limited, and there are a method of charging the biphenol, the bithiophenol, the binaphthol, the bithionaphthol, or the bianthracenediol, the aldehyde or the ketone, and the catalyst in one portion, and a method of dropping the biphenol, the bithiophenol, the binaphthol, the bithionaphthol, or the bianthracenediol, and the aldehyde or the ketone, in the presence of the catalyst. After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, the compound which is a precursor can be obtained.

As preferable reaction conditions, the reaction proceeds by using 1.0 mol to an excess of the biphenol, the bithiophenol, the binaphthol, the bithionaphthol, or the bianthracenediol and 0.001 to 1 mol of the acid catalyst based on 1 mol of the aldehyde or the ketone, and reacting them at 50 to 150° C. at normal pressure for about 20 minutes to 100 hours.

The precursor compound can be isolated by a publicly known method after the reaction terminates. The precursor of the compound represented by the above formula (1) can be obtained, for example, by concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying.

The compound represented by the above formula (1), which is the target compound, can be obtained, for example, by replacing a hydrogen atom of a phenolic hydroxy group in the precursor compound thus obtained with an acid dissociation group by a publicly known method.

The method for replacing a hydrogen atom of a phenolic hydroxy group with an acid dissociation group is not particularly limited. For example, an acid dissociation group can be introduced to at least one phenolic hydroxy group of the above polyphenol compound. The compound for introducing the acid dissociation group can be synthesized or easily obtained by a publicly known method. Examples thereof include, but not particularly limited to, acid chlorides, acid anhydrides, active carboxylic acid derivative compounds such as dicarbonate, alkyl halides, vinyl alkyl ethers, dihydropyran, and halocarboxylic acid alkyl esters.

For example, the precursor compound is dissolved or suspended in an aprotic solvent such as acetone, tetrahydrofuran (THF), or propylene glycol monomethyl ether acetate. Subsequently, a vinyl alkyl ether such as ethyl vinyl ether, or dihydropyran is added to the solution or the suspension, and the mixture is reacted at 20 to 60° C. at normal pressure for 6 to 72 hours in the presence of an acid catalyst such as pyridinium p-toluenesulfonate. The reaction solution is neutralized with an alkali compound and added to distilled water to precipitate a white solid. Then, the separated white solid can be washed with distilled water and dried to obtain the compound represented by the formula (1).

Alternatively, the precursor compound is dissolved or suspended in an aprotic solvent such as acetone, THF, or propylene glycol monomethyl ether acetate.

Subsequently, an alkyl halide such as ethyl chloromethyl ether or a halocarboxylic acid alkyl ester such as methyladamantyl bromoacetate is added to the solution or the suspension, and the mixture is reacted at 20 to 110° C. at normal pressure for 6 to 72 hours in the presence of an alkali catalyst such as potassium carbonate. The reaction solution is neutralized with an acid such as hydrochloric acid and added to distilled water to precipitate a white solid. Then, the separated white solid can be washed with distilled water and dried to obtain the compound represented by the formula (1).

The compound represented by the above formula (1) used in the present embodiment may be alone or can be a mixture of two or more kinds.

[Resin]

The resin of the present embodiment is a resin comprising the compound represented by the above formula (1) as a constituent and has a structural unit derived from the compound represented by the above formula (1).

The resin of the present embodiment is obtained by, for example, reacting the compound represented by the above formula (1) with a crosslinking compound.

As the crosslinking compound, a publicly known monomer can be used without particular limitations as long as it can oligomerize or polymerize the compound represented by the above formula (1). Specific examples thereof include, but not particularly limited to, aldehydes, ketones, carboxylic acids, carboxylic acid halides, halogen-containing compounds, amino compounds, imino compounds, isocyanates, and unsaturated hydrocarbon group-containing compounds.

Specific examples of the resin according to the present embodiment include resins that are made novolac by, for example, a condensation reaction between the compound represented by the above formula (1) with an aldehyde that is a crosslinking compound.

Herein, examples of the aldehyde used when making the compound represented by the above formula (1) novolac include, but not particularly limited to, formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarboaldehyde, phenanthrenecarboaldehyde, pyrenecarboaldehyde, and furfural. Among these, formaldehyde is more preferable. These aldehydes can be used alone as one kind or may be used in combination of two or more kinds. The amount of the above aldehydes used is not particularly limited, but is preferably 0.2 to 5 mol and more preferably 0.5 to 2 mol based on 1 mol of the compound represented by the above formula (1).

A catalyst can also be used in the condensation reaction between the compound represented by the above formula (1) and the aldehyde. The acid catalyst used herein can be arbitrarily selected and used from publicly known catalysts and is not particularly limited. Inorganic acids and organic acids are widely known as such acid catalysts, and examples include, but not particularly limited to, inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, organic acids and solid acids are preferable from the viewpoint of production, and hydrochloric acid or sulfuric acid is preferable from the viewpoint of production such as easy availability and handleability. The acid catalysts can be used alone as one kind, or can be used in combination of two or more kinds. Also, the amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials. The aldehyde is not necessarily needed in the case of a copolymerization reaction with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborn-2-ene, α-pinene, β-pinene, and limonene.

A reaction solvent can also be used in the condensation reaction between the compound represented by the above formula (1) and the aldehyde. The reaction solvent in the polycondensation can be arbitrarily selected and used from publicly known solvents and is not particularly limited, and examples include water, methanol, ethanol, propanol, butanol, tetrahydrofuran, dioxane, or a mixed solvent thereof. The solvents can be used alone as one kind, or can be used in combination of two or more kinds.

Also, the amount of these solvents used can be arbitrarily set according to, for example, the kind of the raw materials used and the catalyst used and moreover the reaction conditions and is not particularly limited, but is preferably in the range of 0 to 2000 parts by mass based on 100 parts by mass of the reaction raw materials. Furthermore, the reaction temperature can be arbitrarily selected according to the reactivity of the reaction raw materials and is not particularly limited, but is usually within the range of 10 to 200° C. The reaction method can be arbitrarily selected and used from publicly known approaches and is not particularly limited, and there are a method of charging the compound represented by the above formula (1), the aldehyde, and the catalyst in one portion, and a method of dropping the compound represented by the above formula (1) and the aldehyde in the presence of the catalyst.

After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, a novolac resin that is the target compound can be obtained.

Herein, the resin according to the present embodiment may be a homopolymer of a compound represented by the above formula (1), or may be a copolymer with a further phenol. Herein, examples of the copolymerizable phenol include, but not particularly limited to, phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol.

The resin according to the present embodiment may be a copolymer with a polymerizable monomer other than the above-described further phenols. Examples of such a copolymerization monomer include, but not particularly limited to, naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornene, pinene, and limonene. The resin according to the present embodiment may be a copolymer of two or more components (for example, a binary to quaternary system) composed of the compound represented by the above formula (1) and the above-described phenol, may be a copolymer of two or more components (for example, a binary to quaternary system) composed of the compound represented by the above formula (1) and the above-described copolymerization monomer, or may be a copolymer of three or more components (for example, a tertiary to quaternary system) composed of the compound represented by the above formula (1), the above-described phenol, and the above-described copolymerization monomer.

The molecular weight of the resin according to the present embodiment is not particularly limited, and the weight average molecular weight (Mw) in terms of polystyrene is preferably 500 to 30,000 and more preferably 750 to 20,000. The resin according to the present embodiment preferably has dispersibility (weight average molecular weight Mw/number average molecular weight Mn) within the range of 1.2 to 7 from the viewpoint of enhancing crosslinking efficiency while suppressing volatile components during baking. The above Mn can be determined by a method described in Examples mentioned later.

[Resist Composition]

The resist composition of the present embodiment contains the compound represented by the above formula (1) or the resin comprising the compound as a constituent. Also, the resist composition of the present embodiment may contain both of the compound represented by the above formula (1) and the resin comprising the compound as a constituent.

It is preferable that the resist composition of the present embodiment should contain a solvent. Examples of the solvent can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate (PGMEA), propylene glycol monoethyl ether acetate, propylene glycol mono-n-propyl ether acetate, and propylene glycol mono-n-butyl ether acetate; propylene glycol monoalkyl ethers such as propylene glycol monomethyl ether (PGME) and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbons such as toluene and xylene; ketones such as 2-heptanone, 3-heptanone, 4-heptanone, cyclopentanone (CPN), and cyclohexanone (CHN); amides such as N,N-dimethylformamide, N-methylacetamide, N,N-dimethylacetamide, and N-methylpyrrolidone; and lactones such as γ-lactone. These solvents can be used alone or in combination of two or more kinds.

The solvent used in the present embodiment is preferably a safe solvent, more preferably at least one selected from PGMEA, PGME, CHN, CPN, 2-heptanone, anisole, butyl acetate, ethyl propionate, and ethyl lactate, and still more preferably at least one selected from PGMEA, PGME, and CHN.

In the present embodiment, the amount of the solid component and the amount of the solvent are not particularly limited, but preferably the solid component is 1 to 80% by mass and the solvent is 20 to 99% by mass, more preferably the solid component is 1 to 50% by mass and the solvent is 50 to 99% by mass, still more preferably the solid component is 2 to 40% by mass and the solvent is 60 to 98% by mass, and particularly preferably the solid component is 2 to 10% by mass and the solvent is 90 to 98% by mass, based on 100% by mass of the total mass of the amount of the solid component and the solvent.

The resist composition of the present embodiment may contain at least one selected from the group consisting of an acid generating agent (C), an acid crosslinking agent (G), an acid diffusion controlling agent (E), and a further component (F), as other solid components. In the present specification, the solid components refer to components except for the solvent.

Hereinafter, the acid generating agent (C), the acid cross-linking agent (G), the acid diffusion controlling agent (E), and the further component (F) will be described.

[Acid Generating Agent]

The resist composition of the present embodiment preferably contains one or more acid generating agents (C) generating an acid directly or indirectly by irradiation of any radiation selected from visible light, ultraviolet, excimer laser, electron beam, extreme ultraviolet (EUV), X-ray, and ion beam. The amount of the acid generating agent (C) used is preferably 0.001 to 49% by mass of the total weight of the solid components, more preferably 1 to 40% by mass, still more preferably 3 to 30% by mass, and particularly preferably 10 to 25% by mass. By using the acid generating agent (C) within the above range, a pattern profile with high sensitivity and low edge roughness is obtained. In the present invention, the acid generation method is not particularly limited as long as an acid is generated in the system. By using excimer laser instead of ultraviolet such as g-ray and i-ray, finer processing is possible, and also by using electron beam, extreme ultraviolet, X-ray or ion beam as a high energy ray, further finer processing is possible.

The acid generating agent (C) is preferably at least one kind selected from the group consisting of compounds represented by the following formulas (7-1) to (7-6):

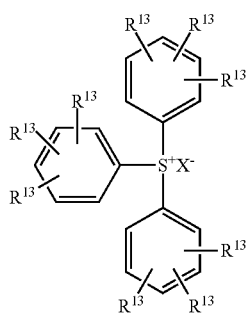
(7-1)

In the formula (7-1), $R^{13}$ may be the same or different and is each independently a hydrogen atom, a linear, branched, or cyclic alkyl group, a linear, branched, or cyclic alkoxy group, a hydroxyl group, or a halogen atom, and $X^-$ is a sulfonate ion having an alkyl group, an aryl group, a halogen-substituted alkyl group, or a halogen-substituted aryl group, or a halide ion.

The compound represented by the above formula (7-1) is preferably at least one kind selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl p-toluenesulfonate, diphenyl-2,4,6-trimethylphenylsulfonium-2-trifluoromethyl benzenesulfonate, diphenyl-2,4,6-trimethylphenylsulfonium-4-trifluoromethyl benzenesulfonate, diphenyl-2,4,6-trimethylphenylsulfonium-2,4-difluoro benzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium p-toluenesulfonate, triphenylsulfonium 10-camphorsulfonate, diphenyl-4-hydroxyphenylsulfonium 10-camphorsulfonate, and cyclo(1,3-perfluoropropanedisulfone)imidate.

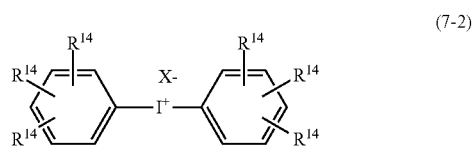
(7-2)

In the formula (7-2), $R^{14}$ may be the same or different and each independently represents a hydrogen atom, a linear, branched, or cyclic alkyl group, a linear, branched, or cyclic alkoxy group, a hydroxyl group, or a halogen atom. $X^-$ is as defined above.

The compound represented by the above formula (7-2) is preferably at least one kind selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethyl benzenesulfonate, bis(4-t-butylphenyl)iodonium-4-trifluoromethyl benzenesulfonate, bis(4-t-butylphenyl)iodonium-2,4-difluoro benzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium-2-trifluoromethyl benzenesulfonate, diphenyliodonium-4-trifluoromethyl benzenesulfonate, diphenyliodonium-2,4-difluoro benzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphorsulfonate.

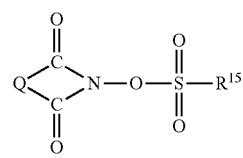
(7-3)

In the formula (7-3), Q is an alkylene group, an arylene group, or an alkoxylene group, and $R^{15}$ is an alkyl group, an aryl group, a halogen-substituted alkyl group, or a halogen-substituted aryl group.

The compound represented by the above formula (7-3) is preferably at least one kind selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-ene-2,3-dicarboximide, N-(trifluoromethylsulfonyloxy)naphthylimide, N-(10-camphorsulfonyloxy) succinimide, N-(10-camphorsulfonyloxy) phthalimide, N-(10-camphorsulfonyloxy)diphenylmaleimide, N-(10-camphorsulfonyloxy)bicyclo[2.2.1]hept-5-ene-2,3-dicarboximide, N-(10-camphorsulfonyloxy) naphthylimide, N-(n-octanesulfonyloxy)bicyclo[2.2.1]hept-5-ene-2,3-dicarboximide, N-(n-octanesulfonyloxy) naphthylimide, N-(p-toluenesulfonyloxy)bicyclo[2.2.1] hept-5-ene-2,3-dicarboximide, N-(p-toluenesulfonyloxy) naphthylimide, N-(2-trifluoromethylbenzenesulfonyloxy) bicyclo[2.2.1]hept-5-ene-2,3-dicarboximide, N-(2-trifluoromethylbenzenesulfonyloxy)naphthylimide, N-(4-trifluoromethylbenzenesulfonyloxy)bicyclo[2.2.1]hept-5-ene-2,3-dicarboximide, N-(4-trifluoromethylbenzenesulfonyloxy)naphthylimide, N-(perfluorobenzenesulfonyloxy)bicyclo[2.2.1]hept-5-ene-2,3-dicarboximide, N-(perfluorobenzenesulfonyloxy)naphthylimide, N-(1-naphthalenesulfonyloxy)bicyclo[2.2.1] hept-5-ene-2,3-dicarboximide, N-(1-naphthalenesulfonyloxy)naphthylimide, N-(nonafluoro-n-butanesulfonyloxy)bicyclo[2.2.1]hept-5-ene-2,3-dicarboximide, N-(nonafluoro-n-butanesulfonyloxy) naphthylimide, N-(perfluoro-n-octanesulfonyloxy)bicyclo [2.2.1]hept-5-ene-2,3-dicarboximide, and N-(perfluoro-n-octanesulfonyloxy)naphthylimide.

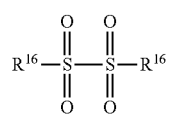

(7-4)

In the formula (7-4), $R^{16}$ may be the same or different and is each independently an optionally substituted linear, branched, or cyclic alkyl group, an optionally substituted aryl group, an optionally substituted heteroaryl group, or an optionally substituted aralkyl group.

The compound represented by the above formula (7-4) is preferably at least one kind selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

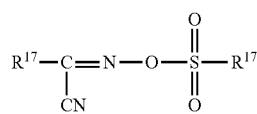

(7-5)

In the formula (7-5), $R^{17}$ may be the same or different and is each independently an optionally substituted linear, branched, or cyclic alkyl group, an optionally substituted aryl group, an optionally substituted heteroaryl group, or an optionally substituted aralkyl group.

The compound represented by the above formula (7-5) is preferably at least one kind selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

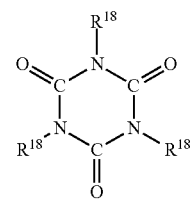

(7-6)

In the formula (7-6), $R^{18}$ may be the same or different and is each independently an alkyl halide group having one or more chlorine atoms and one or more bromine atoms. The alkyl halide group is preferably of 1 to 5 carbon atoms.

Other examples of the acid generating agent include: bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis (isopropylsulfonyl)diazomethane, 1,3-bis (cyclohexylsulfonylazomethylsulfonyl)propane, 1,4-bis (phenylsulfonylazomethylsulfonyl)butane, 1,6-bis (phenylsulfonylazomethylsulfonyl)hexane, and 1,10-bis (cyclohexylsulfonylazomethylsulfonyl)decane; and halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, and tris(2,3-dibromopropyl)-1,3,5-triazine, tris(2,3-dibromopropyl)isocyanurate.

Among the above acid generating agents, an acid generating agent having an aromatic ring is preferable, and an acid generating agent represented by the formula (7-1) or (7-2) is more preferable. An acid generating agent represented by the formula (7-1) or (7-2) wherein $X^-$ has a sulfonate ion having an aryl group or a halogen-substituted aryl group is further preferable, and an acid generating agent represented by the formula (7-1) or (7-2) wherein $X^-$ has a sulfonate ion having an aryl group is particularly preferable.

Diphenyltrimethylphenylsulfonium p-toluenesulfonate, triphenylsulfonium p-toluenesulfonate, triphenylsulfonium trifluoromethanesulfonate, or triphenylsulfonium nonafluoromethanesulfonate is particularly preferable. Use of the acid generating agent can reduce LER.

The acid generating agent (C) can be used alone or in combination of two or more kinds.

[Acid Crosslinking Agent]

In the present embodiment, the resist composition preferably contains one or more acid crosslinking agents (G). The acid crosslinking agent (G) is a compound capable of intramolecularly or intermolecularly crosslinking the compound represented by the formula (1) in the presence of the acid generated from the acid generating agent (C). Examples of such an acid crosslinking agent (G) include a compound having one or more groups (hereinafter, referred to as "crosslinkable group") capable of crosslinking the compound represented by the formula (1).

Specific examples of such a crosslinkable group can include (i) a hydroxyalkyl group such as a hydroxy (C1-C6 alkyl group), a C1-C6 alkoxy (C1-C6 alkyl group), and an acetoxy (C1-C6 alkyl group), or a group derived therefrom; (ii) a carbonyl group such as a formyl group and a carboxy (C1-C6 alkyl group), or a group derived therefrom; (iii) a nitrogenous group-containing group such as a dimethylaminomethyl group, a diethylaminomethyl group, a dimethylolaminomethyl group, a diethylolaminomethyl group, and a morpholinomethyl group; (iv) a glycidyl group-containing group such as a glycidyl ether group, a glycidyl ester group, and a glycidylamino group; (v) a group derived from an aromatic group such as a C1-C6 allyloxy (C1-C6 alkyl group) and a C1-C6 aralkyloxy (C1-C6 alkyl group) such as a benzyloxymethyl group and a benzoyloxymethyl group; and (vi) a polymerizable multiple bond-containing group such as a vinyl group and a isopropenyl group. As the crosslinkable group of the acid crosslinking agent (G) of the present invention, a hydroxyalkyl group and an alkoxyalkyl group or the like are preferable, and an alkoxymethyl group is particularly preferable.

Examples of the acid crosslinking agent (G) having the crosslinkable group can include, but not particularly limited to: (i) methylol group-containing compounds such as methylol group-containing melamine compounds, methylol group-containing benzoguanamine compounds, methylol group-containing urea compounds, methylol group-containing glycoluril compounds, and methylol group-containing phenol compounds; (ii) alkoxyalkyl group-containing compounds such as alkoxyalkyl group-containing melamine compounds, alkoxyalkyl group-containing benzoguanamine compounds, alkoxyalkyl group-containing urea compounds, alkoxyalkyl group-containing glycoluril compounds, and alkoxyalkyl group-containing phenol compounds; (iii) carboxymethyl group-containing compounds such as carboxymethyl group-containing melamine compounds, carboxymethyl group-containing benzoguanamine compounds, carboxymethyl group-containing urea compounds, carboxymethyl group-containing glycoluril compounds, and carboxymethyl group-containing phenol compounds; and (iv) epoxy compounds such as bisphenol A-based epoxy compounds, bisphenol F-based epoxy compounds, bisphenol S-based epoxy compounds, novolac resin-based epoxy compounds, resol resin-based epoxy compounds, and poly(hydroxystyrene)-based epoxy compounds.

As the acid crosslinking agent (G), a compound having a phenolic hydroxy group, and a compound and a resin provided with crosslinkability by introducing the crosslinkable group to an acidic functional group in an alkali soluble resin can be further used. In this case, the rate of introduction of the crosslinkable group is usually adjusted to 5 to 100% by mol, preferably 10 to 60% by mol, and more preferably 15 to 40% by mol based on all acidic functional groups in the compound having a phenolic hydroxy group and the alkali soluble resin. The above range is preferable because crosslinking reaction occurs sufficiently, and a decrease in the film remaining rate, a swelling event and meandering of a pattern, and the like can be avoided.

In the present embodiment, the acid crosslinking agent (G) is preferably an alkoxyalkylated urea compound or a resin thereof, or an alkoxyalkylated glycoluril compound or a resin thereof. Particularly preferable examples of the acid crosslinking agent (G) can include compounds represented by the following formulas (8-1) to (8-3) and alkoxymethylated melamine compounds (acid crosslinking agent (G1)):

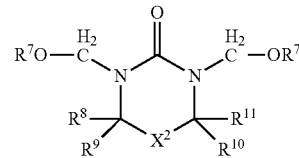
(8-1)

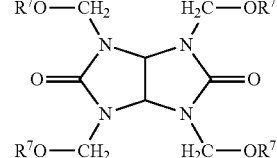
(8-2)

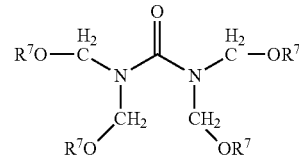
(8-3)

In the above formulas (8-1) to (8-3), each $R^7$ independently represents a hydrogen atom, an alkyl group, or an acyl group; $R^8$ to $R^{11}$ each independently represent a hydrogen atom, a hydroxy group, an alkyl group, or an alkoxyl group; and $X^2$ represents a single bond, a methylene group, or an oxygen atom.

The alkyl group represented by $R^7$ is preferably of 1 to 6 carbon atoms and more preferably of 1 to 3 carbon atoms. Examples thereof include a methyl group, an ethyl group, and a propyl group. The acyl group represented by $R^7$ is preferably of 2 to 6 carbon atoms and more preferably of 2 to 4 carbon atoms. Examples thereof include an acetyl group and a propionyl group. The alkyl group represented by $R^8$ to $R^{11}$ is preferably of 1 to 6 carbon atoms and more preferably of 1 to 3 carbon atoms. Examples thereof include a methyl group, an ethyl group, and a propyl group. The alkoxyl group represented by $R^8$ to $R^{11}$ is preferably of 1 to 6 carbon atoms and more preferably of 1 to 3 carbon atoms. Examples thereof include a methoxy group, an ethoxy group, and a propoxy group. $X^2$ is preferably a single bond or a methylene group. $R^7$ to $R^{11}$ and $X^2$ may be substituted with an alkyl group such as a methyl group or an ethyl group, an alkoxy group such as a methoxy group or an ethoxy group, a hydroxy group, a halogen atom, or the like. A plurality of $R^7$ moieties or $R^8$ to $R^{11}$ moieties may be the same as or different from each other.

Specific examples of the compound represented by the formula (8-1) can include the following compounds:

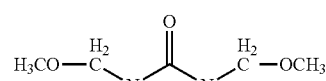

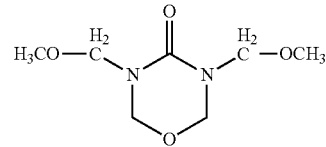

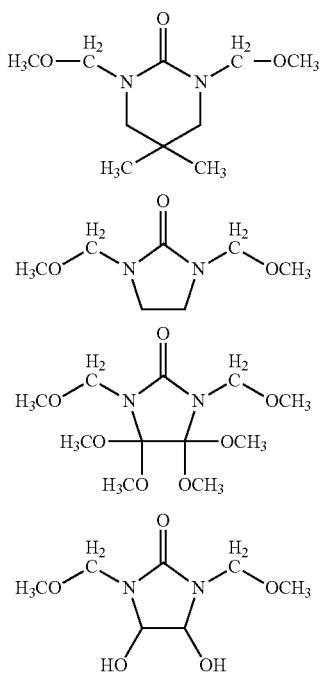

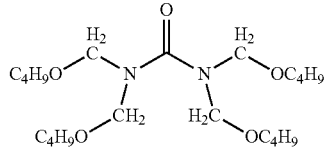

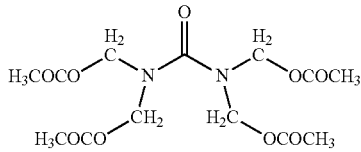

Specific examples of the alkoxymethylated melamine compounds can include N,N,N,N,N,N-hexa(methoxymethyl)melamine, N,N,N,N,N,N-hexa(ethoxymethyl)melamine, N,N,N,N,N,N-hexa(n-propoxymethyl)melamine, N,N,N,N,N,N-hexa(isopropoxymethyl)melamine, N,N,N,N,N,N-hexa(n-butoxymethyl)melamine, and N,N,N,N,N,N-hexa(t-butoxymethyl)melamine. Among them, N,N,N,N,N,N-hexa(methoxymethyl)melamine is preferable.

The acid crosslinking agent (G1) is obtained, for example, by subjecting a urea compound or a glycoluril compound and formalin to condensation reaction for the introduction of a methylol group, then further etherifying the resultant with a lower alcohol such as methyl alcohol, ethyl alcohol, propyl alcohol, or butyl alcohol, subsequently cooling the reaction solution, and recovering the precipitated compound or resin thereof. Alternatively, the acid crosslinking agent (G1) can also be obtained as a commercially available product such as CYMEL (trade name, manufactured by Mitsui-Cyanamid Ltd) or Nikalac (manufactured by Sanwa Chemical Co., Ltd.).

Other particularly preferable examples of the acid crosslinking agent (G) can include a phenol derivative having 1 to 6 benzene rings in the molecule and having two or more groups selected from a hydroxyalkyl group and/or an alkoxyalkyl group in the whole molecule, wherein the hydroxyalkyl group and/or the alkoxyalkyl group is bonded to any of the benzene rings (acid crosslinking agent (G2)). Preferable examples thereof can include a phenol derivative having a molecular weight of 1500 or smaller, having 1 to 6 benzene rings in the molecule, and having a total of two or more groups selected from a hydroxyalkyl group and/or an alkoxyalkyl group, wherein the hydroxyalkyl group and/or the alkoxyalkyl group is bonded to any one or plurality of the benzene rings.

The hydroxyalkyl group bonded to the benzene ring is preferably a hydroxyalkyl group of 1 to 6 carbon atoms such as a hydroxymethyl group, a 2-hydroxyethyl group, or a 2-hydroxy-1-propyl group. The alkoxyalkyl group bonded to the benzene ring is preferably of 2 to 6 carbon atoms. Specifically, a methoxymethyl group, an ethoxymethyl group, a n-propoxymethyl group, an isopropoxymethyl group, a n-butoxymethyl group, an isobutoxymethyl group, a sec-butoxymethyl group, a t-butoxymethyl group, a 2-methoxyethyl group, or a 2-methoxy-1-propyl group is preferable.

Among these phenol derivatives, the following compounds are particularly preferable.

Specific examples of the compound represented by the formula (8-2) can include N,N,N,N-tetra(methoxymethyl)glycoluril, N,N,N,N-tetra(ethoxymethyl)glycoluril, N,N,N,N-tetra(n-propoxymethyl)glycoluril, N,N,N,N-tetra(isopropoxymethyl)glycoluril, N,N,N,N-tetra(n-butoxymethyl)glycoluril, and N,N,N,N-tetra(t-butoxymethyl)glycoluril. Among them, N,N,N,N-tetra(methoxymethyl)glycoluril is particularly preferable.

Specific examples of the compound represented by the formula (8-3) can include the following compounds:

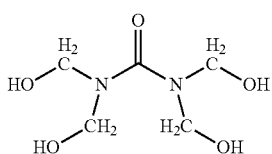

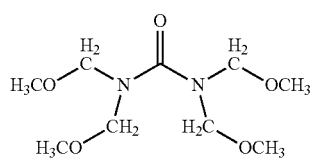

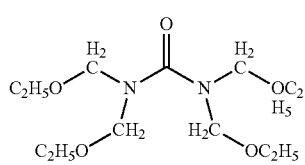

67 68
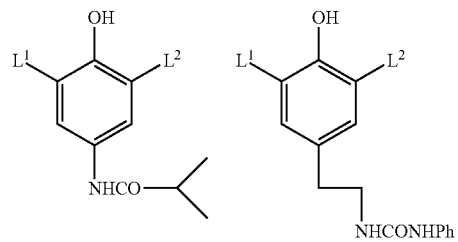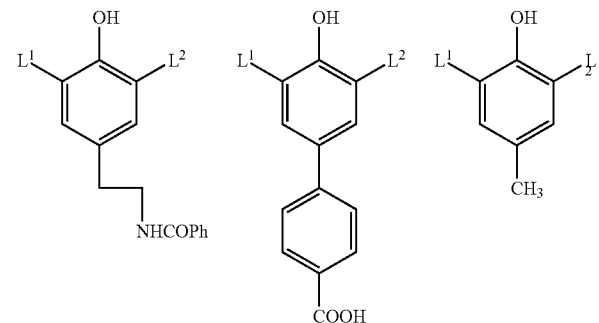
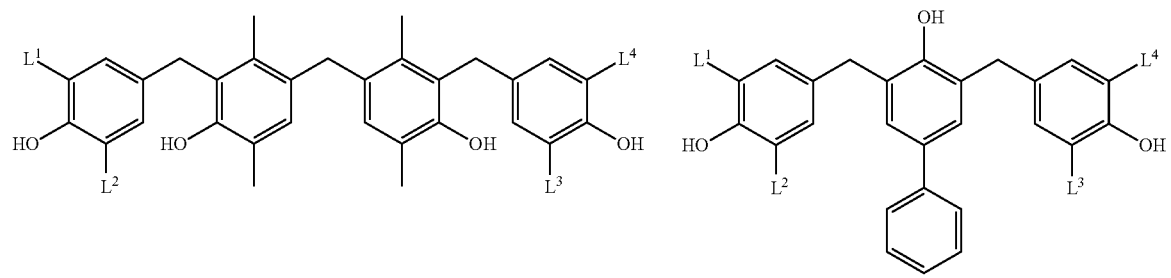
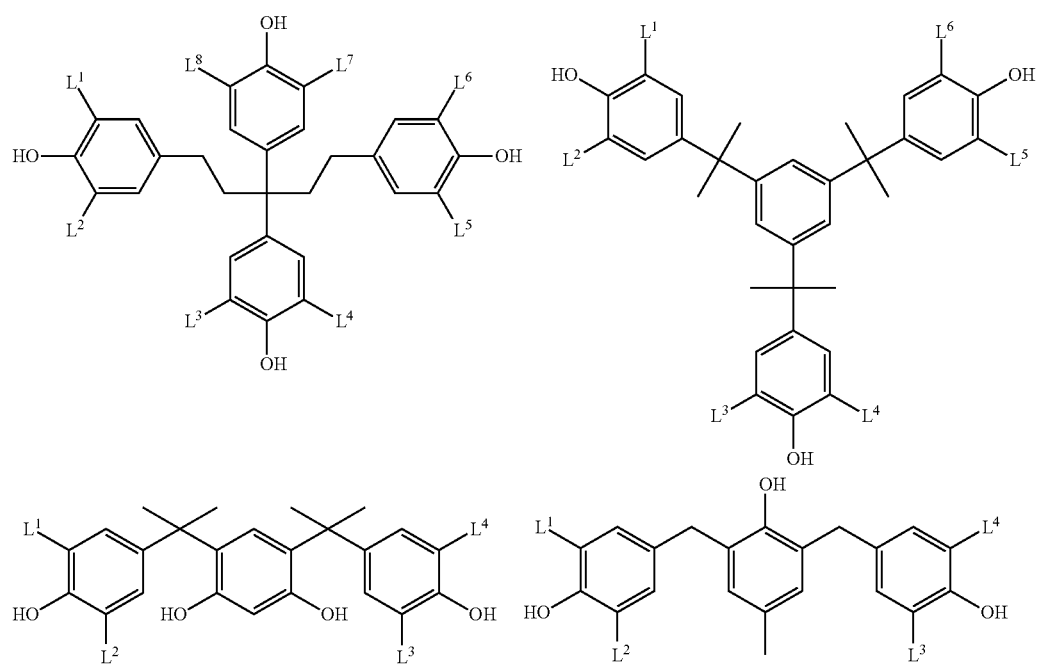
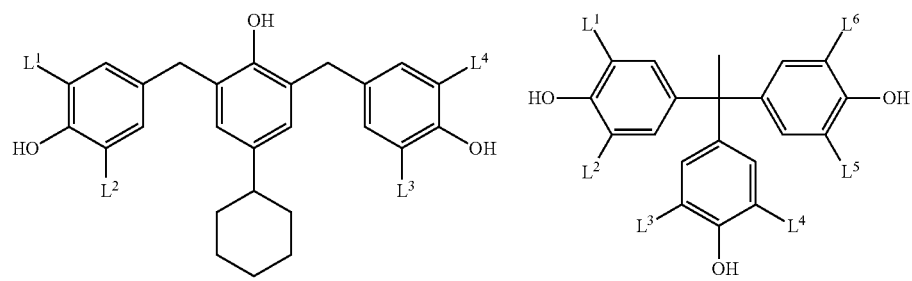

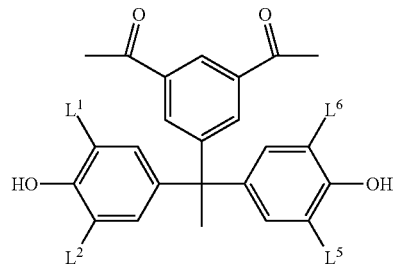
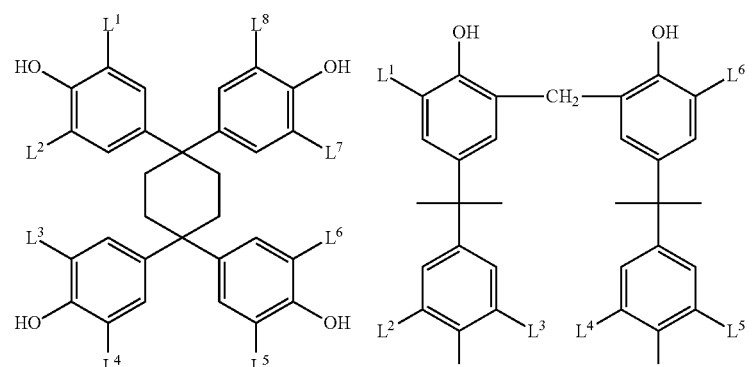
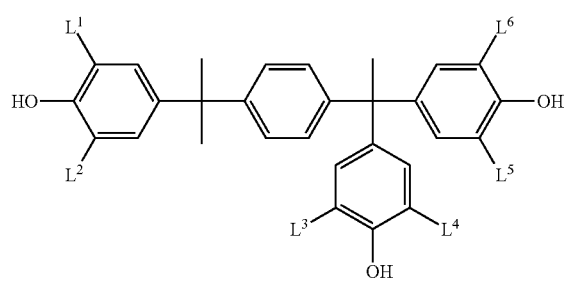
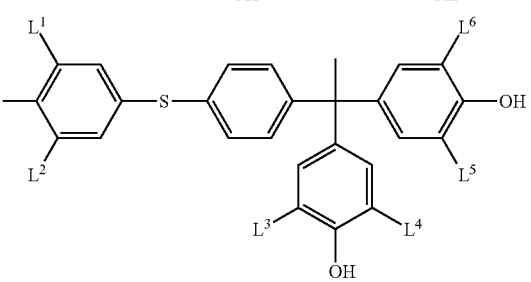
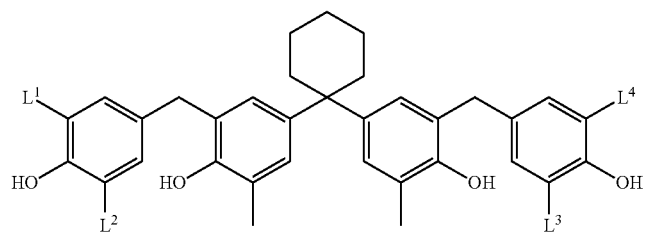
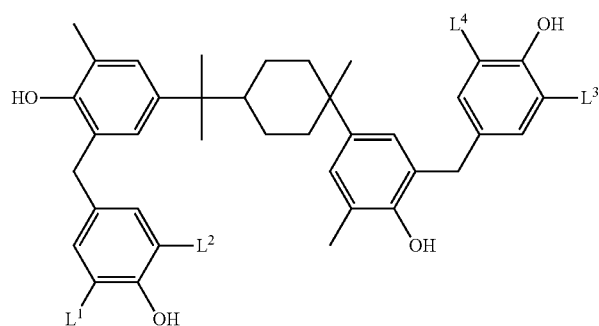
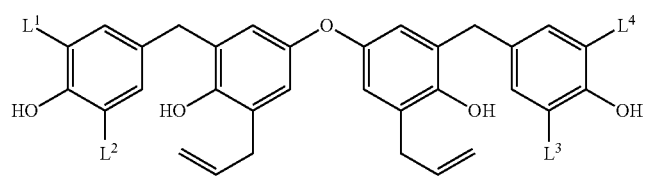
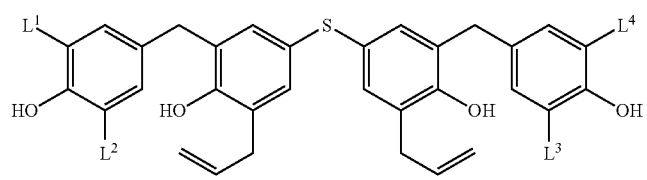

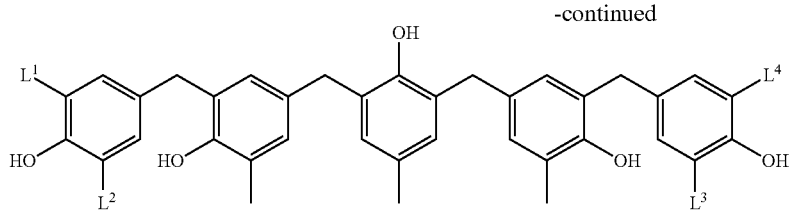

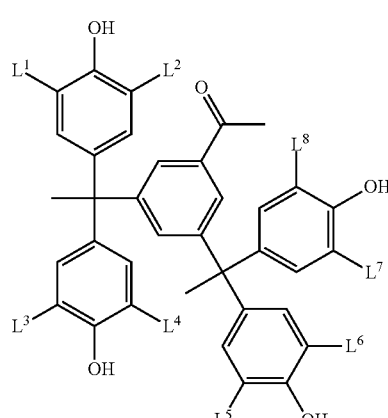

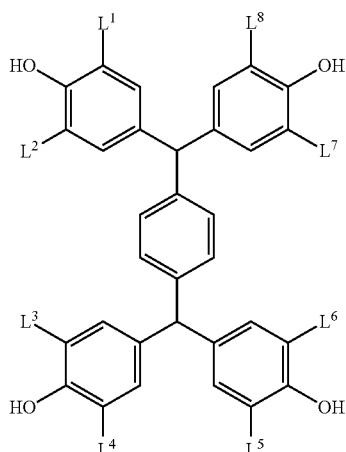

In the above formulas, $L^1$ to $L^8$ may be the same or different and each independently represent a hydroxymethyl group, a methoxymethyl group, or an ethoxymethyl group. The phenol derivative having a hydroxymethyl group can be obtained by reacting a corresponding phenol compound having no hydroxymethyl group (a compound of any of the above formulas wherein each of $L^1$ to $L^8$ is a hydrogen atom) with formaldehyde in the presence of a basic catalyst. This reaction is preferably performed at a reaction temperature of 60° C. or lower in order to prevent resinification or gelation. Specifically, the phenol derivative can be synthesized by a method described in, for example, Japanese Patent Application Laid-Open No. 6-282067 or 7-64285.

The phenol derivative having an alkoxymethyl group can be obtained by reacting a corresponding phenol derivative having a hydroxymethyl group with an alcohol in the presence of an acid catalyst. This reaction is preferably performed at a reaction temperature of 100° C. or lower in order to prevent resinification or gelation. Specifically, the phenol derivative can be synthesized by a method described in, for example, EP632003A1.

The thus-synthesized phenol derivative having a hydroxymethyl group and/or an alkoxymethyl group is preferable from the viewpoint of stability upon storage. The phenol derivative having an alkoxymethyl group is particularly preferable from the viewpoint of stability upon storage. The acid crosslinking agent (G2) may be used alone or may be used in combination of two or more kinds.

Other particularly preferable examples of the acid crosslinking agent (G) can include a compound having at least one α-hydroxyisopropyl group (acid crosslinking agent (G3)). Its structure is not particularly limited as long as the structure has the α-hydroxyisopropyl group. A hydrogen atom of a hydroxyl group in the α-hydroxyisopropyl group may be replaced with one or more acid dissociation groups (a R—COO— group, a R—SO$_2$— group, etc., wherein R represents a substituent selected from the group consisting of a linear hydrocarbon group of 1 to 12 carbon atoms, a cyclic hydrocarbon group of 3 to 12 carbon atoms, an alkoxy group of 1 to 12 carbon atoms, a 1-branched alkyl group of 3 to 12 carbon atoms, and an aromatic hydrocarbon group of 6 to 12 carbon atoms). Examples of the compound having the α-hydroxyisopropyl group include one kind or two or more kinds of substituted or unsubstituted aromatic compounds, diphenyl compounds, naphthalene compounds, furan compounds, and the like containing at least one α-hydroxyisopropyl group. Specific examples thereof include a compound represented by the following formula (9-1) (hereinafter, referred to as a "benzene-based compound (1)"), a compound represented by the following formula (9-2) (hereinafter, referred to as a "diphenyl-based compound (2)"), a compound represented by the following formula (9-3) (hereinafter, referred to as a "naphthalene-based compound (3)"), and a compound represented by the following formula (9-4) (hereinafter, referred to as a "furan-based compound (4)"):

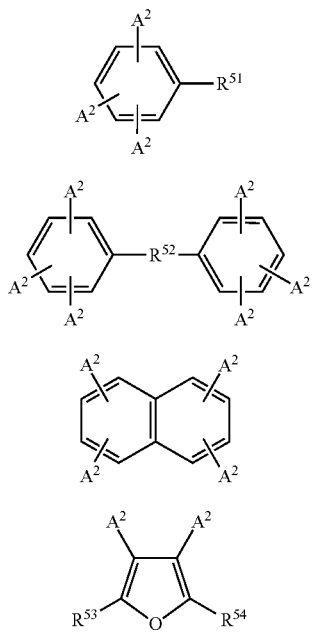

(9-1)
(9-2)
(9-3)
(9-4)

In the above formulas (9-1) to (9-4), each $A^2$ independently represents an α-hydroxyisopropyl group or a hydrogen atom, and at least one $A^2$ is an α-hydroxyisopropyl group. In the formula (9-1), $R^{51}$ represents a hydrogen atom, a hydroxyl group, a linear or branched alkylcarbonyl group of 2 to 6 carbon atoms, or a linear or branched alkoxycarbonyl group of 2 to 6 carbon atoms. In the formula (9-2), $R^{52}$ is a single bond, a linear or branched alkylene group of 1 to 5 carbon atoms, —O—, —CO—, or —COO—. In the formula (9-4), $R^{53}$ and $R^{54}$ each independently represent a hydrogen atom or a linear or branched alkyl group of 1 to 6 carbon atoms.

Specific examples of the benzene-based compound (1) include: α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, and 1,3,5-tris(α-hydroxyisopropyl)benzene; α-hydroxyisopropylphenols such as 3-α-hydroxyisopropylphenol, 4-α-hydroxyisopropylphenol, 3,5-bis(α-hydroxyisopropyl)phenol, and 2,4,6-tris(α-hydroxyisopropyl)phenol; α-hydroxyisopropylphenyl alkyl ketones such as 3-α-hydroxyisopropylphenyl methyl ketone, 4-α-hydroxyisopropylphenyl methyl ketone, 4-α-hydroxyisopropylphenyl ethyl ketone, 4-α-hydroxyisopropylphenyl n-propyl ketone, 4-α-hydroxyisopropylphenyl isopropyl ketone, 4-α-hydroxyisopropylphenyl n-butyl ketone, 4-α-hydroxyisopropylphenyl t-butyl ketone, 4-α-hydroxyisopropylphenyl n-pentyl ketone, 3,5-bis(α-hydroxyisopropyl)phenyl methyl ketone, 3,5-bis(α-hydroxyisopropyl)phenyl ethyl ketone, and 2,4,6-tris(α-hydroxyisopropyl)phenyl methyl ketone; and alkyl 4-α-hydroxyisopropylbenzoates such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, and methyl 2,4,6-tris(α-hydroxyisopropyl)benzoate.

Specific examples of the diphenyl-based compound (2) include: α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6,-tetrakis(α-hydroxyisopropyl)biphenyl, 2,4,4',6,-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl, and 2,2',4,4',6,6'-hexakis(α-hydroxyisopropyl)biphenyl;

α-hydroxyisopropyldiphenylalkanes such as 3-α-hydroxyisopropyldiphenylmethane, 4-α-hydroxyisopropyldiphenylmethane, 1-(4-α-hydroxyisopropylphenyl)-2-phenylethane, 1-(4-α-hydroxyisopropylphenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropylphenyl)-5-phenylpentane, 3,5-bis(α-hydroxyisopropyl)diphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-tris(α-hydroxyisopropyl)diphenylmethane, 3,3',5-tris(α-hydroxyisopropyl)diphenylmethane, 3,4',5-tris(α-hydroxyisopropyl)diphenylmethane, 2,3',4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3',4,5',6-pentakis(α-hydroxyisopropyl)diphenylmethane, and 2,2',4,4',6,6'-hexakis(α-hydroxyisopropyl)diphenylmethane;

α-hydroxyisopropyldiphenyl ethers such as 3-α-hydroxyisopropyldiphenyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4',6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, and 2,2',4,4',6,6'-hexakis(α-hydroxyisopropyl)diphenyl ether;

α-hydroxyisopropyldiphenyl ketones such as 3-α-hydroxyisopropyldiphenyl ketone, 4-α-hydroxyisopropyldiphenyl ketone, 3,5-bis(α-hydroxyisopropyl)diphenyl ketone, 3,3'-bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl)diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, and 2,2',4,4',6,6'-hexakis(α-hydroxyisopropyl)diphenyl ketone; and phenyl α-hydroxyisopropylbenzoates such as phenyl 3-α- hydroxyisopropylbenzoate, phenyl 4-α-hydroxyisopropylbenzoate, 3-α-hydroxyisopropylphenyl benzoate, 4-α-hydroxyisopropylphenyl benzoate, phenyl 3,5-bis(α-hydroxyisopropyl)benzoate, 3-α-hydroxyisopropylphenyl 3-α-hydroxyisopropylbenzoate, 4-α-hydroxyisopropylphenyl 3-α-hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α-hydroxyisopropyl)phenyl benzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris(α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate.

Specific examples of the naphthalene-based compound (3) include 1-(α-hydroxyisopropyl)naphthalene, 2-(α-hydroxyisopropyl)naphthalene, 1,3-bis(α-hydroxyisopropyl)naphthalene, 1,4-bis(α-hydroxyisopropyl)naphthalene, 1,5-bis(α-hydroxyisopropyl)naphthalene, 1,6-bis(α-hydroxyisopropyl)naphthalene, 1,7-bis(α-hydroxyisopropyl)naphthalene, 2,6-bis(α-hydroxyisopropyl)naphthalene, 2,7-bis(α-hydroxyisopropyl)naphthalene, 1,3,5-tris(α-hydroxyisopropyl)naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, and 1,3,5,7-tetrakis(α-hydroxyisopropyl)naphthalene.

Specific examples of the furan-based compound (4) can include 3-(α-hydroxyisopropyl)furan, 2-methyl-3-(α-hydroxyisopropyl)furan, 2-methyl-4-(α-hydroxyisopropyl)furan, 2-ethyl-4-(α-hydroxyisopropyl)furan, 2-n-propyl-4-(α-hydroxyisopropyl)furan, 2-isopropyl-4-(α-hydroxyisopropyl)furan, 2-n-butyl-4-(α-hydroxyisopropyl)furan, 2-t-butyl-4-(α-hydroxyisopropyl)furan, 2-n-pentyl-4-(α-hydroxyisopropyl)furan, 2,5-dimethyl-3-(α-hydroxyisopropyl)furan, 2,5-diethyl-3-(α-hydroxyisopropyl)furan, 3,4-bis(α-hydroxyisopropyl)furan, 2,5-dimethyl-3,4-bis(α-hydroxyisopropyl)furan, and 2,5-diethyl-3,4-bis(α-hydroxyisopropyl)furan.

The acid crosslinking agent (G3) is preferably a compound having two or more free α-hydroxyisopropyl groups, more preferably the benzene-based compound (1) having two or more α-hydroxyisopropyl groups, the diphenyl-based compound (2) having two or more α-hydroxyisopropyl groups, or the naphthalene-based compound (3) having two or more α-hydroxyisopropyl groups, and particularly preferably an α-hydroxyisopropylbiphenyl having two or more α-hydroxyisopropyl groups or the naphthalene-based compound (3) having two or more α-hydroxyisopropyl groups.

The acid crosslinking agent (G3) can usually be obtained by a method of reacting an acetyl group-containing compound such as 1,3-diacetylbenzene with a Grignard reagent such as $CH_3MgBr$ for methylation, followed by hydrolysis, or a method of oxidizing an isopropyl group-containing compound such as 1,3-diisopropylbenzene with oxygen or the like to form a peroxide, followed by reduction.

In the present embodiment, the amount of the acid crosslinking agent (G) used is preferably 0.5 to 49% by mass of the total weight of the solid components, more preferably 0.5 to 40% by mass, still more preferably 1 to 30% by mass, and particularly preferably 2 to 20% by mass. When the content ratio of the above acid crosslinking agent (G) is 0.5% by mass or more, the inhibiting effect of the solubility of a resist film in an alkaline developing solution is improved, and a decrease in the film remaining rate, and occurrence of swelling and meandering of a pattern can be inhibited, which is preferable. On the other hand, when the content is 50% by mass or less, a decrease in heat resistance as a resist can be inhibited, which is preferable.

The content ratio of at least one compound selected from the acid crosslinking agent (G1), the acid crosslinking agent (G2), and the acid crosslinking agent (G3) in the acid crosslinking agent (G) is not particularly limited and can be in various ranges depending on the kind of a substrate used upon forming a resist pattern, etc.

In all acid crosslinking agent components, the content of the alkoxymethylated melamine compound and/or the compounds represented by the formula (9-1) to the formula (9-3) is 50 to 99% by mass, preferably 60 to 99% by mass, more preferably 70 to 98% by mass, and further preferably 80 to 97% by mass. 50% by mass or more of the alkoxymethylated melamine compound and/or the compounds represented by the formula (9-1) to the formula (9-3) in all acid crosslinking agent components is preferable because resolution can be improved. 99% by mass or less thereof is preferable because a rectangular cross sectional shape is easily obtained as the cross sectional shape of a pattern.

[Acid Diffusion Controlling Agent]

In the present embodiment, the resist composition may contain an acid diffusion controlling agent (E) having a function of controlling diffusion of an acid generated from an acid generating agent by radiation irradiation in a resist film to inhibit any unpreferable chemical reaction in an unexposed region or the like. By using such an acid diffusion controlling agent (E), the storage stability of a resist composition is improved. Also, along with the improvement of the resolution, the line width change of a resist pattern due to variation in the post exposure delay time before radiation irradiation and the post exposure delay time after radiation irradiation can be inhibited, and the composition has extremely excellent process stability. Examples of such an acid diffusion controlling agent (E) include a radiation degradable basic compound such as a nitrogen atom-containing basic compound, a basic sulfonium compound, and a basic iodonium compound. The acid diffusion controlling agent (E) can be used alone or in combination of two or more kinds.

Examples of the acid diffusion controlling agent include nitrogen-containing organic compounds and basic compounds that are degraded by exposure. Examples of the nitrogen-containing organic compounds can include a compound represented by the following formula (10):

(10)

(hereinafter, referred to as a "nitrogen-containing compound (I)"), a diamino compound having two nitrogen atoms in one molecule (hereinafter, referred to as "nitrogen-containing compound (II)"), a polyamino compound or a polymer having three or more nitrogen atoms (hereinafter, referred to as a "nitrogen-containing compound (III)"), amide group-containing compounds, urea compounds, and nitrogen-containing heterocyclic compounds. These acid diffusion controlling agents (E) may be used alone as one kind or may be used in combination of two or more kinds.

In the above formula (10), $R^{61}$, $R^{62}$, and $R^{63}$ each independently represent a hydrogen atom, a linear, branched, or cyclic alkyl group, an aryl group, or an aralkyl group. The alkyl group, the aryl group, or the aralkyl group may be unsubstituted or may be substituted with a hydroxyl group or the like. Herein, examples of the linear, branched, or cyclic alkyl group include alkyl groups of 1 to 15 carbon atoms and preferably of 1 to 10 carbon atoms and specifically include a methyl group, an ethyl group, a n-propyl group, an isopropyl group, a n-butyl group, an isobutyl group, a sec-butyl group, a t-butyl group, a n-pentyl group, a neopentyl group, a n-hexyl group, a thexyl group, a n-heptyl group, a n-octyl group, a n-ethylhexyl group, a n-nonyl group, and a n-decyl group. Examples of the aryl group include aryl groups of 6 to 12 carbon atoms and specifically include a phenyl group, a tolyl group, a xylyl group, a cumenyl group, and a 1-naphthyl group. Examples of the aralkyl group include aralkyl groups of 7 to 19 carbon atoms and preferably of 7 to 13 carbon atoms and specifically include a benzyl group, an α-methylbenzyl group, a phenethyl group, and a naphthylmethyl group.

Specific examples of the nitrogen-containing compound (I) can include: mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylamine, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Specific examples of the nitrogen-containing compound (II) can include ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Specific examples of the nitrogen-containing compound (III) can include polyethylenimine, polyallylamine, and polymers of N-(2-dimethylaminoethyl)acrylamide.

Specific examples of the amide group-containing compounds can include formamide, N-methylformamide, N,N-dimethylformamide, acetamide, N-methylacetamide, N,N-dimethylacetamide, propionamide, benzamide, pyrrolidone, and N-methylpyrrolidone.

Specific examples of the urea compounds can include urea, methylurea, 1,1-dimethylurea, 1,3-dimethylurea, 1,1,3,3-tetramethylurea, 1,3-diphenylurea, and tri-n-butylthiourea.

Specific examples of the nitrogen-containing heterocyclic compounds can include: imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinic acid amide, quinoline, 8-oxyquinoline, and acridine; and pyrazine, pyrazole, pyridazine, quinozaline, purine, pyrrolidine, piperidine, morpholine, 4-methylmorpholine, piperazine, 1,4-dimethylpiperazine, and 1,4-diazabicyclo[2.2.2]octane.

Examples of the radiation degradable basic compound can include a sulfonium compound represented by the following formula (11-1):

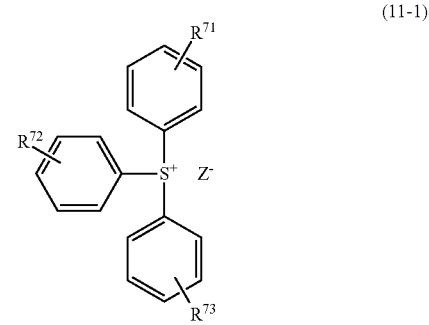

(11-1)

and an iodonium compound represented by the following formula (11-2):

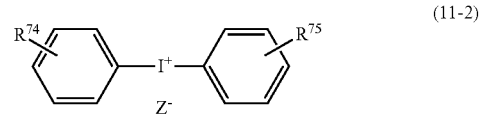

(11-2)

In the above formulas (11-1) and (11-2), $R^{71}$, $R^{72}$, $R^{73}$, $R^{74}$, and $R^{75}$ each independently represent a hydrogen atom, an alkyl group of 1 to 6 carbon atoms, an alkoxyl group of 1 to 6 carbon atoms, a hydroxyl group, or a halogen atom. $Z^-$ represents $HO^-$, $R-COO^-$ (wherein R is an alkyl group of 1 to 6 carbon atoms, an aryl group of 6 to 11 carbon atoms, or an alkaryl group of 7 to 12 carbon atoms), or an anion represented by the following formula (11-3):

(11-3)

Specific examples of the radiation degradable basic compound include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The content of the acid diffusion controlling agent (E) is preferably 0.001 to 49% by mass of the total weight of the solid component, more preferably 0.01 to 10% by mass, still more preferably 0.01 to 5% by mass, and particularly preferably 0.01 to 3% by mass. Within the above range, a decrease in resolution, and deterioration of the pattern shape and the dimension fidelity or the like can be prevented. Moreover, even though the post exposure delay time from electron beam irradiation to heating after radiation irradiation becomes longer, the shape of the pattern upper layer portion does not deteriorate. When the content is 10% by mass or less, a decrease in sensitivity, and developability of the unexposed portion or the like can be prevented. By using such an acid diffusion controlling agent, the storage stability of a resist composition improves, also along with improvement of the resolution, the line width change of a resist pattern due to variation in the post exposure delay time before radiation irradiation and the post exposure delay time after radiation irradiation can be inhibited, and the composition is extremely excellent process stability.

To the resist composition of the present embodiment, if required, as the further component (F), one kind or two kinds or more of various additive agents such as a dissolution promoting agent, a dissolution controlling agent, a sensitizing agent, a surfactant, and an organic carboxylic acid or an oxo acid of phosphor or derivative thereof can be added within the range not inhibiting the objects of the present invention.

[Dissolution Promoting Agent]

A low molecular weight dissolution promoting agent is a component having a function of increasing the solubility of a compound represented by the formula (1) in a developing solution to moderately increase the dissolution rate of the compound upon developing, when the solubility of the compound is too low. The low molecular weight dissolution promoting agent can be used within the range not deteriorating the effect of the present invention. Examples of the above dissolution promoting agent can include low molecular weight phenolic compounds, such as bisphenols and tris(hydroxyphenyl)methane. These dissolution promoting agents can be used alone or in mixture of two or more kinds. The content of the dissolution promoting agent, which is arbitrarily adjusted according to the kind of the compound to be used, is preferably 0 to 49% by mass of the total weight of the solid component, more preferably 0 to 5% by mass, still more preferably 0 to 1% by mass, and particularly preferably 0% by mass.

[Dissolution Controlling Agent]

The dissolution controlling agent is a component having a function of controlling the solubility of the compound represented by the formula (1) in a developing solution to moderately decrease the dissolution rate upon developing, when the solubility of the compound is too high. As such a dissolution controlling agent, the one which does not chemically change in steps such as calcination of resist coating, radiation irradiation, and development is preferable.

The dissolution controlling agent is not particularly limited, and examples can include aromatic hydrocarbons such as phenanthrene, anthracene, and acenaphthene; ketones such as acetophenone, benzophenone, and phenyl naphthyl ketone; and sulfones such as methyl phenyl sulfone, diphenyl sulfone, and dinaphthyl sulfone. These dissolution controlling agents can be used alone or in two or more kinds. The content of the dissolution controlling agent, which is arbitrarily adjusted according to the kind of the compound to be used, is preferably 0 to 49% by mass of the total weight of the solid component, more preferably 0 to 5% by mass, still more preferably 0 to 1% by mass, and particularly preferably 0% by mass.

[Sensitizing Agent]

The sensitizing agent is a component having a function of absorbing irradiated radiation energy, transmitting the energy to the acid generating agent (C), and thereby increasing the acid production amount, and improving the apparent sensitivity of a resist. Such a sensitizing agent is not particularly limited, and examples can include benzophenones, biacetyls, pyrenes, phenothiazines, and fluorenes. These sensitizing agents can be used alone or in two or more kinds. The content of the sensitizing agent, which is arbitrarily adjusted according to the kind of the compound to be used, is preferably 0 to 49% by mass of the total weight of the solid component, more preferably 0 to 5% by mass, still more preferably 0 to 1% by mass, and particularly preferably 0% by mass.

[Surfactant]

The surfactant is a component having a function of improving coatability and striation of the resist composition of the present invention, and developability of a resist or the like. Such a surfactant may be any of anionic, cationic, nonionic, and amphoteric surfactants. A preferable surfactant is a nonionic surfactant. The nonionic surfactant has a good affinity with a solvent used in production of resist compositions and more effects. Examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products include, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.). The content of the surfactant, which is arbitrarily adjusted according to the kind of the compound to be used, is preferably 0 to 49% by mass of the total weight of the solid component, more preferably 0 to 5% by mass, still more preferably 0 to 1% by mass, and particularly preferably 0% by mass.

[Organic Carboxylic Acid or Oxo Acid of Phosphor or Derivative Thereof]

For the purpose of prevention of sensitivity deterioration or improvement of a resist pattern shape and post exposure delay stability or the like, and as an additional optional component, the resist composition of the present embodiment can contain an organic carboxylic acid or an oxo acid of phosphor or derivative thereof. The organic carboxylic acid or an oxo acid of phosphor or derivative thereof can be used in combination with the acid diffusion controlling agent, or may be used alone. The organic carboxylic acid is, for example, suitably malonic acid, citric acid, malic acid, succinic acid, benzoic acid, salicylic acid, or the like. Examples of the oxo acid of phosphor or derivative thereof include phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among these, phosphonic acid is particularly preferable.

The organic carboxylic acid or the oxo acid of phosphor or derivative thereof can be used alone or in combination of two or more kinds. The content of the organic carboxylic acid or the oxo acid of phosphor or derivative thereof, which is arbitrarily adjusted according to the kind of the compound to be used, is preferably 0 to 49% by mass of the total weight of the solid component, more preferably 0 to 5% by mass, still more preferably 0 to 1% by mass, and particularly preferably 0% by mass.

[Further Additive Agent Other than Above Additive Agents (Dissolution Promoting Agent, Dissolution Controlling Agent, Sensitizing Agent, Surfactant, and Organic Carboxylic Acid or Oxo Acid of Phosphor or Derivative Thereof)]

Furthermore, within the range not inhibiting the objects of the present invention, the resist composition of the present embodiment can contain one kind or two kinds or more of additive agents other than the above dissolution controlling agent, sensitizing agent, and surfactant if required. Examples of such an additive agent include a dye, a pigment, and an adhesion aid. For example, the composition contains the dye or the pigment, and thereby a latent image of the exposed portion is visualized and influence of halation upon exposure can be alleviated, which is preferable. The composition contains the adhesion aid, and thereby adhesiveness to a substrate can be improved, which is preferable. Furthermore, examples of other additive agent can include a halation preventing agent, a storage stabilizing agent, a defoaming agent, and a shape improving agent. Specific examples thereof can include 4-hydroxy-4'-methylchalkone.

In the resist composition of the present embodiment, the total content of the optional component (F) is preferably 0 to 99% by mass of the total weight of the solid component, more preferably 0 to 49% by mass, still more preferably 0 to 10% by mass, further preferably 0 to 5% by mass, still further preferably 0 to 1% by mass, and particularly preferably 0% by mass.

[Content Ratio of Each Component]

In the resist composition of the present embodiment, the content of the compound represented by the above formula (1) and/or the resin comprising the compound as a constituent is not particularly limited, but is preferably 50 to 99.4% by mass of the total mass of the solid components (summation of solid components including the compound represented by the formula (1), the resin having the compound represented by the formula (1) as a constituent, and optionally used components such as acid generating agent (C), acid crosslinking agent (G), acid diffusion controlling agent (E), and further component (F) (also referred to as "optional component (F)"), hereinafter the same), more preferably 55 to 90% by mass, still more preferably 60 to 80% by mass, and particularly preferably 60 to 70% by mass. In the case of the above content, resolution is further improved, and line edge roughness (LER) is further decreased.

When both of the compound represented by the above formula (1) and the resin comprising the compound as a constituent are contained, the above content refers to the total amount of the compound represented by the above formula (1) and the resin comprising the compound as a constituent.

In the resist composition of the present embodiment, the contents of the compound represented by the above formula (1) and/or the resin comprising the compound as a constituent (hereinafter, also referred to as a component (A)), the acid generating agent (C), the acid crosslinking agent (G), the acid diffusion controlling agent (E), and the optional component (F) (the component (A)/the acid generating agent (C)/the acid crosslinking agent (G)/the acid diffusion controlling agent (E)/the optional component (F)) are preferably 50 to 99.4/0.001 to 49/0.5 to 49/0.001 to 49/0 to 49, more preferably 55 to 90/1 to 40/0.5 to 40/0.01 to 10/0 to 5, further preferably 60 to 80/3 to 30/1 to 30/0.01 to 5/0 to 1, and particularly preferably 60 to 70/10 to 25/2 to 20/0.01 to 3/0% by mass based on solid matter.

The content ratio of each component is selected from each range so that the summation thereof is 100% by mass. By the above content ratio, performance such as sensitivity, resolution, and developability is excellent.

The resist composition of the present embodiment is generally prepared by dissolving each component in a solvent upon use into a homogeneous solution, and then if required, filtering through a filter or the like with a pore diameter of about 0.2 µm, for example.

The resist composition of the present embodiment can contain an additional resin other than the resin of the present embodiment, within the range not inhibiting the objects of the present invention. Examples of the resin include, but not particularly limited to, a novolac resin, polyvinyl phenols, polyacrylic acid, polyvinyl alcohol, a styrene-maleic anhydride resin, and polymers containing an acrylic acid, vinyl alcohol or vinylphenol as a monomeric unit, and derivatives thereof. The content of the resin is not particularly limited and is arbitrarily adjusted according to the kind of the component (A) to be used, and is preferably 30 parts by mass or less per 100 parts by mass of the component (A), more preferably 10 parts by mass or less, still more preferably 5 parts by mass or less, and particularly preferably 0 part by mass.

[Physical Properties and the Like of Resist Composition]

The resist composition of the present embodiment can form an amorphous film by spin coating. Also, the resist composition of the present embodiment can be applied to a general semiconductor production process. Any of positive type and negative type resist patterns can be individually prepared depending on the kind of a developing solution to be used.

In the case of a positive type resist pattern, the dissolution rate of the amorphous film formed by spin coating with the resist composition of the present embodiment in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the compound represented by the above formula (1) and/or the resin comprising the compound as a constituent, contrast at the interface between the exposed portion being dissolved in a developing solution and the unexposed portion not being dissolved in a developing solution is increased. Also, there are effects of reducing LER and defects.

In the case of a negative type resist pattern, the dissolution rate of the amorphous film formed by spin coating with the resist composition of the present embodiment in a developing solution at 23° C. is preferably 10 angstrom/sec or more. When the dissolution rate is 10 angstrom/sec or more, the amorphous film more easily dissolves in a developing solution, and is more suitable for a resist. When the amorphous film has a dissolution rate of 10 angstrom/sec or more, the resolution may improve. It is presumed that this is because the micro surface portion of the compound represented by the above formula (1) and/or the resin comprising the compound as a constituent dissolves, and LER is reduced. Also, there are effects of reducing defects.

The dissolution rate can be determined by immersing the amorphous film in a developing solution for a predetermined period of time at 23° C. and then measuring the film thickness before and after immersion by a publicly known method such as visual, ellipsometric, or QCM method.

In the case of a positive type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 10 angstrom/sec or more. When the dissolution rate is 10 angstrom/sec or more, the amorphous film more easily dissolves in a developing solution, and is more suitable for a resist. When the amorphous film has a dissolution rate of 10 angstrom/sec or more, the resolution may improve. It is presumed that this is because the micro surface portion of the compound represented by the above formula (1) and/or the resin comprising the compound as a constituent dissolves, and LER is reduced. Also, there are effects of reducing defects.

In the case of a negative type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the compound represented by the above formula (1) and/or the resin comprising the compound as a constituent, contrast at the interface between the unexposed portion being dissolved in a developing solution and the exposed portion not being dissolved in a developing solution is increased. Also, there are effects of reducing LER and defects.

[Radiation-Sensitive Composition]

The component (A) to be contained in the radiation-sensitive composition of the present embodiment is used in combination with the optically active diazonaphthoquinone compound (B) mentioned later and is useful as a base material for positive type resists that becomes a compound easily soluble in a developing solution by irradiation with g-ray, h-ray, i-ray, KrF excimer laser, ArF excimer laser, extreme ultraviolet, electron beam, or X-ray. Although the properties of the component (A) are not largely altered by g-ray, h-ray, i-ray, KrF excimer laser, ArF excimer laser, extreme ultraviolet, electron beam, or X-ray, the optically active diazonaphthoquinone compound (B) poorly soluble in a developing solution is converted to an easily soluble compound so that a resist pattern can be formed in a development step.

Since the component (A) to be contained in the radiation-sensitive composition of the present embodiment is a relatively low molecular weight compound as shown in the above formula (1), the obtained resist pattern has very small roughness. In the above formula (1), at least one selected from the group consisting of $R^1$ to $R^5$ is preferably a group containing an iodine atom. In the case of applying the component (A) having such a group containing an iodine atom which is a preferable form to the radiation-sensitive composition of the present embodiment, the ability to absorb radiation such as electron beam, extreme ultraviolet (EUV), or X-ray is increased. As a result, this enables the enhancement of the sensitivity, which is very preferable.

The glass transition temperature of the component (A) to be contained in the radiation-sensitive composition of the present embodiment is preferably 100° C. or higher, more preferably 120° C. or higher, still more preferably 140° C. or higher, and particularly preferably 150° C. or higher. The upper limit of the glass transition temperature of the component (A) is not particularly limited and is, for example, 400° C. When the glass transition temperature of the component (A) falls within the above range, the resulting radiation-sensitive composition has heat resistance capable of maintaining a pattern shape in a semiconductor lithography process, and improves performance such as high resolution.

The heat of crystallization determined by the differential scanning calorimetry of the glass transition temperature of the component (A) to be contained in the radiation-sensitive composition of the present embodiment is preferably less than 20 J/g. (Crystallization temperature)–(Glass transition temperature) is preferably 70° C. or more, more preferably 80° C. or more, still more preferably 100° C. or more, and particularly preferably 130° C. or more. When the heat of crystallization is less than 20 J/g or (Crystallization temperature)–(Glass transition temperature) falls within the above range, the radiation-sensitive composition easily forms an amorphous film by spin coating, can maintain film formability necessary for a resist over a long period, and can improve resolution.

In the present embodiment, the above heat of crystallization, crystallization temperature, and glass transition temperature can be determined by differential scanning calorimetry using "DSC/TA-50WS" manufactured by Shimadzu Corp. For example, about 10 mg of a sample is placed in an unsealed container made of aluminum, and the temperature is raised to the melting point or more at a temperature increase rate of 20° C./min in a nitrogen gas stream (50 mL/min). After quenching, again the temperature is raised to the melting point or more at a temperature increase rate of 20° C./min in a nitrogen gas stream (30 mL/min). After further quenching, again the temperature is raised to 400° C. at a temperature increase rate of 20° C./min in a nitrogen gas stream (30 mL/min). The temperature at the middle point (where the specific heat is changed into the half) of steps in the baseline shifted in a step-like pattern is defined as the glass transition temperature (Tg). The temperature of the subsequently appearing exothermic peak is defined as the crystallization temperature. The heat is determined from the area of a region surrounded by the exothermic peak and the baseline and defined as the heat of crystallization.

The component (A) to be contained in the radiation-sensitive composition of the present embodiment is preferably low sublimable at 100° C. or lower, preferably 120° C. or lower, more preferably 130° C. or lower, still more preferably 140° C. or lower, and particularly preferably 150° C. or lower at normal pressure. The low sublimability means that in thermogravimetry, weight reduction when the resist base material is kept at a predetermined temperature for 10 minutes is 10% or less, preferably 5% or less, more preferably 3% or less, still more preferably 1% or less, and particularly preferably 0.1% or less. The low sublimability can prevent an exposure apparatus from being contaminated by outgassing upon exposure. In addition, a good pattern shape with low roughness can be obtained.

The component (A) to be contained in the radiation-sensitive composition of the present embodiment dissolves at preferably 1% by mass or more, more preferably 5% by mass or more, and still more preferably 10% by mass or more at 23° C. in a solvent that is selected from propylene glycol monomethyl ether acetate (PGMEA), propylene glycol monomethyl ether (PGME), cyclohexanone (CHN), cyclopentanone (CPN), 2-heptanone, anisole, butyl acetate, ethyl propionate, and ethyl lactate and exhibits the highest ability to dissolve the component (A). Particularly preferably, the component (A) dissolves at 20% by mass or more at 23° C. in a solvent that is selected from PGMEA, PGME, and CHN and exhibits the highest ability to dissolve the resist base material (A). Particularly preferably, the component (A) dissolves at 20% by mass or more at 23° C. in PGMEA. When the above conditions are met, the radiation-sensitive composition is easily used in a semiconductor production process at a full production scale.

[Optically Active Diazonaphthoquinone Compound (B)]

The optically active diazonaphthoquinone compound (B) to be contained in the radiation-sensitive composition of the present embodiment is a diazonaphthoquinone substance including a polymer or non-polymer optically active diazonaphthoquinone compound and is not particularly limited as long as it is generally used as a photosensitive component (sensitizing agent) in positive type resist compositions. One kind or two or more kinds can be optionally selected and used.

Such a sensitizing agent is preferably a compound obtained by reacting naphthoquinonediazide sulfonic acid chloride, benzoquinonediazide sulfonic acid chloride, or the like with a low molecular weight compound or a high molecular weight compound having a functional group condensable with these acid chlorides. Herein, examples of the above functional group condensable with the acid chlorides include, but not particularly limited to, a hydroxyl group and an amino group. Particularly, a hydroxyl group is preferable. Examples of the compound containing a hydroxyl group condensable with the acid chlorides can include, but not particularly limited to, hydroquinone, resorcin, hydroxybenzophenones such as 2,4-dihydroxybenzophenone, 2,3,4-trihydroxybenzophenone, 2,4,6-trihydroxybenzophenone, 2,4,4'-trihydroxybenzophenone, 2,3,4,4'-tetrahydroxybenzophenone, 2,2',4,4'-tetrahydroxybenzophenone, and 2,2',3,4,6'-pentahydroxybenzophenone, hydroxyphenylalkanes such as bis(2,4-dihydroxyphenyl)methane, bis(2,3,4-trihydroxyphenyl)methane, and bis(2,4-dihydroxyphenyl)propane, and hydroxytriphenylmethanes such as 4,4',3",4"-tetrahydroxy-3,5,3',5'-tetramethyltriphenylmethane and 4,4',2",3",4"-pentahydroxy-3,5,3',5'-tetramethyltriphenylmethane.

Preferable examples of the acid chloride such as naphthoquinonediazide sulfonic acid chloride or benzoquinonediazide sulfonic acid chloride include 1,2-naphthoquinonediazide-5-sulfonyl chloride and 1,2-naphthoquinonediazide-4-sulfonyl chloride.

The radiation-sensitive composition of the present embodiment is preferably prepared by, for example, dissolving each component in a solvent upon use into a homogeneous solution, and then if required, filtering through a filter or the like with a pore diameter of about 0.2 μm, for example.

[Properties of Radiation-Sensitive Composition]

The radiation-sensitive composition of the present embodiment can form an amorphous film by spin coating. Also, the radiation-sensitive composition of the present embodiment can be applied to a general semiconductor production process. Any of positive type and negative type resist patterns can be individually prepared depending on the kind of a developing solution to be used.

In the case of a positive type resist pattern, the dissolution rate of the amorphous film formed by spin coating with the radiation-sensitive composition of the present embodiment in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the compound represented by the above formula (1) and/or the resin comprising the compound as a constituent, contrast at the interface between the exposed portion being dissolved in a developing solution and the unexposed portion not being dissolved in a developing solution is increased. Also, there are effects of reducing LER and defects.

In the case of a negative type resist pattern, the dissolution rate of the amorphous film formed by spin coating with the radiation-sensitive composition of the present embodiment in a developing solution at 23° C. is preferably 10 angstrom/sec or more. When the dissolution rate is 10 angstrom/sec or more, the amorphous film more easily dissolves in a developing solution, and is more suitable for a resist. When the amorphous film has a dissolution rate of 10 angstrom/sec or more, the resolution may improve. It is presumed that this is because the micro surface portion of the compound represented by the above formula (1) and/or the resin comprising the compound as a constituent dissolves, and LER is reduced. Also, there are effects of reducing defects.

The dissolution rate can be determined by immersing the amorphous film in a developing solution for a predetermined period of time at 23° C. and then measuring the film thickness before and after immersion by a publicly known method such as visual, ellipsometric, or QCM method.

In the case of a positive type resist pattern, the dissolution rate of the exposed portion after irradiation with radiation such as KrF excimer laser, extreme ultraviolet, electron beam or X-ray, or after heating at 20 to 500° C., of the amorphous film formed by spin coating with the radiation-sensitive composition of the present embodiment, in a developing solution at 23° C. is preferably 10 angstrom/sec or more, more preferably 10 to 10000 angstrom/sec, and still more preferably 100 to 1000 angstrom/sec. When the dissolution rate is 10 angstrom/sec or more, the amorphous film more easily dissolves in a developing solution, and is more suitable for a resist. When the amorphous film has a dissolution rate of 10000 angstrom/sec or less, the resolution may improve. It is presumed that this is because the micro surface portion of the compound represented by the above formula (1) and/or the resin comprising the compound as a constituent dissolves, and LER is reduced. Also, there are effects of reducing defects.

In the case of a negative type resist pattern, the dissolution rate of the exposed portion after irradiation with radiation such as KrF excimer laser, extreme ultraviolet, electron beam or X-ray, or after heating at 20 to 500° C., of the amorphous film formed by spin coating with the radiation-sensitive composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the compound represented by the above formula (1) and/or the resin comprising the compound as a constituent, contrast at the interface between the unexposed portion being dissolved in a developing solution and the exposed portion not being dissolved in a developing solution is increased. Also, there are effects of reducing LER and defects.

[Content Ratio of Each Component]

In the radiation-sensitive composition of the present embodiment, the content of the component (A) is preferably 1 to 99% by mass of the total weight of the solid components (summation of the component (A), the optically active diazonaphthoquinone compound (B), and optionally used solid components such as further component (D), hereinafter the same), more preferably 5 to 95% by mass, still more preferably 10 to 90% by mass, and particularly preferably 25 to 75% by mass. When the content of the component (A) falls within the above range, the radiation-sensitive composition of the present embodiment can produce a pattern with high sensitivity and low roughness.

In the radiation-sensitive composition of the present embodiment, the content of the optically active diazonaphthoquinone compound (B) is preferably 1 to 99% by mass of the total weight of the solid components (summation of the component (A), the optically active diazonaphthoquinone compound (B), and optionally used solid components such as further component (D), hereinafter the same), more preferably 5 to 95% by mass, still more preferably 10 to 90% by mass, and particularly preferably 25 to 75% by mass. When the content of the optically active diazonaphthoquinone compound (B) falls within the above range, the radiation-sensitive composition of the present embodiment can produce a pattern with high sensitivity and low roughness.

As the radiation-sensitive composition of the present embodiment, for example, a radiation-sensitive composition comprising a component (A), an optically active diazonaphthoquinone compound (B), and a solvent, wherein the content of the solvent in the composition is 20 to 99% by mass, and the content of components except for the solvent is 1 to 80% by mass can be used.

[Further Component (D)]

To the radiation-sensitive composition of the present embodiment, if required, as a component other than the component (A) and the optically active diazonaphthoquinone compound (B), one kind or two kinds or more of various additive agents such as the above acid generating agent, acid crosslinking agent, acid diffusion controlling agent, dissolution promoting agent, dissolution controlling agent, sensitizing agent, surfactant, and organic carboxylic acid or oxo acid of phosphor or derivative thereof can be added within the range not inhibiting the objects of the present invention. In the present specification, the further component (D) is also referred to as an optional component (D).

In the radiation-sensitive composition of the present embodiment, the content ratio of each component (the component (A)/the optically active diazonaphthoquinone compound (B)/the optional component (D)) is preferably 1 to 99/99 to 1/0 to 98, more preferably 5 to 95/95 to 5/0 to 49, further preferably 10 to 90/90 to 10/0 to 10, particularly preferably 20 to 80/80 to 20/0 to 5, and most preferably 25 to 75/75 to 25/0% by mass based on the solid components.

The content ratio of each component is selected from each range so that the summation thereof is 100% by mass. When the content ratio of each component falls within the above range, the radiation-sensitive composition of the present embodiment is excellent in performance such as sensitivity and resolution, in addition to roughness.

The radiation-sensitive composition of the present embodiment may contain a resin other than the resin of the present embodiment within the range not inhibiting the objects of the present invention. Examples of such a resin include a novolac resin, polyvinyl phenols, polyacrylic acid, polyvinyl alcohol, a styrene-maleic anhydride resin, and polymers containing an acrylic acid, vinyl alcohol or vinylphenol as a monomeric unit, and derivatives thereof. The content of these resins, which is arbitrarily adjusted according to the kind of the component (A) to be used, is preferably 30 parts by mass or less per 100 parts by mass of the component (A), more preferably 10 parts by mass or less, still more preferably 5 parts by mass or less, and particularly preferably 0 part by mass.

[Resist Pattern Formation Method]

The resist pattern formation method of the present embodiment includes the steps of: forming a resist film on a substrate using the above resist composition of the present embodiment; exposing the formed resist film; and developing the resist film, thereby forming a resist pattern. The resist pattern according to the present embodiment can also be formed as an upper layer resist in a multilayer process.

Examples of the resist pattern formation method include, but not particularly limited to, the following methods. A resist film is formed by coating a conventionally publicly known substrate with the above resist composition of the present embodiment using a coating means such as spin coating, flow casting coating, and roll coating. The conventionally publicly known substrate is not particularly limited. For example, a substrate for electronic components, and the one having a predetermined wiring pattern formed thereon, or the like can be exemplified. More specific examples include a substrate made of a metal such as a silicon wafer, copper, chromium, iron and aluminum, and a glass substrate. Examples of a wiring pattern material include copper, aluminum, nickel, and gold. Also if required, the substrate may be a substrate having an inorganic and/or organic film provided thereon. Examples of the inorganic film include an inorganic antireflection film (inorganic BARC). Examples of the organic film include an organic antireflection film (organic BARC). Surface treatment with hexamethylene disilazane or the like may be conducted.

Next, the coated substrate is heated if required. The heating conditions vary according to the compounding composition of the resist composition, or the like, but are preferably 20 to 250° C., and more preferably 20 to 150° C. By heating, the adhesiveness of a resist to a substrate may improve, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition, or the like. In the present embodiment, in order to stably form a fine pattern with a high degree of accuracy in exposure, the resist film is preferably heated after radiation irradiation. The heating conditions vary according to the compounding composition of the resist composition, or the like, but are preferably 20 to 250° C., and more preferably 20 to 150° C.

Next, by developing the exposed resist film in a developing solution, a predetermined resist pattern is formed. As the developing solution, a solvent having a solubility parameter (SP value) close to that of the compound represented by the formula (1) or the resin comprising the compound represented by the formula (1) as a constituent to be used is preferably selected. A polar solvent such as a ketone-based solvent, an ester-based solvent, an alcohol-based solvent, an amide-based solvent, and an ether-based solvent; and a hydrocarbon-based solvent, or an alkaline aqueous solution can be used.

Examples of the ketone-based solvent include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent include an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include dioxane and tetrahydrofuran in addition to the glycol ether-based solvents.

Examples of the amide-based solvent that can be used include N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include an aromatic hydrocarbon-based solvent such as toluene and xylene; and an aliphatic hydrocarbon-based solvent such as pentane, hexane, octane, and decane.

A plurality of above solvents may be mixed, or the solvent may be used by mixing the solvent with a solvent other than those described above or water within the range having performance. In order to sufficiently exhibit the effect of the present invention, the water content ratio as the whole developing solution is preferably less than 70% by mass and less than 50% by mass, more preferably less than 30% by mass, and further preferably less than 10% by mass. Particularly preferably, the developing solution is substantially moisture free. That is, the content of the organic solvent in the developing solution is not particularly limited, and is preferably 30% by mass or more and 100% by mass or less based on the total amount of the developing solution, preferably 50% by mass or more and 100% by mass or less, more preferably 70% by mass or more and 100% by mass or less, still more preferably 90% by mass or more and 100% by mass or less, and particularly preferably 95% by mass or more and 100% by mass or less.

Examples of the alkaline aqueous solution include an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent improves resist performance such as resolution and roughness of the resist pattern, which is preferable.

The vapor pressure of the developing solution is preferably 5 kPa or less at 20° C., more preferably 3 kPa or less, and particularly preferably 2 kPa or less. The evaporation of the developing solution on the substrate or in a developing cup is inhibited by setting the vapor pressure of the developing solution to 5 kPa or less, to improve temperature uniformity within a wafer surface, thereby resulting in improvement in size uniformity within the wafer surface.

Specific examples having a vapor pressure of 5 kPa or less include a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples having a vapor pressure of 2 kPa or less which is a particularly preferable range include a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required. The surfactant is not particularly limited but, for example, an ionic or nonionic fluorine-based and/or silicon-based surfactant can be used. Examples of the fluorine-based and/or silicon-based surfactant can include the surfactants described in Japanese Patent Application Laid-Open Nos. 62-36663, 61-226746, 61-226745, 62-170950, 63-34540, 7-230165, 8-62834, 9-54432, and 9-5988, and U.S. Pat. Nos. 5,405,720, 5,360, 692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is further preferably used.

The amount of the surfactant used is usually 0.001 to 5% by mass based on the total amount of the developing solution, preferably 0.005 to 2% by mass, and further preferably 0.01 to 0.5% by mass.

The development method is, for example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be practiced.

A step of rinsing the resist film with a rinsing solution containing an organic solvent is preferably provided after the development.

The rinsing solution used in the rinsing step after development is not particularly limited as long as the rinsing solution does not dissolve the resist pattern cured by crosslinking. A solution containing a general organic solvent or water may be used as the rinsing solution. As the rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. More preferably, after development, a step of rinsing the film by using a rinsing solution containing at least one kind of organic solvent selected from the group consisting of a ketone-based solvent, an ester-based solvent, an alcohol-based solvent and an amide-based solvent is conducted. Still more preferably, after development, a step of rinsing the film by using a rinsing solution containing an alcohol-based solvent or an ester-based solvent is conducted. Still more preferably, after development, a step of rinsing the film by using a rinsing solution containing a monohydric alcohol is conducted. Particularly preferably, after development, a step of rinsing the film by using a rinsing solution containing a monohydric alcohol having 5 or more carbon atoms is conducted. The time for rinsing the pattern is not particularly limited, but is preferably 10 seconds to 90 seconds.

Herein, examples of the monohydric alcohol used in the rinsing step after development include a linear, branched or cyclic monohydric alcohol. Specific examples which can be used in the rinsing step include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol or the like. Particularly preferable examples of monohydric alcohol having 5 or more carbon atoms which can be used include 1-hexanol, 2-hexanol, 4-methyl-2-pentanol, 1-pentanol, and 3-methyl-1-butanol or the like.

A plurality of these components may be mixed, or the component may be used by mixing the component with an organic solvent other than those described above.

The water content ratio in the rinsing solution is preferably 10% by mass or less, more preferably 5% by mass or less, and particularly preferably 3% by mass or less. By setting the water content ratio to 10% by mass or less, better development characteristics can be obtained.

The vapor pressure at 20° C. of the rinsing solution used after development is preferably 0.05 kPa or more and 5 kPa or less, more preferably 0.1 kPa or more and 5 kPa or less, and most preferably 0.12 kPa or more and 3 kPa or less. By setting the vapor pressure of the rinsing solution to 0.05 kPa or more and 5 kPa or less, the temperature uniformity in the wafer surface is enhanced and moreover, swelling due to permeation of the rinsing solution is further inhibited. As a result, the dimensional uniformity in the wafer surface is further improved.

The rinsing solution may also be used after adding an appropriate amount of a surfactant to the rinsing solution.

In the rinsing step, the wafer after development is rinsed using the organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate is obtained by etching. Etching can be conducted by a publicly known method such as dry etching using plasma gas, and wet etching with an alkaline solution, a cupric chloride solution, and a ferric chloride solution or the like.

After forming the resist pattern, plating can also be conducted. Examples of the above plating method include copper plating, solder plating, nickel plating, and gold plating.

The remaining resist pattern after etching can be peeled by an organic solvent. Examples of the above organic solvent include PGMEA (propylene glycol monomethyl ether acetate), PGME (propylene glycol monomethyl ether), and EL (ethyl lactate). Examples of the above peeling method include a dipping method and a spraying method. A wiring substrate having a resist pattern formed thereon may be a multilayer wiring substrate, and may have a small diameter through hole.

In the present embodiment, the wiring substrate can also be formed by a method for forming a resist pattern, then depositing a metal in vacuum, and subsequently dissolving the resist pattern in a solution, i.e., a liftoff method.

[Underlayer Film Forming Material for Lithography]

The underlayer film forming material for lithography of the present embodiment contains at least one substance selected from the group consisting of the compound represented by the above formula (1) and the resin comprising the compound as a constituent. The content of the substance in the underlayer film forming material for lithography is preferably 1 to 100% by mass, more preferably 10 to 100% by mass, still more preferably 50 to 100% by mass, particularly preferably 100% by mass, from the viewpoint of coatability and quality stability.

The underlayer film forming material for lithography of the present embodiment is applicable to a wet process and is excellent in heat resistance and etching resistance. Furthermore, the underlayer film forming material for lithography of the present embodiment employs the above substances and can therefore form an underlayer film that is prevented from deteriorating during high temperature baking and is also excellent in etching resistance against oxygen plasma etching or the like. Moreover, the underlayer film forming material for lithography of the present embodiment is also excellent in adhesiveness to a resist layer and can therefore produce an excellent resist pattern. The underlayer film forming material for lithography of the present embodiment may contain an already known underlayer film forming material for lithography or the like, within the range not deteriorating the effect of the present invention.

[Composition for Underlayer Film Formation for Lithography]

The composition for underlayer film formation for lithography of the present embodiment contains the above underlayer film forming material for lithography and a solvent.

[Solvent]

A publicly known solvent can be arbitrarily used as the solvent in the composition for underlayer film formation for lithography of the present embodiment as long as at least the above compound represented by the above formula (1) and/or the resin comprising the compound as a constituent dissolve.

Specific examples of the solvent include, but not particularly limited to: ketone-based solvents such as acetone, methyl ethyl ketone, methyl isobutyl ketone, and cyclohexanone; cellosolve-based solvents such as propylene glycol monomethyl ether and propylene glycol monomethyl ether acetate; ester-based solvents such as ethyl lactate, methyl acetate, ethyl acetate, butyl acetate, isoamyl acetate, methyl methoxypropionate, and methyl hydroxyisobutyrate; alcohol-based solvents such as methanol, ethanol, isopropanol, and 1-ethoxy-2-propanol; and aromatic hydrocarbons such as toluene, xylene, and anisole. These solvents can be used alone as one kind or used in combination of two or more kinds.

Among the above solvents, cyclohexanone, propylene glycol monomethyl ether, propylene glycol monomethyl ether acetate, ethyl lactate, methyl hydroxyisobutyrate, or anisole is particularly preferable from the viewpoint of safety.

The content of the solvent is not particularly limited and is preferably 100 to 10,000 parts by mass per 100 parts by mass of the above underlayer film forming material, more preferably 200 to 5,000 parts by mass, and still more preferably 200 to 1,000 parts by mass, from the viewpoint of solubility and film formation.

[Crosslinking Agent]

The composition for underlayer film formation for lithography of the present embodiment may contain a crosslinking agent, if required, from the viewpoint of, for example, suppressing intermixing. Specific examples of the crosslinking agent that may be used in the present embodiment include, but not particularly limited to, melamine compounds, guanamine compounds, glycoluril compounds, urea compounds, epoxy compounds, thioepoxy compounds, isocyanate compounds, azide compounds, and compounds containing a double bond such as an alkenyl ether group, which have at least one group selected from a methylol group, an alkoxymethyl group, and an acyloxymethyl group as a substituent (crosslinkable group). These crosslinking agents can be used alone as one kind or can be used in combination of two or more kinds. Also, these crosslinking agents may be used as additive agents. The crosslinkable group may be introduced as a pendant group to a polymer side chain in the compound represented by the formula (1) and/or the resin comprising the compound as a constituent. Alternatively, a compound containing a hydroxy group can also be used as the crosslinking agent.

Specific examples of the melamine compounds include hexamethylolmelamine, hexamethoxymethylmelamine, a compound in which 1 to 6 methylol groups of hexamethylolmelamine are methoxymethylated or a mixture thereof, hexamethoxyethylmelamine, hexaacyloxymethylmelamine, and a compound in which 1 to 6 methylol groups of hexamethylolmelamine are acyloxymethylated or a mixture thereof. Specific examples of the epoxy compounds include tris(2,3-epoxypropyl)isocyanurate, trimethylolmethane triglycidyl ether, trimethylolpropane triglycidyl ether, and triethylolethane triglycidyl ether.

Specific examples of the guanamine compounds include tetramethylolguanamine, tetramethoxymethylguanamine, a compound in which 1 to 4 methylol groups of tetramethylolguanamine are methoxymethylated or a mixture thereof, tetramethoxyethylguanamine, tetraacyloxyguanamine, and a compound in which 1 to 4 methylol groups of tetramethylolguanamine are acyloxymethylated or a mixture thereof. Specific examples of the glycoluril compounds include tetramethylolglycoluril, tetramethoxyglycoluril, tetramethoxymethylglycoluril, a compound in which 1 to 4 methylol groups of tetramethylolglycoluril are methoxymethylated or a mixture thereof, and a compound in which 1 to 4 methylol groups of tetramethylolglycoluril are acyloxymethylated or a mixture thereof. Specific examples of the urea compounds include tetramethylolurea, tetramethoxymethylurea, a compound in which 1 to 4 methylol groups of tetramethylolurea are methoxymethylated or a mixture thereof, and tetramethoxyethylurea.

Specific examples of the compounds containing an alkenyl ether group include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

In the composition for underlayer film formation for lithography of the present embodiment, the content of the crosslinking agent is not particularly limited and is preferably 5 to 50 parts by mass per 100 parts by mass of the underlayer film forming material, and more preferably 10 to 40 parts by mass. By the above preferable range, a mixing event with a resist layer tends to be prevented. Also, an antireflection effect is enhanced, and film formability after crosslinking tends to be enhanced.

[Acid Generating Agent]

The composition for underlayer film formation for lithography of the present embodiment may contain an acid generating agent, if required, from the viewpoint of, for example, further accelerating crosslinking reaction by heat. An acid generating agent that generates an acid by thermal decomposition, an acid generating agent that generates an acid by light irradiation, and the like are known, any of which can be used.

Examples of the acid generating agent include, but not particularly limited to,
1) an onium salt of the following general formula (P1a-1), (P1a-2), (P1a-3), or (P1b),
2) a diazomethane derivative of the following general formula (P2),
3) a glyoxime derivative of the following general formula (P3),
4) a bissulfone derivative of the following general formula (P4),
5) a sulfonic acid ester of a N-hydroxyimide compound of the following general formula (P5),
6) a β-ketosulfonic acid derivative,
7) a disulfone derivative,
8) a nitrobenzyl sulfonate derivative, and
9) a sulfonic acid ester derivative.
These acid generating agents can be used alone as one kind or can be used in combination of two or more kinds.

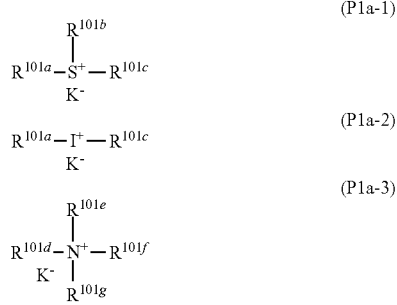

In the above formulas, $R^{101a}$, $R^{101b}$, and $R^{101c}$ each independently represent a linear, branched, or cyclic alkyl group, an alkenyl group, an oxoalkyl group, or an oxoalkenyl group of 1 to 12 carbon atoms; an aryl group of 6 to 20 carbon atoms; or an aralkyl group or an aryloxoalkyl group of 7 to 12 carbon atoms, and one or some or all of hydrogen atoms of each of these groups may be replaced with an alkoxy group or the like. $R^{101b}$ and $R^{101c}$ may form a ring.

In the case of forming a ring, $R^{101b}$ and $R^{101c}$ each independently represent an alkylene group of 1 to 6 carbon atoms. $K^-$ represents a non-nucleophilic counter ion. $R^{101d}$, $R^{101e}$, $R^{101f}$, and $R^{101g}$ each independently represent a hydrogen atom in addition to those represented by $R^{101a}$a, $R^{101b}$, and $R^{101x}$. $R^{101d}$ and $R^{101e}$ or $R^{101d}$, $R^{101e}$, and $R^{101f}$ may form a ring. In the case of forming a ring, $R^{101d}$ and $R^{101e}$ or $R^{101d}$, $R^{101e}$, and $R^{101f}$ each represent an alkylene group of 3 to 10 carbon atoms or represent a heteroaromatic ring having the nitrogen atom in the formula in the ring.

The above $R^{101a}$, $R^{101b}$, $R^{101c}$, $R^{101d}$, $R^{101e}$, $R^{101f}$, and $R^{101g}$ may be the same as or different from each other. Specifically, examples of the alkyl group include, but not limited to, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methylcyclohexyl group, a cyclohexylmethyl group, a norbornyl group, and an adamantyl group. Examples of the alkenyl group include, but not limited to, a vinyl group, an allyl group, a propenyl group, a butenyl group, a hexenyl group, and a cyclohexenyl group. Examples of the oxoalkyl group can include, but not limited to, a 2-oxocyclopentyl group, a 2-oxocyclohexyl group, a 2-oxopropyl group, a 2-cyclopentyl-2-oxoethyl group, a 2-cyclohexyl-2-oxoethyl group, and a 2-(4-methylcyclohexyl)-2-oxoethyl group. Examples of the oxoalkenyl group include, but not limited to, a 2-oxo-4-cyclohexenyl group and a 2-oxo-4-propenyl group. Examples of the aryl group include, but not limited to: a phenyl group; a naphthyl group; alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group; alkylnaphthyl groups such as a methylnaphthyl group and an ethylnaphthyl group; alkoxynaphthyl groups such as a methoxynaphthyl group and an ethoxynaphthyl group; dialkylnaphthyl groups such as a dimethylnaphthyl group and a diethylnaphthyl group; and dialkoxynaphthyl groups such as a dimethoxynaphthyl group and a diethoxynaphthyl group. Examples of the aralkyl group include, but not limited to, a benzyl group, a phenylethyl group, and a phenethyl group. Examples of the aryloxoalkyl group include, but not limited to, 2-aryl-2-oxoethyl groups such as a 2-phenyl-2-oxoethyl group, a 2-(1-naphthyl)-2-oxoethyl group, and a 2-(2-naphthyl)-2-oxoethyl group. Examples of the non-nucleophilic counter ion of $K^-$ include, but not limited to: halide ions such as a chloride ion and a bromide ion; fluoroalkylsulfonates such as triflate, 1,1,1-trifluoroethanesulfonate, and nonafluorobutanesulfonate; arylsulfonates such as tosylate, benzenesulfonate, 4-fluoro benzenesulfonate, and 1,2,3,4,5-pentafluorobenzenesulfonate; and alkylsulfonates such as mesylate and butanesulfonate.

When $R^{101d}$, $R^{101e}$, $R^{101f}$, and $R^{101g}$ are a heteroaromatic ring having the nitrogen atom in the formula in the ring, examples of the heteroaromatic ring include imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

The onium salt of the above formula (P1a-1) or (P1a-2) has functions as a photoacid generating agent and a thermal acid generating agent. The onium salt of the above formula (P1a-3) has functions as a thermal acid generating agent.

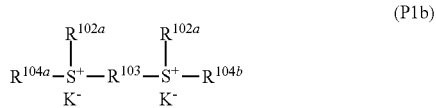

(P1b)

In the formula (P1b), $R^{102a}$ and $R^{102b}$ each independently represent a linear, branched, or cyclic alkyl group of 1 to 8 carbon atoms. $R^{103}$ represents a linear, branched, or cyclic alkylene group of 1 to 10 carbon atoms. $R^{104a}$ and $R^{104b}$ each independently represent a 2-oxoalkyl group of 3 to 7 carbon atoms. $K^-$ represents a non-nucleophilic counter ion.

Specific examples of the $R^{102a}$ and the $R^{102b}$ include, but not limited to, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methylcyclohexyl group, and a cyclohexylmethyl group. Specific examples of $R^{103}$ include, but not limited to, a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. Specific examples of $R^{104a}$ and $R^{104b}$ include, but not limited to, a 2-oxopropyl group, a 2-oxocyclopentyl group, a 2-oxocyclohexyl group, and a 2-oxocycloheptyl group. Examples of $K^-$ can include the same as those described in the formulas (P1a-1), (P1a-2), and (P1a-3).

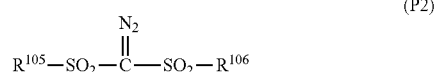

(P2)

In the above formula (P2), $R^{105}$ and $R^{106}$ each independently represent a linear, branched, or cyclic alkyl group or an alkyl halide group of 1 to 12 carbon atoms, an aryl group or an aryl halide group of 6 to 20 carbon atoms, or an aralkyl group of 7 to 12 carbon atoms.

Examples of the alkyl group of $R^{105}$ and $R^{106}$ include, but not limited to, a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group.

Examples of the alkyl halide group include, but not limited to, a trifluoromethyl group, a 1,1,1-trifluoroethyl group, a 1,1,1-trichloroethyl group, and a nonafluorobutyl group.

Examples of the aryl group include, but not limited to: a phenyl group; alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; and alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. Examples of the aryl halide group include, but not limited to, a fluorophenyl group, a chlorophenyl group, and a 1,2,3,4,5-pentafluorophenyl group. Examples of the aralkyl group include, but not limited to, a benzyl group and a phenethyl group.

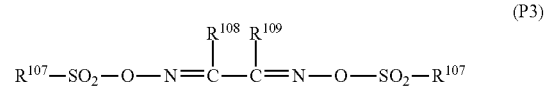

(P3)

In the formula (P3), $R^{107}$, $R^{108}$, and $R^{109}$ each independently represent a linear, branched, or cyclic alkyl group or an alkyl halide group of 1 to 12 carbon atoms; an aryl group or an aryl halide group of 6 to 20 carbon atoms; or an aralkyl group of 7 to 12 carbon atoms. $R^{108}$ and $R^{109}$ may be bonded to each other to form a cyclic structure. In the case of forming a cyclic structure, $R^{108}$ and $R^{109}$ each represent a linear or branched alkylene group of 1 to 6 carbon atoms.

Examples of the alkyl group, the alkyl halide group, the aryl group, the aryl halide group, and the aralkyl group of $R^{107}$, $R^{108}$, and $R^{109}$ include the same groups as those described in $R^{105}$ and $R^{106}$. Examples of the alkylene group of $R^{108}$ and $R^{109}$ include, but not limited to, a methylene group, an ethylene group, a propylene group, a butylene group, and a hexylene group.

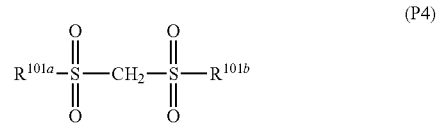

(P4)

In the above formula (P4), $R^{101a}$ and $R^{101b}$ are as defined above.

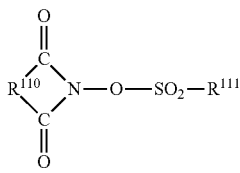
(P5)

In the above formula (P5), $R^{110}$ represents an arylene group of 6 to 10 carbon atoms, an alkylene group of 1 to 6 carbon atoms, or an alkenylene group of 2 to 6 carbon atoms. One or some or all of hydrogen atoms of each of these groups may be further substituted with a linear or branched alkyl group or an alkoxy group of 1 to 4 carbon atoms, a nitro group, an acetyl group, or a phenyl group. $R^{111}$ represents a linear, branched, or substituted alkyl group, an alkenyl group, or an alkoxyalkyl group of 1 to 8 carbon atoms, a phenyl group, or a naphthyl group. One or some or all of hydrogen atoms of each of these groups may be further substituted with an alkyl group or an alkoxy group of 1 to 4 carbon atoms; a phenyl group optionally substituted with an alkyl group of 1 to 4 carbon atoms, an alkoxy group, a nitro group, or an acetyl group; a heteroaromatic group of 3 to 5 carbon atoms; or a chlorine atom or a fluorine atom.

Herein, examples of the arylene group of $R^{110}$ include, but not limited to, a 1,2-phenylene group and a 1,8-naphthylene group. Examples of the alkylene group include, but not limited to, a methylene group, an ethylene group, a trimethylene group, a tetramethylene group, a phenylethylene group, and a norbornane-2,3-diyl group. Examples of the alkenylene group include, but not limited to, a 1,2-vinylene group, a 1-phenyl-1,2-vinylene group, and a 5-norbornene-2,3-diyl group. Examples of the alkyl group of $R^{111}$ include the same as those described as $R^{101a}$ to $R^{101c}$. Examples of the alkenyl group include, but not limited to, a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group. Examples of the alkoxyalkyl group include, but not limited to, a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Examples of the optionally further substituted alkyl group of 1 to 4 carbon atoms include, but not limited to, a methyl group, an ethyl group, a propyl group, an isopropyl group, a n-butyl group, an isobutyl group, and a tert-butyl group. Examples of the alkoxy group of 1 to 4 carbon atoms include, but not limited to, a methoxy group, an ethoxy group, a propoxy group, an isopropoxy group, a n-butoxy group, an isobutoxy group, and a tert-butoxy group. Examples of the phenyl group optionally substituted with an alkyl group of 1 to 4 carbon atoms, an alkoxy group, a nitro group, or an acetyl group include, but not limited to, a phenyl group, a tolyl group, a p-tert-butoxyphenyl group, a p-acetylphenyl group, and a p-nitrophenyl group. Examples of the heteroaromatic group of 3 to 5 carbon atoms include, but not limited to, a pyridyl group and a furyl group.

Specific examples of the acid generating agent include, but not limited to: onium salts such as tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra-n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylenebis[methyl(2-oxocyclopentyl)sulfonium trifluoromethanesulfonate], and 1,2'-naphthylcarbonylmethyltetrahydrothiophenium triflate; diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane; glyoxime derivatives such as bis-(p-toluenesulfonyl)-α-dimethylglyoxime, bis-(p-toluenesulfonyl)-α-diphenylglyoxime, bis-(p-toluenesulfonyl)-α-dicyclohexylglyoxime, bis-(p-toluenesulfonyl)-2,3-pentanedioneglyoxime, bis-(p-toluenesulfonyl)-2-methyl-3,4-pentanedioneglyoxime, bis-(n-butanesulfonyl)-α-dimethylglyoxime, bis-(n-butanesulfonyl)-α-diphenylglyoxime, bis-(n-butanesulfonyl)-α-dicyclohexylglyoxime, bis-(n-butanesulfonyl)-2,3-pentanedioneglyoxime, bis-(n-butanesulfonyl)-2-methyl-3,4-pentanedioneglyoxime, bis-(methanesulfonyl)-α-dimethylglyoxime, bis-(trifluoromethanesulfonyl)-α-dimethylglyoxime, bis-(1,1,1-trifluoroethanesulfonyl)-α-dimethylglyoxime, bis-(tert-butanesulfonyl)-α-dimethylglyoxime, bis-(perfluorooctanesulfonyl)-α- dimethylglyoxime, bis-(cyclohexanesulfonyl)-α-dimethylglyoxime, bis-(benzenesulfonyl)-α-dimethylglyoxime, bis-(p-fluorobenzenesulfonyl)-α-dimethylglyoxime, bis-(p-tert-butylbenzenesulfonyl)-α-dimethylglyoxime, bis-(xylenesulfonyl)-α-dimethylglyoxime, and bis-(camphorsulfonyl)-α-dimethylglyoxime; bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane; β-ketosulfone derivatives such as 2-cyclohexylcarbonyl-2-(p-toluenesulfonyl)propane and 2-isopropylcarbonyl-2-(p-toluenesulfonyl)propane; disulfone derivatives such as diphenyldisulfone derivatives and dicyclohexyldisulfone derivatives; nitrobenzyl sulfonate derivatives such as 2,6-dinitrobenzyl p-toluenesulfonate and 2,4-dinitrobenzyl p-toluenesulfonate; sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid ester derivatives of N-hydroxyimide compounds such as N-hydroxysuccinimide methanesulfonic acid ester, N-hydroxysuccinimide trifluoromethanesulfonic acid ester, N-hydroxysuccinimide ethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide 1-octanesulfonic acid ester, N-hydroxysuccinimide p-toluenesulfonic acid ester, N-hydroxysuccinimide p-methoxybenzenesulfonic acid ester, N-hydroxysuccinimide 2-chloroethanesulfonic acid ester, N-hydroxysuccinimide benzenesulfonic acid ester, N-hydroxysuccinimide-2,4,6-trimethylbenzenesulfonic acid ester, N-hydroxysuccinimide 1-naphthalenesulfonic acid ester, N-hydroxysuccinimide 2-naphthalenesulfonic acid ester, N-hydroxy-2-phenylsuccinimide methanesulfonic acid ester, N-hydroxymaleimide methanesulfonic acid ester, N-hydroxymaleimide ethanesulfonic acid ester, N-hydroxy-2-phenylmaleimide methanesulfonic acid ester, N-hydroxyglutarimide methanesulfonic acid ester, N-hydroxyglutarimide benzenesulfonic acid ester, N-hydroxyphthalimide methanesulfonic acid ester, N-hydroxyphthalimide benzenesulfonic acid ester, N-hydroxyphthalimide trifluoromethanesulfonic acid ester, N-hydroxyphthalimide p-toluenesulfonic acid ester, N-hydroxynaphthalimide methanesulfonic acid ester, N-hydroxynaphthalimide benzenesulfonic acid ester, N-hydroxy-5-norbornene-2,3-dicarboximide methanesulfonic acid ester, N-hydroxy-5-norbornene-2,3-dicarboximide trifluoromethanesulfonic acid ester, and N-hydroxy-5-norbornene-2,3-dicarboximide p-toluenesulfonic acid ester.

Among them, particularly, onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-(p-toluenesulfonyl)-α-dimethylglyoxime and bis-(n-butanesulfonyl)-α-dimethylglyoxime; bissulfone derivatives such as bisnaphthylsulfonylmethane; and sulfonic acid ester derivatives of N-hydroxyimide compounds such as N-hydroxysuccinimide methanesulfonic acid ester, N-hydroxysuccinimide trifluoromethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide p-toluenesulfonic acid ester, N-hydroxynaphthalimide methanesulfonic acid ester, and N-hydroxynaphthalimide benzenesulfonic acid ester are preferably used.

In the composition for underlayer film formation for lithography of the present embodiment, the content of the acid generating agent is not particularly limited and is preferably 0.1 to 50 parts by mass per 100 parts by mass of the underlayer film forming material, and more preferably 0.5 to 40 parts by mass. By the above preferable range, crosslinking reaction tends to be enhanced by an increased amount of an acid generated. Also, a mixing event with a resist layer tends to be prevented.

[Basic Compound]

The composition for underlayer film formation for lithography of the present embodiment may further contain a basic compound from the viewpoint of, for example, improving storage stability.

The basic compound plays a role as a quencher against acids in order to prevent crosslinking reaction from proceeding due to a trace amount of an acid generated by the acid generating agent. Examples of such a basic compound include, but not particularly limited to, primary, secondary or tertiary aliphatic amines, amine blends, aromatic amines, heterocyclic amines, nitrogen-containing compounds having a carboxy group, nitrogen-containing compounds having a sulfonyl group, nitrogen-containing compounds having a hydroxy group, nitrogen-containing compounds having a hydroxyphenyl group, alcoholic nitrogen-containing compounds, amide derivatives, and imide derivatives.

Specifically, specific examples of the primary aliphatic amines include, but not limited to, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amines include, but not limited to, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Specific examples of the tertiary aliphatic amines include, but not limited to, trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the amine blends include, but not limited to, dimethylethylamine, methylethylpropylamine, benzylamine, phenethylamine, and benzyldimethylamine. Specific examples of the aromatic amines and the heterocyclic amines include, but not limited to, aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isoxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Specific examples of the nitrogen-containing compounds having a carboxy group include, but not limited to, aminobenzoic acid, indolecarboxylic acid, and amino acid derivatives (e.g., nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Specific examples of the nitrogen-containing compounds having a sulfonyl group include, but not limited to, 3-pyridinesulfonic acid and pyridinium p-toluenesulfonate. Specific examples of the nitrogen-containing compounds having a hydroxy group, the nitrogen-containing compounds having a hydroxyphenyl group, and the alcoholic nitrogen-containing compounds include, but not limited to, 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidineethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidineethanol, 1-aziridineethanol, N-(2-hydroxyethyl)phthalimide, and N-(2-hydroxyethyl)isonicotinamide. Specific examples of the amide derivatives include, but not limited to, formamide, N-methylformamide, N,N-dimethylformamide, acetamide, N-methylacetamide, N,N-dimethylacetamide, propionamide, and benzamide. Specific examples of the imide derivatives include, but not limited to, phthalimide, succinimide, and maleimide.

In the composition for underlayer film formation for lithography of the present embodiment, the content of the basic compound is not particularly limited and is preferably 0.001 to 2 parts by mass per 100 parts by mass of the underlayer film forming material, and more preferably 0.01 to 1 parts by mass. By the above preferable range, storage stability tends to be enhanced without excessively deteriorating crosslinking reaction.

[Further Additive Agent]

The composition for underlayer film formation for lithography of the present embodiment may also contain an additional resin and/or compound for the purpose of conferring thermosetting properties or controlling absorbance. Examples of such an additional resin and/or compound include, but not particularly limited to, naphthol resin, xylene resin naphthol-modified resin, phenol-modified resin of naphthalene resin, polyhydroxystyrene, dicyclopentadiene resin, resins containing (meth)acrylate, dimethacrylate, trimethacrylate, tetramethacrylate, a naphthalene ring such as vinylnaphthalene or polyacenaphthylene, a biphenyl ring such as phenanthrenequinone or fluorene, or a heterocyclic ring having a heteroatom such as thiophene or indene, and resins containing no aromatic ring; and resins or compounds containing an alicyclic structure, such as rosin-based resin, cyclodextrin, adamantine(poly)ol, tricyclodecane(poly)ol, and derivatives thereof. The composition for underlayer film formation for lithography of the present embodiment may further contain a publicly known additive agent. Examples of the above publicly known additive agent include, but not limited to, ultraviolet absorbers, surfactants, colorants, and nonionic surfactants.

[Underlayer Film for Lithography and Multilayer Resist Pattern Formation Method]

The underlayer film for lithography of the present embodiment is formed from the composition for underlayer film formation for lithography of the present embodiment. The method for producing the underlayer film for lithography of the present embodiment comprises the step of forming an underlayer film on a substrate using the above composition for underlayer film formation for lithography.

The pattern formation method (resist pattern formation method) of the present embodiment has the steps of: forming a underlayer film on a substrate using the composition for underlayer film formation for lithography of the present embodiment (step (A-1)); forming at least one photoresist layer on the underlayer film (step (A-2)); and irradiating a predetermined region of the photoresist layer with radiation for development after the second formation step (step (A-3)).

Another pattern formation method (circuit pattern formation method) of the present embodiment has the steps of: forming an underlayer film on a substrate using the composition for underlayer film formation for lithography of the present embodiment (step (B-1)); forming an intermediate layer film on the underlayer film using a resist intermediate layer film material containing a silicon atom (step (B-2));

forming at least one photoresist layer on the intermediate layer film (step (B-3)); after the step (B-3), irradiating a predetermined region of the photoresist layer with radiation for development, thereby forming a resist pattern (step (B-4)); and after the step (B-4), etching the intermediate layer film with the resist pattern as a mask, etching the underlayer film with the obtained intermediate layer film pattern as an etching mask, and etching the substrate with the obtained underlayer film pattern as an etching mask, thereby forming a pattern on the substrate (step (B-5)).

The underlayer film for lithography of the present embodiment is not particularly limited by its formation method as long as it is formed from the composition for underlayer film formation for lithography of the present embodiment. A publicly known approach can be applied thereto. The underlayer film can be formed by, for example, applying the composition for underlayer film formation for lithography of the present embodiment onto a substrate by a publicly known coating method or printing method such as spin coating or screen printing, and then removing an organic solvent by volatilization or the like.

It is preferable to perform baking in the formation of the underlayer film, for preventing a mixing event with an upper layer resist while accelerating crosslinking reaction. In this case, the baking temperature is not particularly limited and is preferably in the range of 80 to 450° C., and more preferably 200 to 400° C. The baking time is not particularly limited and is preferably in the range of 10 to 300 seconds. The thickness of the underlayer film can be arbitrarily selected according to required performance and is not particularly limited, but usually preferably about 30 to 20,000 nm, and more preferably 50 to 15,000 nm.

After preparing the underlayer film, it is preferable to prepare a silicon-containing resist layer or a usual single-layer resist made of hydrocarbon thereon in the case of a two-layer process, and to prepare a silicon-containing intermediate layer thereon and further a silicon-free single-layer resist layer thereon in the case of a three-layer process. In this case, a publicly known photoresist material can be used for forming this resist layer.

After preparing the underlayer film on the substrate, in the case of a two-layer process, a silicon-containing resist layer or a usual single-layer resist made of hydrocarbon can be prepared on the underlayer film. In the case of a three-layer process, a silicon-containing intermediate layer can be prepared on the underlayer film, and a silicon-free single-layer resist layer can be further prepared on the silicon-containing intermediate layer. In these cases, a publicly known photoresist material can be arbitrarily selected and used for forming the resist layer, without particular limitations.

For the silicon-containing resist material for a two-layer process, a silicon atom-containing polymer such as a polysilsesquioxane derivative or a vinylsilane derivative is used as a base polymer, and a positive type photoresist material further containing an organic solvent, an acid generating agent, and if required, a basic compound or the like is preferably used, from the viewpoint of oxygen gas etching resistance. Herein, a publicly known polymer that is used in this kind of resist material can be used as the silicon atom-containing polymer.

A polysilsesquioxane-based intermediate layer is preferably used as the silicon-containing intermediate layer for a three-layer process. By imparting effects as an antireflection film to the intermediate layer, there is a tendency that reflection can be effectively suppressed. For example, use of a material containing a large amount of an aromatic group and having high substrate etching resistance as the underlayer film in a process for exposure at 193 nm tends to increase a k value and enhance substrate reflection. However, the intermediate layer suppresses the reflection so that the substrate reflection can be 0.5% or less. The intermediate layer having such an antireflection effect is not limited, and polysilsesquioxane that crosslinks by an acid or heat in which a light absorbing group having a phenyl group or a silicon-silicon bond is introduced is preferably used for exposure at 193 nm.

Alternatively, an intermediate layer formed by chemical vapour deposition (CVD) may be used. The intermediate layer highly effective as an antireflection film prepared by CVD is not limited, and, for example, a SiON film is known. In general, the formation of an intermediate layer by a wet process such as spin coating or screen printing is more convenient and more advantageous in cost, as compared with CVD. The upper layer resist for a three-layer process may be positive type or negative type, and the same as a single-layer resist generally used can be used.

The underlayer film according to the present embodiment can also be used as an antireflection film for usual single-layer resists or an underlying material for suppression of pattern collapse. The underlayer film of the present embodiment is excellent in etching resistance for an underlying process and can be expected to also function as a hard mask for an underlying process.

In the case of forming a resist layer from the above photoresist material, a wet process such as spin coating or screen printing is preferably used, as in the case of forming the above underlayer film. After coating with the resist material by spin coating or the like, prebaking is generally performed. This prebaking is preferably performed at 80 to 180° C. in the range of 10 to 300 seconds. Then, exposure, post-exposure baking (PEB), and development can be performed according to a conventional method to obtain a resist pattern. The thickness of the resist film is not particularly limited and is generally preferably 30 to 500 nm, and more preferably 50 to 400 nm.

The exposure light can be arbitrarily selected and used according to the photoresist material to be used. General examples thereof can include a high energy ray having a wavelength of 300 nm or less, specifically, excimer laser of 248 nm, 193 nm, or 157 nm, soft x-ray of 3 to 20 nm, electron beam, and X-ray.

In a resist pattern formed by the above method, pattern collapse is suppressed by the underlayer film according to the present embodiment. Therefore, use of the underlayer film according to the present embodiment can produce a finer pattern and can reduce an exposure amount necessary for obtaining the resist pattern.

Next, etching is performed with the obtained resist pattern as a mask. Gas etching is preferably used as the etching of the underlayer film in a two-layer process. The gas etching is preferably etching using oxygen gas. In addition to oxygen gas, an inert gas such as He or Ar, or CO, $CO_2$, $NH_3$, $SO_2$, $N_2$, $NO_2$, or $H_2$ gas may be added. Alternatively, the gas etching may be performed with CO, $CO_2$, $NH_3$, $N_2$, $NO_2$, or $H_2$ gas without the use of oxygen gas. Particularly, the latter gas is preferably used for side wall protection in order to prevent the undercut of pattern side walls.

On the other hand, gas etching is also preferably used as the etching of the intermediate layer in a three-layer process. The same gas etching as described in the above two-layer process is applicable. Particularly, it is preferable to process the intermediate layer in a three-layer process by using chlorofluorocarbon-based gas and using the resist pattern as a mask. Then, as mentioned above, for example, the underlayer film can be processed by oxygen gas etching with the intermediate layer pattern as a mask.

Herein, in the case of forming an inorganic hard mask intermediate layer film as the intermediate layer, a silicon oxide film, a silicon nitride film, or a silicon oxynitride film (SiON film) is formed by CVD, ALD, or the like. A method for forming the nitride film is not limited, and, for example, a method described in Japanese Patent Laid-Open No. 2002-334869 (Patent Literature 6) or WO2004/066377 (Patent Literature 7) can be used. Although a photoresist film can be formed directly on such an intermediate layer film, an organic antireflection film (BARC) may be formed on the intermediate layer film by spin coating and a photoresist film may be formed thereon.

A polysilsesquioxane-based intermediate layer is preferably used as the intermediate layer. By imparting effects as an antireflection film to the resist intermediate layer film, there is a tendency that reflection can be effectively suppressed. A specific material for the polysilsesquioxane-based intermediate layer is not limited, and, for example, a material described in Japanese Patent Laid-Open No. 2007-226170 (Patent Literature 8) or Japanese Patent Laid-Open No. 2007-226204 (Patent Literature 9) can be used.

The subsequent etching of the substrate can also be performed by a conventional method. For example, the substrate made of $SiO_2$ or SiN can be etched mainly using chlorofluorocarbon-based gas, and the substrate made of p-Si, Al, or W can be etched mainly using chlorine- or bromine-based gas. In the case of etching the substrate with chlorofluorocarbon-based gas, the silicon-containing resist of the two-layer resist process or the silicon-containing intermediate layer of the three-layer process is peeled at the same time with substrate processing. On the other hand, in the case of etching the substrate with chlorine- or bromine-based gas, the silicon-containing resist layer or the silicon-containing intermediate layer is separately peeled and in general, peeled by dry etching using chlorofluorocarbon-based gas after substrate processing.

A feature of the underlayer film according to the present embodiment is that it is excellent in etching resistance of these substrates. The substrate can be arbitrarily selected from publicly known ones and used and is not particularly limited. Examples thereof include Si, α-Si, p-Si, $SiO_2$, SiN, SiON, W, TiN, and Al. The substrate may be a laminate having a film to be processed (substrate to be processed) on a base material (support). Examples of such a film to be processed include various low-k films such as Si, $SiO_2$, SiON, SiN, p-Si, α-Si, W, W—Si, Al, Cu, and Al—Si, and stopper films thereof. A material different from that for the base material (support) is generally used. The thickness of the substrate to be processed or the film to be processed is not particularly limited and is generally preferably about 50 to 10,000 nm, and more preferably 75 to 5,000 nm.

[Method for Purifying Compound and/or Resin]

The method for purifying the compound and/or the resin of the present embodiment comprises the steps of: obtaining a solution (S) by dissolving one or more kinds selected from the compound represented by the formula (1) and the resin comprising the compound as a constituent in a solvent; and extracting impurities in the compound and/or the resin by bringing the obtained solution (S) into contact with an acidic aqueous solution (a first extraction step), wherein the solvent used in the step of obtaining the solution (S) contains an organic solvent that does not inadvertently mix with water.

In the first extraction step, the resin is preferably a resin obtained by a reaction between the compound represented by the above formula (1) and a crosslinking compound.

According to the purification method of the present embodiment, the contents of various metals that may be contained as impurities in the compound or the resin having a specific structure described above can be reduced.

More specifically, in the purification method of the present embodiment, the compound and/or the resin is dissolved in an organic solvent that does not inadvertently mix with water to obtain the solution (S), and further, extraction treatment can be carried out by bringing the solution (S) into contact with an acidic aqueous solution. Thereby, metals contained in the solution (S) containing the compound represented by the above formula (1) and/or the resin comprising the compound as a constituent are transferred to the aqueous phase, then the organic phase and the aqueous phase are separated, and thus the compound represented by the above formula (1) and/or the resin comprising the compound as a constituent having a reduced metal content can be obtained.

The compound represented by the above formula (1) and/or the resin comprising the compound as a constituent used in the purification method of the present embodiment may be alone, or may be a mixture of two or more kinds. Also, the compound represented by the above formula (1) and/or the resin comprising the compound as a constituent may contain various surfactants, various crosslinking agents, various acid generating agents, various stabilizers, and the like.

The solvent that does not inadvertently mix with water used in the present embodiment is not particularly limited, but is preferably an organic solvent that is safely applicable to semiconductor manufacturing processes, and specifically it is an organic solvent having a solubility in water at room temperature of less than 30%, and more preferably is an organic solvent having a solubility of less than 20% and particularly preferably less than 10%. The amount of the organic solvent used is preferably 1 to 100 times the mass of the compound represented by the above formula (1) and/or the resin comprising the compound as a constituent to be used.

Specific examples of the solvent that does not inadvertently mix with water include, but not limited to, ethers such as diethyl ether and diisopropyl ether; esters such as ethyl acetate, n-butyl acetate, and isoamyl acetate; ketones such as methyl ethyl ketone, methyl isobutyl ketone, ethyl isobutyl ketone, cyclohexanone, cyclopentanone, 2-heptanone, and 2-pentanone; glycol ether acetates such as ethylene glycol monoethyl ether acetate, ethylene glycol monobutyl ether acetate, propylene glycol monomethyl ether acetate (PGMEA), and propylene glycol monoethyl ether acetate; aliphatic hydrocarbons such as n-hexane and n-heptane; aromatic hydrocarbons such as toluene and xylene; and halogenated hydrocarbons such as methylene chloride and chloroform. Among these, toluene, 2-heptanone, cyclohexanone, cyclopentanone, methyl isobutyl ketone, propylene glycol monomethyl ether acetate, ethyl acetate, and the like are preferable, methyl isobutyl ketone, ethyl acetate, cyclohexanone, and propylene glycol monomethyl ether acetate are more preferable, and methyl isobutyl ketone and ethyl acetate are still more preferable. Methyl isobutyl ketone, ethyl acetate, and the like have relatively high saturation solubility for the compound represented by the above formula (1) and the resin comprising the compound as a constituent and a relatively low boiling point, and it is thus possible to reduce the load in the case of industrially distilling off the solvent and in the step of removing the solvent by drying. These solvents can be each used alone, and can be used as a mixture of two or more kinds.

The acidic aqueous solution used in the purification method of the present embodiment is arbitrarily selected from among aqueous solutions in which organic compounds or inorganic compounds are dissolved in water, generally known as acidic aqueous solutions. Examples thereof include, but not limited to, aqueous mineral acid solutions in mineral acids such as hydrochloric acid, sulfuric acid, nitric acid, and phosphoric acid are dissolved in water, or aqueous organic acid solutions in organic acids such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are dissolved in water. These acidic aqueous solutions can be each used alone, and can be also used as a combination of two or more kinds. Among these acidic aqueous solutions, aqueous solutions of one or more mineral acids selected from the group consisting of hydrochloric acid, sulfuric acid, nitric acid, and phosphoric acid, or aqueous solutions of one or more organic acids selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are preferable, aqueous solutions of sulfuric acid, nitric acid, and carboxylic acids such as acetic acid, oxalic acid, tartaric acid, and citric acid are more preferable, aqueous solutions of sulfuric acid, oxalic acid, tartaric acid, and citric acid are still more preferable, and an aqueous solution of oxalic acid is further preferable. It is considered that polyvalent carboxylic acids such as oxalic acid, tartaric acid, and citric acid coordinate with metal ions and provide a chelating effect, and thus tend to be capable of more effectively removing metals. As for water used herein, it is preferable to use water, the metal content of which is small, such as ion exchanged water, according to the purpose of the purification method of the present embodiment.

The pH of the acidic aqueous solution used in the purification method of the present embodiment is not particularly limited, but it is preferable to regulate the acidity of the aqueous solution in consideration of an influence on the compound represented by the above formula (1) and/or the resin comprising the compound as a constituent. Normally, the pH range is about 0 to 5, and is preferably about pH 0 to 3.

The amount of the acidic aqueous solution used in the purification method of the present embodiment is not particularly limited, but it is preferable to regulate the amount from the viewpoint of reducing the number of extraction operations for removing metals and from the viewpoint of ensuring operability in consideration of the overall amount of fluid. From the above viewpoints, the amount of the acidic aqueous solution used is preferably 10 to 200% by mass, more preferably 20 to 100% by mass, based on 100% by mass of the solution (S).

In the purification method of the present embodiment, by bringing an acidic aqueous solution as described above into contact with the solution (S) containing the one or more kinds selected from the compound represented by the above formula (1) and the resin comprising the compound as a constituent and the solvent that does not inadvertently mix with water, metals can be extracted from the compound or the resin in the solution (S).

In the purification method of the present embodiment, it is preferable that the solution (S) further contains an organic solvent that inadvertently mixes with water. When an organic solvent that inadvertently mixes with water is contained, there is a tendency that the amount of the compound represented by the above formula (1) and/or the resin comprising the compound as a constituent charged can be increased, also the fluid separability is improved, and purification can be carried out at a high reaction vessel efficiency. The method for adding the organic solvent that inadvertently mixes with water is not particularly limited. For example, any of a method involving adding it to the organic solvent-containing solution in advance, a method involving adding it to water or the acidic aqueous solution in advance, and a method involving adding it after bringing the organic solvent-containing solution into contact with water or the acidic aqueous solution. Among these, the method involving adding it to the organic solvent-containing solution in advance is preferable in terms of the workability of operations and the ease of managing the amount.

The organic solvent that inadvertently mixes with water used in the purification method of the present embodiment is not particularly limited, but is preferably an organic solvent that is safely applicable to semiconductor manufacturing processes. The amount of the organic solvent used that inadvertently mixes with water is not particularly limited as long as the solution phase and the aqueous phase separate, but is preferably 0.1 to 100 times, more preferably 0.1 to 50 times, and further preferably 0.1 to 20 times the mass of the compound represented by the above formula (1) and/or the resin comprising the compound as a constituent.

Specific examples of the organic solvent used in the purification method of the present embodiment that inadvertently mixes with water include, but not limited to, ethers such as tetrahydrofuran and 1,3-dioxolane; alcohols such as methanol, ethanol, and isopropanol; ketones such as acetone and N-methylpyrrolidone; aliphatic hydrocarbons such as glycol ethers such as ethylene glycol monoethyl ether, ethylene glycol monobutyl ether, propylene glycol monomethyl ether (PGME), and propylene glycol monoethyl ether. Among these, N-methylpyrrolidone, propylene glycol monomethyl ether, and the like are preferable, and N-methylpyrrolidone and propylene glycol monomethyl ether are more preferable. These solvents can be each used alone, and can be used as a mixture of two or more kinds.

The temperature when extraction treatment is carried out is generally in the range of 20 to 90° C., and preferably 30 to 80° C. The extraction operation is carried out, for example, by thoroughly mixing the solution (S) and the acidic aqueous solution by stirring or the like and then leaving the obtained mixed solution to stand still. Thereby, metals contained in the solution containing the compound represented by the above formula (1) and/or the resin comprising the compound as a constituent and the organic solvents are transferred to the aqueous phase. Also, by this operation, the acidity of the solution is lowered, and the degradation of the compound represented by the formula (1) and/or the resin obtained with the compound as a monomer can be suppressed.

By being left to stand still, the mixed solution is separated into an aqueous phase and a solution phase containing the one or more kinds selected from the compound represented by the above formula (1) and the resin comprising the compound as a constituent and the solvents, and thus the solution phase containing the one or more kinds selected from the compound represented by the above formula (1) and the resin comprising the compound as a constituent and the solvents is recovered by decantation. The time for leaving the mixed solution to stand still is not particularly limited, but it is preferable to regulate the time for leaving the mixed solution to stand still from the viewpoint of attaining good separation of the solution phase containing the solvents and the aqueous phase. Normally, the time for leaving the mixed solution to stand still is 1 minute or longer, preferably 10 minutes or longer, and more preferably 30 minutes or longer. While the extraction treatment may be carried out once, it is effective to repeat mixing, leaving-to-stand-still, and separating operations multiple times.

It is preferable that the purification method of the present embodiment includes the step of extracting impurities in the compound or the resin by further bringing the solution phase containing the compound or the resin into contact with water after the first extraction step (the second extraction step). Specifically, for example, it is preferable that after the above extraction treatment is carried out using an acidic aqueous solution, the solution phase that is extracted and recovered from the aqueous solution and that contains the one or more kinds selected from the compound represented by the above formula (1) and the resin comprising the compound as a constituent and the solvents is further subjected to extraction treatment with water. The above extraction treatment with water is not particularly limited, and can be carried out, for example, by thoroughly mixing the solution phase and water by stirring or the like and then leaving the obtained mixed solution to stand still. The mixed solution after being left to stand still is separated into an aqueous phase and a solution phase containing the one or more kinds selected from the compound represented by the above formula (1) and the resin comprising the compound as a constituent and the solvents, and thus the solution phase containing the one or more kinds selected from the compound represented by the above formula (1) and the resin comprising the compound as a constituent and the solvents can be recovered by decantation.

Water used herein is preferably water, the metal content of which is small, such as ion exchanged water, according to the purpose of the present embodiment. While the extraction treatment may be carried out once, it is effective to repeat mixing, leaving-to-stand-still, and separating operations multiple times. The proportions of both used in the extraction treatment and temperature, time, and other conditions are not particularly limited, and may be the same as those of the previous contact treatment with the acidic aqueous solution.

Water that is possibly present in the thus-obtained solution containing the one or more kinds selected from the compound represented by the above formula (1) and the resin comprising the compound as a constituent and the solvents can be easily removed by performing vacuum distillation or a like operation. Also, if required, the concentration of the compound represented by the above formula (1) and/or the resin comprising the compound as a constituent can be regulated to be any concentration by adding a solvent to the solution.

The method for isolating the compound represented by the above formula (1) and/or the resin comprising the compound as a constituent from the obtained solution containing the compound represented by the above formula (1) and/or the resin comprising the compound as a constituent and the solvents is not particularly limited, and publicly known methods can be carried out, such as reduced-pressure removal, separation by reprecipitation, and a combination thereof. Publicly known treatments such as concentration operation, filtration operation, centrifugation operation, and drying operation can be carried out if required.

EXAMPLES

The present embodiment will be more specifically described with reference to examples below. However, the present embodiment is not particularly limited to these examples.

(Structure of Compound)

The structure of a compound was confirmed by $^1$H-NMR measurement using Advance600II spectrometer manufactured by Bruker Corp. under the following conditions:

Frequency: 400 MHz
Solvent: d6-DMSO
Internal standard: TMS
Measurement temperature: 23° C.

(Carbon Concentration and Oxygen Concentration)

The carbon concentration and the oxygen concentration (% by mass) were measured by organic elemental analysis.

Apparatus: CHN Coder MT-6 (manufactured by Yaic. Yanaco)

(Molecular Weight)

The molecular weight of a compound was measured by FD-MS analysis using JMS-T100GCV manufactured by JEOL Ltd.

Alternatively, the weight average molecular weight (Mw) and the number average molecular weight (Mn) in terms of polystyrene were determined by gel permeation chromatography (GPC) analysis, and dispersibility (Mw/Mn) was determined.

Apparatus: Shodex GPC-101 model (manufactured by Showa Denko K.K.)
Column: KF-80M×3
Eluent: 1 ml/min THF
Temperature: 40° C.

(Thermal Decomposition Temperature (Tg))

EXSTAR 6000 DSC apparatus manufactured by SII NanoTechnology Inc. was used. About 5 mg of a sample was placed in an unsealed container made of aluminum, and the temperature was raised to 500° C. at a temperature increase rate of 10° C./min in a nitrogen gas stream (30 ml/min) The temperature at which a decrease in baseline appeared was defined as the thermal decomposition temperature (Tg). The heat resistance was evaluated according to the following criteria.

—Criteria—

Evaluation A: The thermal decomposition temperature was ≥150° C.

Evaluation C: The thermal decomposition temperature was <150° C.

(Solubility)

A compound was dissolved at 5% by mass in 1-methoxy-2-propanol (PGME) at 23° C. Then, the solution was left at 5° C. for 30 days. The results were evaluated according to the following criteria.

—Criteria—

Evaluation A: No precipitate was visually confirmed.
Evaluation C: Precipitates were visually confirmed.

[Synthesis Example 1] Synthesis of BisF-1

A container (internal capacity: 200 mL) equipped with a stirrer, a condenser tube, and a burette was prepared. To this container, 30 g (161 mmol) of 4,4-biphenol (a reagent manufactured by Tokyo Kasei Kogyo Co., Ltd.), 15 g (82 mmol) of 4-biphenylaldehyde (manufactured by Mitsubishi Gas Chemical Company Inc.), and 100 mL of butyl acetate were added, and 3.9 g (21 mmol) of p-toluenesulfonic acid (a reagent manufactured by Kanto Chemical Co., Inc.) was added to prepare a reaction solution. The reaction solution was stirred at 90° C. for 3 hours and reacted. Next, the reaction solution was concentrated. The reaction product was precipitated by the addition of 50 g of heptane. After cooling to room temperature, the precipitates were separated by filtration. The solid matter obtained by filtration was dried and then separated and purified by column chromatography to obtain 5.8 g of the objective compound (BisF-1) represented by the following formula.

As a result of measuring the molecular weight of the obtained compound by the above method, it was 536.

The following peaks were found by NMR measurement performed on the obtained compound under the above measurement conditions, and the compound was confirmed to have a chemical structure of the following formula.

δ (ppm) 9.4 (4H, O—H), 6.8-7.8 (23H, Ph-H), 6.2 (1H, C—H)

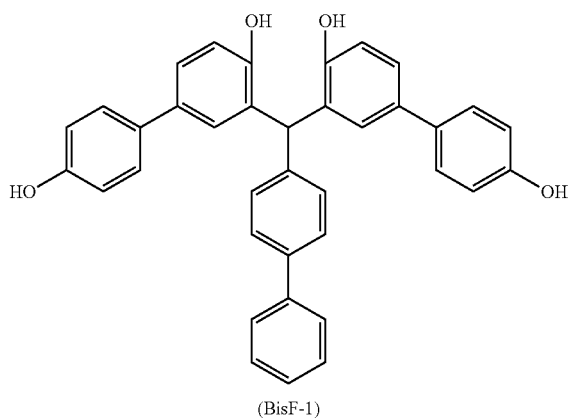 [SMILES: Oc1ccc(-c2ccc(O)c(C(c3ccc(-c4ccccc4)cc3)c3cc(-c4ccc(O)cc4)ccc3O)c2)cc1]

(BisF-1)

[Synthesis Working Example 1] Synthesis of BisF-1-BOC

To a container (internal capacity: 200 mL) equipped with a stirrer, a condenser tube, and a burette, 6.7 g (12.5 mmol) of the obtained compound (BisF-1) and 11.0 g (50 mmol) of di-t-butyl dicarbonate (manufactured by Sigma-Aldrich) were added with 100 mL of acetone, then 6.9 g (50 mmol) of potassium carbonate (manufactured by Sigma-Aldrich) was added, and the contents were reacted by being stirred at 20° C. for 6 hours to obtain a reaction solution. Next, the reaction solution was concentrated. The reaction product was precipitated by the addition of 100 g of pure water to the concentrate. After cooling to room temperature, the solid matter was separated by filtration.

The obtained solid matter was subjected to filtration, dried, and then separated and purified by column chromatography to obtain 2 g of the objective compound (BisF-1-BOC) represented by the following formula (BisF-1-BOC).

As a result of measuring the molecular weight of the obtained compound (BisF-1-BOC) by the above method, it was 937. The carbon concentration was 73.1%, and the oxygen concentration was 20.4%.

The following peaks were found by NMR measurement performed on the obtained compound (BisF-1-BOC) under the above measurement conditions, and the compound was confirmed to have a chemical structure of the following formula (BisF-1-BOC).

δ (ppm) 6.8-7.8 (23H, Ph-H), 6.2 (1H, C—H), 1.6 (36H, C—CH₃)

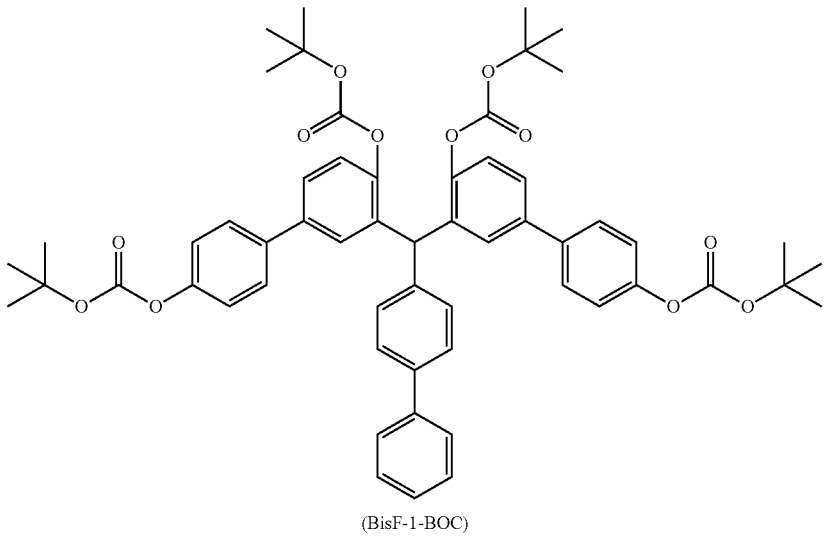 [SMILES: CC(C)(C)OC(=O)Oc1ccc(-c2ccc(OC(=O)OC(C)(C)C)c(C(c3ccc(-c4ccccc4)cc3)c3cc(-c4ccc(OC(=O)OC(C)(C)C)cc4)ccc3OC(=O)OC(C)(C)C)c2)cc1]

(BisF-1-BOC)

[Synthesis Example 2] Synthesis of BisF-I-1

A container (internal capacity: 200 mL) equipped with a stirrer, a condenser tube, and a burette was prepared. To this container, 30 g (161 mmol) of 4,4-biphenol (a reagent manufactured by Tokyo Kasei Kogyo Co., Ltd.), 15 g (65 mmol) of 4-iodobenzaldehyde (a reagent manufactured by Tokyo Kasei Kogyo Co., Ltd.), and 100 mL of 4-butyrolactone were added, and 3.9 g (21 mmol) of p-toluenesulfonic acid (a reagent manufactured by Kanto Chemical Co., Inc.) was added to prepare a reaction solution. The reaction solution was stirred at 90° C. for 3 hours and reacted. Next, the reaction solution was concentrated. The reaction product was precipitated by the addition of 50 g of heptane. After cooling to room temperature, the precipitates were separated by filtration. The solid matter obtained by filtration was dried and then separated and purified by column chromatography to obtain 4.2 g of the objective compound (BisF-I-1) represented by the following formula.

As a result of measuring the molecular weight of the obtained compound by the above method, it was 586.

The following peaks were found by NMR measurement performed on the obtained compound under the above measurement conditions, and the compound was confirmed to have a chemical structure of the following formula.

δ (ppm) 9.4 (4H, O—H), 6.8-7.8 (18H, Ph-H), 6.2 (1H, C—H)

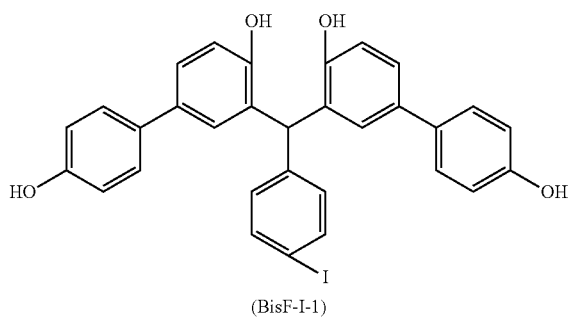 [SMILES: Oc1ccc(-c2ccc(O)c(C(c3ccc(I)cc3)c3cc(-c4ccc(O)cc4)ccc3O)c2)cc1]

(BisF-I-1)

[Synthesis Working Example 2] Synthesis of BisF-I-1-BOC

To a container (internal capacity: 200 mL) equipped with a stirrer, a condenser tube, and a burette, 7.3 g (12.5 mmol) of the obtained compound (BisF-I-1) and 11.0 g (50 mmol) of di-t-butyl dicarbonate (manufactured by Sigma-Aldrich) were added with 100 mL of acetone, then 6.9 g (50 mmol) of potassium carbonate (manufactured by Sigma-Aldrich) was added, and the contents were reacted by being stirred at 20° C. for 6 hours to obtain a reaction solution. Next, the reaction solution was concentrated. The reaction product was precipitated by the addition of 100 g of pure water to the concentrate. After cooling to room temperature, the solid matter was separated by filtration.

The obtained solid matter was subjected to filtration, dried, and then separated and purified by column chromatography to obtain 2 g of the objective compound (BisF-I-1-BOC) represented by the following formula (BisF-I-1-BOC).

As a result of measuring the molecular weight of the obtained compound (BisF-I-1-BOC) by the above method, it was 987. The carbon concentration was 62.1%, and the oxygen concentration was 19.4%.

The following peaks were found by NMR measurement performed on the obtained compound (BisF-I-1-BOC) under the above measurement conditions, and the compound was confirmed to have a chemical structure of the following formula (BisF-I-1-BOC).

δ (ppm) 6.8-7.8 (18H, Ph-H), 6.2 (1H, C—H), 1.6 (36H, C—CH$_3$)

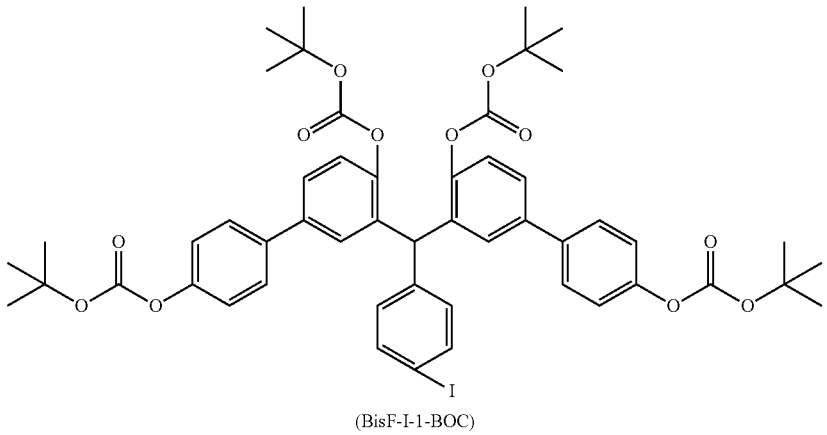 [SMILES: CC(C)(C)OC(=O)Oc1ccc(-c2ccc(OC(=O)OC(C)(C)C)c(C(c3ccc(I)cc3)c3cc(-c4ccc(OC(=O)OC(C)(C)C)cc4)ccc3OC(=O)OC(C)(C)C)c2)cc1]

(BisF-I-1-BOC)

[Synthesis Example 3] Synthesis of BisF-I-2

To a container (internal capacity: 300 mL) equipped with a stirrer, a condenser tube, and a burette, 15.0 g (81 mmol) of 4,4-biphenol (a reagent manufactured by Tokyo Kasei Kogyo Co., Ltd.) and 5.6 g (20 mmol) of 5-iodovanillin (a reagent manufactured by Tokyo Kasei Kogyo Co., Ltd.) were added with 100 mL of γ-butyrolactone, then 0.5 g of p-toluenesulfonic acid was added, and the mixture was reacted by being stirred at 90° C. for 87 hours to obtain a reaction solution. Next, the reaction solution was added to 1000 g of pure water, followed by extraction with ethyl acetate and concentration to obtain a solution.

The obtained solution was subjected to separation by column chromatography and subsequent washing with chloroform to obtain 2.0 g of the objective compound represented by the following formula (BisF-I-2).

As a result of measuring the molecular weight of the obtained compound (BisF-I-2) by the above method, it was 632.

The following peaks were found by NMR measurement performed on the obtained compound (BisF-I-2) under the above measurement conditions, and the compound was confirmed to have a chemical structure of the following formula (BisF-I-2).

δ (ppm) 9.7, 9.3 (5H, O—H), 7.2-8.5 (16H, Ph-H), 6.4 (1H, C—H), 3.7 (3H, O—C—H)

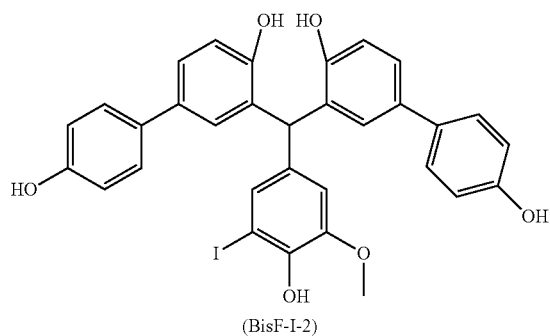 [SMILES: COc1cc(C(c2cc(-c3ccc(O)cc3)ccc2O)c2cc(-c3ccc(O)cc3)ccc2O)cc(I)c1O]

(BisF-I-2)

[Synthesis Working Example 3] Synthesis of BisF-I-2-BOC

To a container (internal capacity: 200 mL) equipped with a stirrer, a condenser tube, and a burette, 6.5 g (12.5 mmol) of the obtained compound (BisF-I-2) and 5.5 g (25 mmol) of di-t-butyl dicarbonate (manufactured by Sigma-Aldrich) were added with 100 mL of acetone, then 3.45 g (25 mmol) of potassium carbonate (manufactured by Sigma-Aldrich) was added, and the contents were reacted by being stirred at 40° C. for 10 hours to obtain a reaction solution. Next, the reaction solution was concentrated. The reaction product was precipitated by the addition of 100 g of pure water to the concentrate. After cooling to room temperature, the solid matter was separated by filtration.

The obtained solid matter was subjected to filtration, dried, and then separated and purified by column chromatography to obtain 1.7 g of the objective compound represented by the following formula (BisF-I-2-BOC).

As a result of measuring the molecular weight of the obtained compound (BisF-I-2-BOC) by the above method, it was 1033. Also, as a result of conducting the organic elemental analysis of the obtained compound (BisF-I-2-BOC), the carbon concentration was 60.6%, and the oxygen concentration was 21.1%.

The following peaks were found by NMR measurement performed on the obtained compound (BisF-I-2-BOC) under the above measurement conditions, and the compound was confirmed to have a chemical structure of the following formula (BisF-I-2-BOC).

δ (ppm) 9.2 (1H, O—H) 7.2-8.6 (16H, Ph-H), 6.2 (1H, C—H), 3.4 (3H, O—C—H), 1.6 (36H, C—CH$_3$)

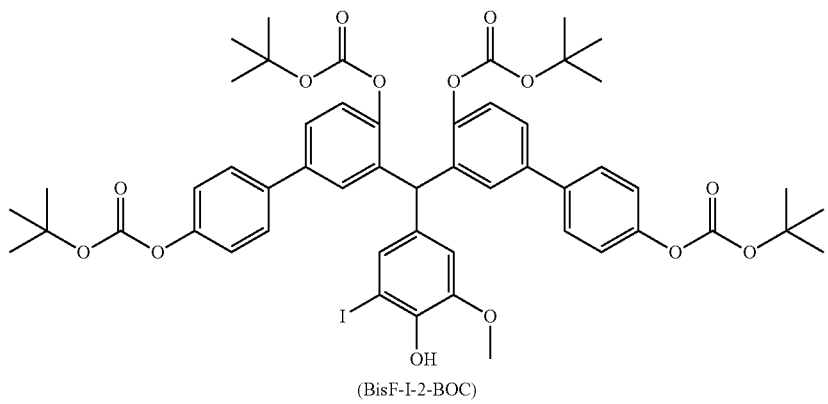 [SMILES: COc1cc(C(c2cc(-c3ccc(OC(=O)OC(C)(C)C)cc3)ccc2OC(=O)OC(C)(C)C)c2cc(-c3ccc(OC(=O)OC(C)(C)C)cc3)ccc2OC(=O)OC(C)(C)C)cc(I)c1O]

(BisF-I-2-BOC)

[Synthesis Example 4] Synthesis of BisF-I-3

To a container (internal capacity: 300 mL) equipped with a stirrer, a condenser tube, and a burette, 15.0 g (81 mmol) of 4,4-biphenol (a reagent manufactured by Tokyo Kasei Kogyo Co., Ltd.) and 9.0 g (40 mmol) of 5-iodo-2-furancarbaldehyde (a reagent manufactured by Tokyo Kasei Kogyo Co., Ltd.) were added with 100 mL of γ-butyrolactone, then 0.5 g of p-toluenesulfonic acid was added, and the mixture was reacted by being stirred at 90° C. for 24 hours to obtain a reaction solution. Next, the reaction solution was added to 300 g of pure water, followed by extraction with ethyl acetate and concentration to obtain a solution.

The obtained solution was subjected to separation by column chromatography and subsequent washing with chloroform to obtain 4.5 g of the objective compound represented by the following formula (BisF-I-3).

As a result of measuring the molecular weight of the obtained compound (BisF-I-3) by the above method, it was 576.

The following peaks were found by NMR measurement performed on the obtained compound (BisF-I-3) under the above measurement conditions, and the compound was confirmed to have a chemical structure of the following formula (BisF-I-3).

δ (ppm) 9.2 (4H, O—H), 7.3-8.7 (16H, Ph-H), 6.2 (1H, C—H)

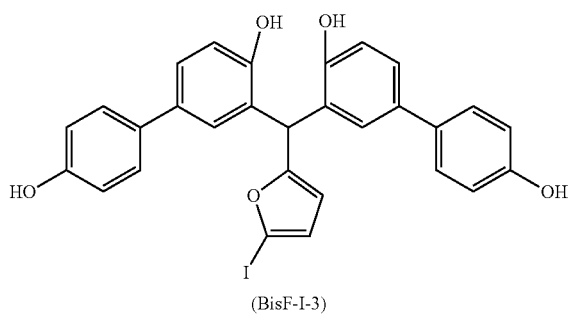 [SMILES: Oc1ccc(-c2ccc(O)c(C(c3ccc(I)o3)c3cc(-c4ccc(O)cc4)ccc3O)c2)cc1]

(BisF-I-3)

[Synthesis Working Example 4] Synthesis of BisF-I-3-BOC

To a container (internal capacity: 200 mL) equipped with a stirrer, a condenser tube, and a burette, 7.2 g (12.5 mmol) of the obtained compound (BisF-I-3) and 5.5 g (25 mmol) of di-t-butyl dicarbonate (manufactured by Sigma-Aldrich) were added with 100 mL of acetone, then 3.45 g (25 mmol) of potassium carbonate (manufactured by Sigma-Aldrich) was added, and the contents were reacted by being stirred at 20° C. for 10 hours to obtain a reaction solution. Next, the reaction solution was concentrated. The reaction product was precipitated by the addition of 100 g of pure water to the concentrate. After cooling to room temperature, the solid matter was separated by filtration.

The obtained solid matter was subjected to filtration, dried, and then separated and purified by column chromatography to obtain 2.6 g of the objective compound represented by the following formula (BisF-I-3-BOC).

As a result of measuring the molecular weight of the obtained compound (BisF-I-3-BOC) by the above method, it was 976. Also, as a result of conducting the organic elemental analysis of the obtained compound (BisF-I-3-BOC), the carbon concentration was 60.3%, and the oxygen concentration was 21.0%.

The following peaks were found by NMR measurement performed on the obtained compound (BisF-I-3-BOC) under the above measurement conditions, and the compound was confirmed to have a chemical structure of the following formula (BisF-I-3-BOC).

δ (ppm) 7.2-8.3 (16H, Ph-H), 6.1 (1H, C—H), 1.6 (36H, C—CH$_3$)

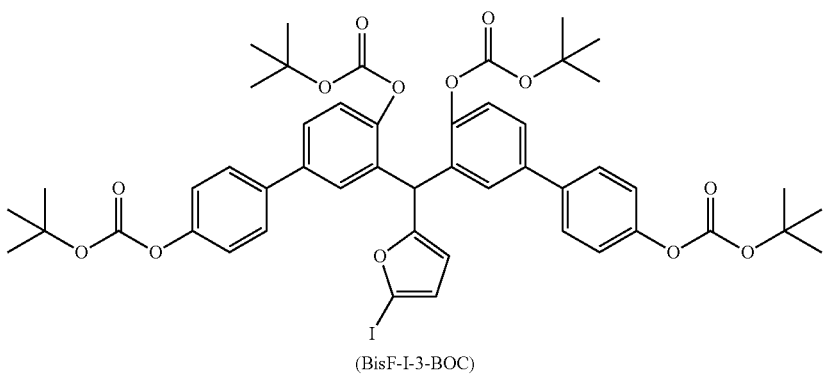 [SMILES: CC(C)(C)OC(=O)Oc1ccc(-c2ccc(OC(=O)OC(C)(C)C)c(C(c3ccc(I)o3)c3cc(-c4ccc(OC(=O)OC(C)(C)C)cc4)ccc3OC(=O)OC(C)(C)C)c2)cc1]

(BisF-I-3-BOC)

[Synthesis Working Example 5] Synthesis of Resin (BisFR-1-BOC)

A four necked flask (internal capacity: 1 L) equipped with a Dimroth condenser tube, a thermometer, and a stirring blade and having a detachable bottom was prepared. To this four necked flask, 65.6 g (70 mmol, manufactured by Mitsubishi Gas Chemical Company, Inc.) of BisF-1-BOC obtained in Synthesis Working Example 1, 21.0 g (280 mmol as formaldehyde) of 40% by mass of an aqueous formalin solution (manufactured by Mitsubishi Gas Chemical Company, Inc.), and 0.97 mL of 98% by mass of sulfuric acid (manufactured by Kanto Chemical Co., Inc.) were added in a nitrogen stream, and the mixture was reacted for 7 hours while refluxed at 100° C. at normal pressure. Subsequently, 180.0 g of o-xylene (special grade reagent manufactured by Wako Pure Chemical Industries, Ltd.) was added as a diluting solvent to the reaction solution, and the mixture was left to stand still, followed by removal of an aqueous phase as a lower phase. Neutralization and washing with water were further performed, and o-xylene was distilled off under reduced pressure to obtain 54.2 g of a brown solid resin (BisFR-1-BOC).

The obtained resin (BisFR-1-BOC) had Mn: 2175, Mw: 4360, and Mw/Mn: 2.0. The carbon concentration was 71.3% by mass, and the oxygen concentration was 20.1% by mass.

[Synthesis Working Example 6] Synthesis of Resin (BisFR-2-BOC)

A four necked flask (internal capacity: 1 L) equipped with a Dimroth condenser tube, a thermometer, and a stirring blade and having a detachable bottom was prepared. To this four necked flask, 65.6 g (70 mmol, manufactured by Mitsubishi Gas Chemical Company, Inc.) of BisF-1-BOC obtained in Synthesis Working Example 1, 50.9 g (280 mmol) of 4-biphenylaldehyde (manufactured by Mitsubishi Gas Chemical Company, Inc.), 100 mL of anisole (manufactured by Kanto Chemical Co., Inc.), and 10 mL of oxalic acid dihydrate (manufactured by Kanto Chemical Co., Inc.) were added in a nitrogen stream, and the mixture was reacted for 12 hours while refluxed at 100° C. at normal pressure. Subsequently, 180.0 g of o-xylene (special grade reagent manufactured by Wako Pure Chemical Industries, Ltd.) was added as a diluting solvent to the reaction solution, and the mixture was left to stand still, followed by removal of an aqueous phase as a lower phase. Neutralization and washing with water were further performed, and the solvents and unreacted 4-biphenylaldehyde in the organic phase were distilled off under reduced pressure to obtain 87.7 g of a brown solid resin (BisFR-2-BOC).

The obtained resin (BisFR-2-BOC) had Mn: 2382, Mw: 4510, and Mw/Mn: 1.89. The carbon concentration was 75.2% by mass, and the oxygen concentration was 19.5% by mass.

Synthesis Comparative Example 1

A four necked flask (internal capacity: 10 L) equipped with a Dimroth condenser tube, a thermometer, and a stirring blade and having a detachable bottom was prepared. To this four necked flask, 1.09 kg (7 mol) of 1,5-dimethylnaphthalene (manufactured by Mitsubishi Gas Chemical Company, Inc.), 2.1 kg (28 mol as formaldehyde) of 40% by mass of an aqueous formalin solution (manufactured by Mitsubishi Gas Chemical Company, Inc.), and 0.97 mL of 98% by mass of sulfuric acid (manufactured by Kanto Chemical Co., Inc.) were added in a nitrogen stream, and the mixture was reacted for 7 hours while refluxed at 100° C. at normal pressure. Subsequently, 1.8 kg of ethylbenzene (special grade reagent manufactured by Wako Pure Chemical Industries, Ltd.) was added as a diluting solvent to the reaction solution, and the mixture was left to stand still, followed by removal of an aqueous phase as a lower phase. Neutralization and washing with water were further performed, and ethylbenzene and unreacted 1,5-dimethylnaphthalene were distilled off under reduced pressure to obtain 1.25 kg of a light brown solid dimethylnaphthalene formaldehyde resin.

The molecular weight of the obtained dimethylnaphthalene formaldehyde was Mn: 562.

Subsequently, a four necked flask (internal capacity: 0.5 L) equipped with a Dimroth condenser tube, a thermometer, and a stirring blade was prepared. To this four necked flask, 100 g (0.51 mol) of the dimethylnaphthalene formaldehyde resin thus obtained, and 0.05 g of p-toluenesulfonic acid were added in a nitrogen stream, and the temperature was raised to 190° C. at which the mixture was then heated for 2 hours, followed by stirring. Subsequently, 52.0 g (0.36 mol) of 1-naphthol was added thereto, and the temperature was further raised to 220° C. at which the mixture was reacted for 2 hours. After solvent dilution, neutralization and washing with water were performed, and the solvent was removed under reduced pressure to obtain 126.1 g of a black-brown solid modified resin (CR-1).

The obtained resin (CR-1) had Mn: 885, Mw: 2220, and Mw/Mn: 4.17. The carbon concentration was 89.1% by mass, and the oxygen concentration was 4.5% by mass.

Examples 1 to 6 and Comparative Example 1

(Heat Resistance and Solubility)
Results of conducting heat resistance test and solubility test using BisF-1-BOC, BisF-I-1-BOC, BisF-I-2-BOC, BisF-I-3-BOC, BisFR-1-BOC, BisFR-2-BOC, and CR-1 are shown in Table 1.

(Preparation of Resist Composition)
A resist composition was prepared according to the recipe shown in Table 1 using each compound synthesized as described above. Among the components of the resist composition in Table 1, the following acid generating agent (C), acid diffusion controlling agent (E), and solvent were used.
Acid Generating Agent (C)
P-1: triphenylbenzenesulfonium trifluoromethanesulfonate (Midori Kagaku Co., Ltd.) Acid diffusion controlling agent (E)
Q-1: trioctylamine (Tokyo Kasei Kogyo Co., Ltd.) Solvent
S-1: propylene glycol monomethyl ether (Tokyo Kasei Kogyo Co., Ltd.)

(Evaluating Resist Performance of Resist composition)
A clean silicon wafer was spin coated with the homogeneous resist composition, and then prebaked (PB) before exposure in an oven of 110° C. to form a resist film with a thickness of 60 nm. The obtained resist film was irradiated with electron beams of 1:1 line and space setting with a 50 nm interval using an electron beam lithography system (ELS-7500 manufactured by ELIONIX INC.). After irradiation, the resist film was heated at each predetermined temperature for 90 seconds, and immersed in 2.38% by mass TMAH alkaline developing solution for 60 seconds for development. Subsequently, the resist film was washed with ultrapure water for 30 seconds, and dried to form a positive type resist pattern. Concerning the formed resist pattern, the line and space were observed by a scanning electron microscope (S-4800 manufactured by Hitachi High-Technologies Corporation) to evaluate the reactivity by electron beam irradiation of the resist composition.

TABLE 1

| | Compound | Heat resistance evaluation | Solvent solubility evaluation | Resist composition | | | | Resist performance evaluation |
|---|---|---|---|---|---|---|---|---|
| | | | | Compound of synthesis example [g] | P-1 [g] | Q-1 [g] | S-1 [g] | |
| Example 1 | BisF-1-BOC | A | A | 1.0 | 0.3 | 0.03 | 50.0 | Good |
| Example 2 | BisF-I-1-BOC | A | A | 1.0 | 0.3 | 0.03 | 50.0 | Good |
| Example 3 | BisF-I-2-BOC | A | A | 1.0 | 0.3 | 0.03 | 50.0 | Good |
| Example 4 | BisF-I-3-BOC | A | A | 1.0 | 0.3 | 0.03 | 50.0 | Good |
| Example 5 | BisFR-1-BOC | B | A | 1.0 | 0.3 | 0.03 | 50.0 | Good |
| Example 6 | BisF-2-BOC | A | A | 1.0 | 0.3 | 0.03 | 50.0 | Good |
| Comparative Example 1 | CR-1 | C | C | 1.0 | 0.3 | 0.03 | 50.0 | Poor |

As is evident from Table 1, it was able to be confirmed that the compounds used in Examples 1 to 6 (BisF-1-BOC, BisF-I-1-BOC, BisF-I-2-BOC, BisF-I-3-BOC, BisFR-1-BOC, and BisFR-2-BOC, respectively) have good heat resistance and solubility whereas the compound (CR-1) used in Comparative Example 1 is inferior in heat resistance and solubility.

In resist pattern evaluation, a good resist pattern was obtained by irradiation with electron beams of 1:1 line and space setting with a 50 nm interval in Examples 1 to 6. On the other hand, no good resist pattern was able to be obtained in Comparative Example 1.

Thus, the compound that satisfies the requirements of the present invention has high heat resistance and high solubility in a safe solvent. Also, the resist composition comprising the compound can impart a good shape to a resist pattern, as compared with the resist composition comprising the comparative compound (CR-1). As long as the above requirements of the present invention are met, compounds other than those described in Examples also exhibit the same effects.

Examples 7 to 12 and Comparative Example 2

(Preparation of Radiation-Sensitive Composition)

The components set forth in Table 2 were prepared and formed into homogeneous solutions, and the obtained homogeneous solutions were filtered through a Teflon (R) membrane filter with a pore diameter of 0.1 μm to prepare radiation-sensitive compositions. Each prepared radiation-sensitive composition was evaluated as described below.

TABLE 2

| | Composition | | |
|---|---|---|---|
| | Component (A) [g] | Optically active compound (B) [g] | Solvent [g] |
| Example 7 | BisF-1-BOC 0.5 | B-1 1.5 | S-1 30.0 |
| Example 8 | BisF-I-1-BOC 0.5 | B-1 1.5 | S-1 30.0 |
| Example 9 | BisF-I-2-BOC 0.5 | B-1 1.5 | S-1 30.0 |
| Example 10 | BisF-I-3-BOC 0.5 | B-1 1.5 | S-1 30.0 |
| Example 11 | BisFR-1-BOC 0.5 | B-1 1.5 | S-1 30.0 |
| Example 12 | BisFR-2-BOC 0.5 | B-1 1.5 | S-1 30.0 |
| Comparative Example 2 | PHS-1 0.5 | B-1 1.5 | S-1 30.0 |

The following resist base material was used in Comparative Example 2.
PHS-1: polyhydroxystyrene Mw=8000 (Sigma-Aldrich)
The following optically active compound (B) was used.
B-1: naphthoquinonediazide-based sensitizing agent of the chemical structural formula (G) (4NT-300, Toyo Gosei Co., Ltd.)
The following solvent was used.
S-1: propylene glycol monomethyl ether (Tokyo Kasei Kogyo Co., Ltd.)

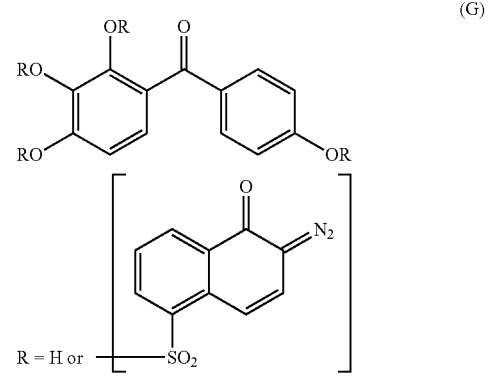

(G)

(Evaluation of Resist Performance of Radiation-Sensitive Composition)

A clean silicon wafer was spin coated with the radiation-sensitive composition obtained as described above, and then prebaked (PB) before exposure in an oven of 110° C. to form a resist film with a thickness of 200 nm. The resist film was exposed to ultraviolet using an ultraviolet exposure apparatus (mask aligner MA-10 manufactured by Mikasa Co., Ltd.). The ultraviolet lamp used was a super high pressure mercury lamp (relative intensity ratio: g-ray:h-ray:i-ray:j- ray=100:80:90:60). After irradiation, the resist film was heated at 110° C. for 90 seconds, and immersed in 2.38% by mass TMAH alkaline developing solution for 60 seconds for development. Subsequently, the resist film was washed with ultrapure water for 30 seconds, and dried to form a 5 µm positive type resist pattern.

The obtained line and space were observed in the formed resist pattern by a scanning electron microscope (S-4800 manufactured by Hitachi High-Technologies Corporation). As for the line edge roughness, a pattern having asperities of less than 50 nm was evaluated as goodness.

In the case of using the radiation-sensitive compositions of Examples 7 to 12 a good resist pattern with a resolution of 5 m was able to be obtained. The roughness of the pattern was also small and good.

On the other hand, in the case of using the radiation-sensitive composition of Comparative Example 2, a good resist pattern with a resolution of 5 m was able to be obtained. However, the roughness of the pattern was large and poor.

As described above, it was found that a resist pattern that has small roughness and a good shape can be formed in present Examples 7 to 12 as compared with Comparative Example 2. As long as the above requirements of the present invention are met, radiation-sensitive compositions other than those described in Examples also exhibit the same effects.

The compounds obtained in Synthesis Examples 1 to 6 have a relatively low molecular weight and a low viscosity, and all of their glass transition temperatures are as low as 100° C. or lower. Therefore, the embedding properties of underlayer film forming materials for lithography containing these compounds can be relatively advantageously enhanced. Furthermore, all of their thermal decomposition temperatures are 150° C. or higher (evaluation A), and high heat resistance is retained because of their rigid structures after elimination of acid dissociation groups. Therefore, the materials can be used even under high temperature baking conditions.

Examples 13 to 18 and Comparative Example 3

(Preparation of Composition for Underlayer Film Formation for Lithography)

Compositions for underlayer film formation for lithography were prepared according to the composition shown in Table 3. Specifically, the following materials were used.

Acid generating agent: di-tertiary butyl diphenyliodonium nonafluoromethanesulfonate (DTDPI) manufactured by Midori Kagaku Co., Ltd.

Crosslinking agent: NIKALAC MX270 (NIKALAC) (Sanwa Chemical Co., Ltd.)

Organic solvent: propylene glycol monomethyl ether acetate (PGMEA)

Novolac: PSM4357 manufactured by Gunei Chemical Industry Co., Ltd.

Next, etching test was conducted under conditions shown below to evaluate etching resistance. The evaluation results are shown in Table 3.

[Etching Test]
Etching apparatus: RIE-10NR manufactured by Samco International, Inc.
Output: 50 W
Pressure: 20 Pa
Time: 2 min
Etching gas Ar gas flow rate:$CF_4$ gas flow rate:$O_2$ gas flow rate=50:5:5 (sccm)

(Evaluation of Etching Resistance)

The evaluation of etching resistance was conducted by the following procedures.

First, an underlayer film of novolac was prepared under the same conditions as in Example 13 except that novolac (PSM4357 manufactured by Gunei Chemical Industry Co., Ltd.) was used instead of the compound (BisF-1-BOC) used in Example 13. Then, this underlayer film of novolac was subjected to the above etching test, and the etching rate was measured.

Next, underlayer films of Examples 13 to 18 and Comparative Example 3 were subjected to the above etching test in the same way as above, and the etching rate was measured.

Then, the etching resistance was evaluated according to the following evaluation criteria on the basis of the etching rate of the underlayer film of novolac.

—Evaluation Criteria—
A: The etching rate was less than −10% as compared with the underlayer film of novolac.
B: The etching rate was −10% to +5% as compared with the underlayer film of novolac.
C: The etching rate was more than +5% as compared with the underlayer film of novolac.

TABLE 3

| | Underlayer film forming material (part by mass) | Solvent (part by mass) | Acid generating agent (part by mass) | Cross-linking agent (part by mass) | Evaluation of etching resistance |
|---|---|---|---|---|---|
| Example 13 | BisF-1-BOC (10) | PGMEA (90) | DTDPI (0.5) | NIKALAC (0.5) | A |
| Example 14 | BisF-I-1-BOC (10) | PGMEA (90) | DTDPI (0.5) | NIKALAC (0.5) | A |
| Example 15 | BisF-I-2-BOC (10) | PGMEA (90) | DTDPI (0.5) | NIKALAC (0.5) | A |
| Example 16 | BisF-I-3-BOC (10) | PGMEA (90) | DTDPI (0.5) | NIKALAC (0.5) | A |
| Example 17 | BisFR-1-BOC (10) | PGMEA (90) | DTDPI (0.5) | NIKALAC (0.5) | B |
| Example 18 | BisFR-2-BOC (10) | PGMEA (90) | DTDPI (0.5) | NIKALAC (0.5) | A |
| Comparative Example 3 | CR-1 (10) | PGMEA (90) | DTDPI (0.5) | NIKALAC (0.5) | C |

Example 19

Next, a $SiO_2$ substrate with a film thickness of 300 nm was coated with the composition for underlayer film formation for lithography of Example 13, and baked at 240° C. for 60 seconds and further at 400° C. for 120 seconds to form an underlayer film with a film thickness of 85 nm. This underlayer film was coated with a resist solution for ArF and baked at 130° C. for 60 seconds to form a photoresist layer with a film thickness of 140 nm.

The ArF resist solution used was prepared by containing 5 parts by mass of a compound of the formula (5) given below, 1 part by mass of triphenylsulfonium nonafluoromethanesulfonate, 2 parts by mass of tributylamine, and 92 parts by mass of PGMEA.

The compound of the formula (5) was prepared as follows. 4.15 g of 2-methyl-2-methacryloyloxyadamantane, 3.00 g of methacryloyloxy-γ-butyrolactone, 2.08 g of 3-hydroxy-1-adamantyl methacrylate, and 0.38 g of azobisisobutyronitrile were dissolved in 80 mL of tetrahydrofuran to prepare a reaction solution. This reaction solution was polymerized for 22 hours with the reaction temperature kept at 63° C. in a nitrogen atmosphere. Then, the reaction solution was added dropwise into 400 mL of n-hexane. The product resin thus obtained was solidified and purified, and the resulting white powder was filtered and dried overnight at 40° C. under reduced pressure to obtain a compound represented by the following formula.

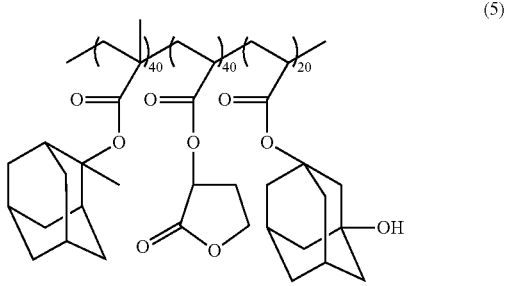

(5)

wherein 40, 40, and 20 represent the ratio of each constituent unit and do not represent a block copolymer.

Subsequently, the photoresist layer was exposed using an electron beam lithography system (manufactured by ELIONIX INC.; ELS-7500, 50 keV), baked (PEB) at 115° C. for 90 seconds, and developed for 60 seconds in 2.38% by mass tetramethylammonium hydroxide (TMAH) aqueous solution to obtain a positive type resist pattern.

Comparative Example 4

The same operations as in Example 19 were performed except that no underlayer film was formed so that a photoresist layer was formed directly on a $SiO_2$ substrate to obtain a positive type resist pattern.

[Evaluation]

Concerning each of Example 19 and Comparative Example 4, the shapes of the obtained 45 nm L/S (1:1) and 80 nm L/S (1:1) resist patterns were observed under an electron microscope manufactured by Hitachi, Ltd. (S-4800). The shapes of the resist patterns after development were evaluated as goodness when having good rectangularity without pattern collapse, and as poorness if this was not the case. The smallest line width having good rectangularity without pattern collapse as a result of this observation was used as an index for resolution evaluation. The smallest electron beam energy quantity capable of lithographing good pattern shapes was used as an index for sensitivity evaluation. The results are shown in Table 4.

TABLE 4

| | Underlayer film forming material | Resolution (nmL/S) | Sensitivity (μC/cm$^2$) | Resist pattern shape after development |
|---|---|---|---|---|
| Example 19 | As described in Example 13 | 45 | 10 | Good |
| Comparative Example 4 | None | 80 | 26 | Poor |

As is evident from Table 4, the underlayer film of Example 19 was confirmed to be significantly superior in both resolution and sensitivity to Comparative Example 4. Also, the resist pattern shapes after development were confirmed to have good rectangularity without pattern collapse. The difference in the resist pattern shapes after development indicated that the underlayer film forming material for lithography of Example 19 has good adhesiveness to a resist material.

Example 20

A $SiO_2$ substrate with a film thickness of 300 nm was coated with the composition for underlayer film formation for lithography used in Example 13, and baked at 240° C. for 60 seconds and further at 400° C. for 120 seconds to form an underlayer film with a film thickness of 90 nm. This underlayer film was coated with a silicon-containing intermediate layer material and baked at 200° C. for 60 seconds to form an intermediate layer film with a film thickness of 35 nm. This intermediate layer film was further coated with the above resist solution for ArF and baked at 130° C. for 60 seconds to form a photoresist layer with a film thickness of 150 nm. The silicon-containing intermediate layer material used was the silicon atom-containing polymer described in <Synthesis Example 1> of Japanese Patent Laid-Open No. 2007-226170.

Subsequently, the photoresist layer was mask exposed using an electron beam lithography system (manufactured by ELIONIX INC.; ELS-7500, 50 keV), baked (PEB) at 115° C. for 90 seconds, and developed for 60 seconds in 2.38% by mass tetramethylammonium hydroxide (TMAH) aqueous solution to obtain a 45 nm L/S (1:1) positive type resist pattern.

Then, the silicon-containing intermediate layer film (SOG) was dry etched with the obtained resist pattern as a mask using RIE-10NR manufactured by Samco International, Inc. Subsequently, dry etching of the underlayer film with the obtained silicon-containing intermediate layer film pattern as a mask and dry etching of the $SiO_2$ film with the obtained underlayer film pattern as a mask were performed in order.

Respective etching conditions are as shown below.

Conditions for Etching of Resist Intermediate Layer Film with Resist Pattern
Output: 50 W
Pressure: 20 Pa
Time: 1 min
Etching gas
Ar gas flow rate:$CF_4$ gas flow rate:$O_2$ gas flow rate=50:8:2 (sccm)

Conditions for Etching of Resist Underlayer Film with Resist Intermediate Film Pattern
Output: 50 W
Pressure: 20 Pa
Time: 2 min
Etching gas
Ar gas flow rate:$CF_4$ gas flow rate:$O_2$ gas flow rate=50:5:5 (sccm)

Conditions for Etching of $SiO_2$ Film with Resist Underlayer Film Pattern
Output: 50 W
Pressure: 20 Pa
Time: 2 min
Etching gas
Ar gas flow rate:$C_5F_{12}$ gas flow rate:$C_2F_6$ gas flow rate:$O_2$ gas flow rate=50:4:3:1 (sccm)

[Evaluation]

The pattern cross section (the shape of the SiO$_2$ film after etching) of Example 20 obtained as described above was observed under an electron microscope manufactured by Hitachi, Ltd. (S-4800). As a result, it was confirmed that the shape of the SiO$_2$ film after etching in a multilayer resist process is a rectangular shape in Examples using the underlayer film of the present invention and is good without defects.

As mentioned above, the present embodiment is not limited to the above examples, and changes or modifications can be arbitrarily made without departing from the spirit of the present invention.

The present invention can provide a compound having high solubility in a safe solvent and high heat resistance, and a resin comprising the compound as a constituent. Accordingly, the present invention is suitably used for, for example, base materials of photosensitive materials such as photoresists for semiconductors, raw materials or curing agents of epoxy resins used for, for example, encapsulating materials of integrated circuits, color developers or discoloration inhibitors used for heat-sensitive recording materials, and, in addition, additives for germicides and antimicrobial/antifungal agents, etc.

Also, according to the present invention, a compound represented by the above formula (1) and/or a resin comprising the compound as a constituent, having a reduced metal content can be industrially advantageously produced.

The resist composition of the present invention contains a compound having a specific structure and having high solubility in a safe solvent and imparts a shape to a resist pattern. Accordingly, the present invention is useful in the semiconductor field, the display field, photomasks, thin film magnetic heads, compound semiconductors, research and development, and the like where resist compositions such as acid amplified non-polymeric resist materials are used.

Furthermore, the present invention is suitably used in a radiation-sensitive composition and a resist pattern formation method using the composition. Particularly, the radiation-sensitive composition of the present invention comprises a resist base material represented by a specific chemical structural formula, an optically active compound, and a solvent and is thereby useful as, for example, a non-chemically amplified low molecular resist material.

Moreover, the compound of the present invention and the resin comprising the compound as a constituent have relatively high heat resistance and also relatively high solvent solubility and are applicable to a wet process. Therefore, an underlayer film forming material for lithography containing the compound and/or the resin of the present invention, and a composition comprising the material can be used widely and effectively for various purposes required to have such performance. Accordingly, the present invention can be used widely and effectively in, for example, electrical insulating materials, resins for resists, encapsulation resins for semiconductors, adhesives for printed circuit boards, electrical laminates mounted in electric equipment, electronic equipment, industrial equipment, and the like, matrix resins of prepregs mounted in electric equipment, electronic equipment, industrial equipment, and the like, buildup laminate materials, resins for fiber-reinforced plastics, resins for encapsulation of liquid crystal display panels, coating materials, various coating agents, adhesives, coating agents for semiconductors, resins for resists for semiconductors, and resins for underlayer film formation. Particularly, the present invention can be effectively used in the fields of underlayer films for lithography and underlayer films for multilayer resists.

The disclosure of Japanese Patent Application No. 2015-178545 filed on Sep. 10, 2015 in the Japan Patent Office is incorporated herein by reference in its entirety.

All literatures, patent applications, and technical standards described herein are incorporated herein by reference to the same extent as if each individual literature, patent application, or technical standard is specifically and individually indicated to be incorporated by reference.

The invention claimed is:

1. A compound represented by the following formula (1):

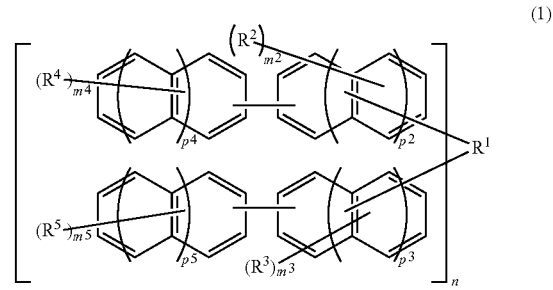

wherein $R^2$ to $R^5$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, a hydroxy group, or a group in which a hydrogen atom of a hydroxy group is replaced with an acid dissociation group, provided that at least one selected from $R^2$ to $R^5$ is a group in which a hydrogen atom of a hydroxy group is replaced with an acid dissociation group; $m^2$ and $m^3$ are each independently an integer of 0 to 8; $m^4$ and $m^5$ are each independently an integer of 0 to 9, provided that $m^2$, $m^3$, $m^4$, and $m^5$ are not 0 at the same time; n is an integer of 1 to 4; $p^2$ to $p^5$ are each independently an integer of 0 to 2; when is 1, $R^1$ includes at least one selected from the group consisting of a heterocyclic group or an aromatic group of 6 to 30 carbon atoms; and when n is 2, 3, or 4, $R_1$ is a 2n-valent group of 1 to 60 carbon atoms or a single bond.

2. The compound according to claim 1, wherein at least one selected from the group consisting of $R^4$ and $R^5$ is a group in which a hydrogen atom of a hydroxy group is replaced with an acid dissociation group.

3. The compound according to claim 1, wherein at least one selected from the group consisting of $R^2$ and $R^3$ is a group in which a hydrogen atom of a hydroxy group is replaced with an acid dissociation group.

4. A compound represented by the following formula (1):

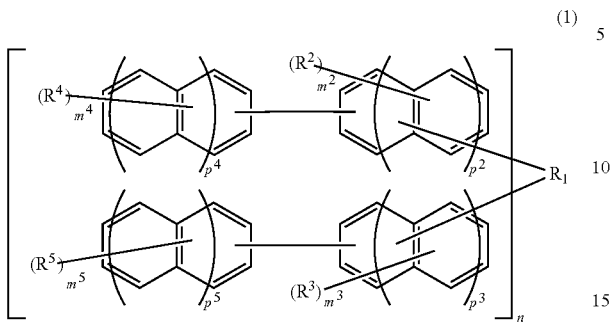

wherein $R^1$ is a 2n-valent group of 1 to 60 carbon atoms or a single bond; $R^2$ to $R^5$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, a thiol group, a hydroxy group, or a group in which a hydrogen atom of a hydroxy group is replaced with an acid dissociation group, provided that at least one selected from $R^2$ to $R^5$ is a group in which a hydrogen atom of a hydroxy group is replaced with an acid dissociation group; $m^2$ and $m^3$ are each independently an integer of 0 to 8; $m^4$ and $m^5$ are each independently an integer of 0 to 9, provided that $m^2$, $m^3$, $m^4$, and $m^5$ are not 0 at the same time; n is an integer of 1 to 4; and $p^2$ to $p^5$ are each independently an integer of 0 to 2, wherein at least one selected from the group consisting of $R^1$ to $R^5$ is a group containing an iodine atom.

5. The compound according to claim 1, wherein the compound represented by the formula (1) is a compound represented by the following formula (1a):

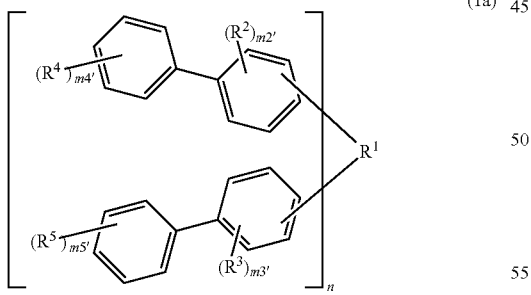

wherein $R^1$ to $R^5$ and n are as defined in the description of the formula (1), provided that at least one selected from the group consisting of $R^2$ to $R^5$ is a group in which a hydrogen atom of a hydroxy group is replaced with an acid dissociation group; $m^{2'}$ and $m^{3'}$ are each independently an integer of 0 to 4; and $m^{4'}$ and $m^{5'}$ are each independently an integer of 0 to 5, provided that $m^{2'}$, $m^{3'}$, $m^{4'}$, and $m^{5'}$ are not 0 at the same time.

6. A compound represented by the following formula (1b):

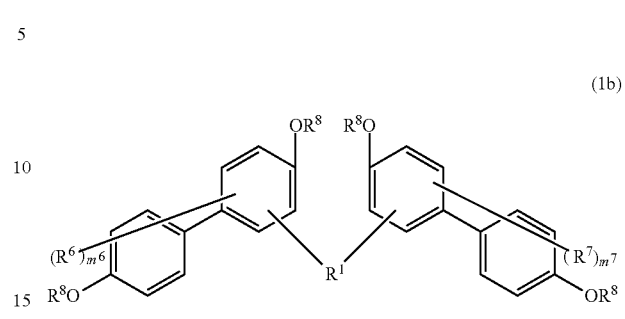

wherein $R^1$ is a 2n-valent group of 1 to 60 carbon atoms or a single bond; $R^6$ and $R^7$ are each independently a linear, branched, or cyclic alkyl group of 1 to 10 carbon atoms, an aryl group of 6 to 10 carbon atoms, an alkenyl group of 2 to 10 carbon atoms, an alkoxy group of 1 to 30 carbon atoms, a halogen atom, or a thiol group; each $R^8$ is independently a hydrogen atom or an acid dissociation group, provided that at least one $R^8$ is an acid dissociation group; and $m^6$ and $m^7$ are each independently an integer of 0 to 7.

7. The compound according to claim 6, wherein the compound represented by the formula (1b) is a compound represented by the following formula (1c):

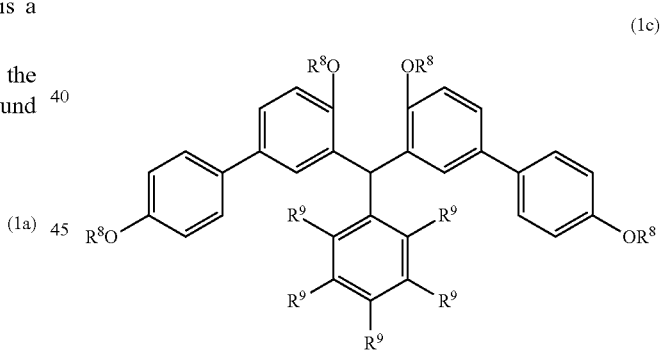

wherein $R^8$ is as defined in the description of the formula (1b); and each $R^9$ is independently a hydrogen atom, a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkoxy group of 1 to 30 carbon atoms, a thiol group, or a hydroxy group, provided that at least one $R^8$ is an acid dissociation group.

8. The compound according to claim 7, wherein the compound represented by the formula (1c) is a compound represented by the following formula (1d):

(1d)

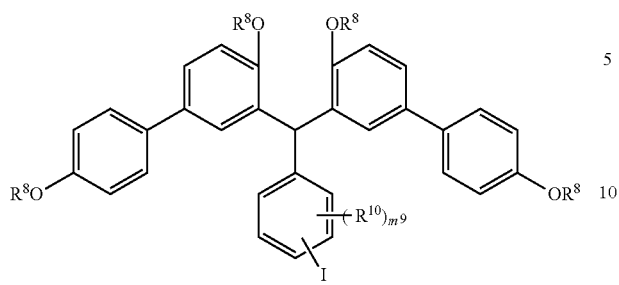

wherein $R^8$ is as defined in the description of the formula (1b); each $R^{10}$ is independently a cyano group, a nitro group, a heterocyclic group, a halogen atom, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an alkoxy group of 1 to 30 carbon atoms, a thiol group, or a hydroxy group; and $m^9$ is an integer of 0 to 4, provided that at least one $R^8$ is an acid dissociation group.

9. A resist composition comprising the compound according to claim 1 and an acid generating agent.

10. The resist composition according to claim 9, further comprising a solvent.

11. The resist composition according to claim 10, further comprising an acid diffusion controlling agent.

12. A purification method comprising the steps of:
   obtaining a solution (S) by dissolving the compound according to claim 1 in a solvent; and
   extracting impurities in the compound and/or the resin by bringing the obtained solution (S) into contact with an acidic aqueous solution (a first extraction step), wherein
   the solvent used in the step of obtaining the solution (S) comprises a solvent that does not inadvertently mix with water.

13. The purification method according to claim 12, wherein
   the acidic aqueous solution is an aqueous mineral acid solution or an aqueous organic acid solution;
   the aqueous mineral acid solution is one or more aqueous mineral acid solutions selected from the group consisting of hydrochloric acid, sulfuric acid, nitric acid, and phosphoric acid; and
   the aqueous organic acid solution is one or more aqueous organic acid solutions selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid.

* * * * *

UNITED STATES PATENT AND TRADEMARK OFFICE
CERTIFICATE OF CORRECTION

PATENT NO. : 11,243,467 B2
APPLICATION NO. : 15/759076
DATED : February 8, 2022
INVENTOR(S) : Takumi Toida et al.

It is certified that error appears in the above-identified patent and that said Letters Patent is hereby corrected as shown below:

In the Claims

Column 130, Line (53):
In Claim 1, after "when", please insert -- n --.

Column 130, Line (56):
In Claim 1, please delete "$R_1$" and insert -- $R^1$ --, therefor.

Signed and Sealed this
Sixth Day of September, 2022

Katherine Kelly Vidal
*Director of the United States Patent and Trademark Office*